US012590299B2

(12) United States Patent
Joung et al.

(10) Patent No.: US 12,590,299 B2
(45) Date of Patent: Mar. 31, 2026

(54) VARIANTS OF CRISPR FROM *PREVOTELLA* AND *FRANCISELLA* 1 (CPF1)

(71) Applicant: The General Hospital Corporation, Boston, MA (US)

(72) Inventors: J. Keith Joung, Winchester, MA (US); Benjamin Kleinstiver, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 1196 days.

(21) Appl. No.: 17/450,593

(22) Filed: Oct. 12, 2021

(65) Prior Publication Data

US 2022/0025347 A1 Jan. 27, 2022

Related U.S. Application Data

(62) Division of application No. 15/659,499, filed on Jul. 25, 2017, now Pat. No. 11,168,313.

(60) Provisional application No. 62/366,976, filed on Jul. 26, 2016.

(51) Int. Cl.

| | |
|---|---|
| ***C12N 9/22*** | (2006.01) |
| ***C07K 14/39*** | (2006.01) |
| ***C12N 9/02*** | (2006.01) |
| ***C12N 15/11*** | (2006.01) |
| ***C12N 15/90*** | (2006.01) |

(52) U.S. Cl.

CPC ................ *C12N 9/22* (2013.01); *C07K 14/39* (2013.01); *C12N 9/0071* (2013.01); *C12N 15/11* (2013.01); *C12N 15/907* (2013.01); *C12Y 114/11* (2013.01); *C12Y 301/21004* (2013.01); *C07K 2319/00* (2013.01); *C07K 2319/80* (2013.01); *C12N 2310/20* (2017.05)

(58) Field of Classification Search

CPC ........ C12N 9/22; C12N 9/0071; C12N 15/11; C12N 15/907; C12N 2310/20; C12N 15/1137; C07K 14/39; C07K 2319/00; C07K 2319/80; C12Y 114/11; C12Y 301/21004; Y02A 50/30

See application file for complete search history.

(56) References Cited

U.S. PATENT DOCUMENTS

| | | | |
|---|---|---|---|
| 11,866,745 | B2 | 1/2024 | Watts et al. |
| 2011/0136895 | A1 | 6/2011 | Gregory et al. |
| 2014/0068797 | A1 | 3/2014 | Doudna et al. |
| 2014/0273226 | A1 | 9/2014 | Wu |
| 2014/0315985 | A1 | 10/2014 | May et al. |
| 2016/0208243 | A1 | 7/2016 | Zhang et al. |
| 2017/0058271 | A1 | 3/2017 | Joung et al. |
| 2017/0233756 | A1 | 8/2017 | Begemann et al. |
| 2017/0362644 | A1 | 12/2017 | Doudna et al. |
| 2018/0100148 | A1 | 4/2018 | Vakulskas et al. |
| 2018/0282714 | A1 | 10/2018 | Joung et al. |
| 2019/0106687 | A1 | 4/2019 | Joung et al. |
| 2019/0382775 | A1 | 12/2019 | Tan et al. |
| 2021/0269788 | A1 | 9/2021 | Joung et al. |

FOREIGN PATENT DOCUMENTS

| | | |
|---|---|---|
| CN | 105408483 | 3/2016 |
| CN | 105543195 | 5/2016 |
| CN | 106244591 | 12/2016 |
| CN | 106479985 | 3/2017 |
| WO | WO 2015/089364 | 6/2015 |
| WO | WO 2016/115179 | 7/2016 |
| WO | WO 2016/115355 | 7/2016 |
| WO | WO 2016/141224 | 9/2016 |
| WO | WO 2017/015015 | 1/2017 |
| WO | WO 2017/040348 | 3/2017 |
| WO | WO 2017/070633 | 4/2017 |
| WO | WO 2017/127807 | 7/2017 |
| WO | WO 2017/184768 | 10/2017 |
| WO | WO 2017/219027 | 12/2017 |
| WO | WO 2018/022634 | 2/2018 |
| WO | WO 2018/226855 | 12/2018 |
| WO | WO 2019/040650 | 2/2019 |
| WO | WO 2019/126762 | 6/2019 |
| WO | WO 2021/151073 | 7/2021 |
| WO | WO 2021/151085 | 7/2021 |

OTHER PUBLICATIONS

Notice of Acceptance in Australian Appln. No. 2017302551, dated Apr. 12, 2023, 3 pages.
Office Action in Chinese Appln. No. 201780059001.5, dated Apr. 12, 2023, 17 pages (with English translation).
Office Action in Chinese Appln. No. 201780059001.5, dated Aug. 24, 2023, 12 pages (with English translation).
Office Action in Canadian Appln. No. 3,031,414, dated Jun. 23, 2023, 4 pages.
Chavez et al., "Highly-efficient Cas9-mediated transcriptional programming," Nat Methods., 2015, 12:326-8.
Chen et al., "CRISPR-Cas12a target binding unleashes indiscriminate single-stranded DNase activity," Science, 2018, 8 pages.
Chen et al., "Supplementary Materials for CRISPR-Cas12a target binding unleashes indiscriminate single-stranded DNase activity," Science, 2018, 28 pages.
East-Seletsky et al., "Two Distinct RNase Activities of CRISPR-C2c2 Enable Guide RNA Processing and RNA Detection," Nature, 2016, 538(7624): 270-273, 26 pages.
Gao et al., "Engineered Cpf1 Enzymes with Altered PAM Specificities," BioRxiv Preprint, 2016, 091611, 17 pages.
Gaudelli et al., "Programmable base editing of A•T to G•C in genomic DNA without DNA cleavage," Nature. 2017, 551(7681):464-471, 37 pages.
Gootenberg et al., "Multiplexed and portable nucleic acid detection platform with Cas13, Cas12a, and Csm6," Science, 2018, 10 pages.
Gootenberg et al., "Nucleic acid detection with CRISPR-Cas13a/C2c2," Science, 2017, 356: 438-442.

(Continued)

*Primary Examiner* — Neil P Hammell
*Assistant Examiner* — Kyle T Rega
(74) *Attorney, Agent, or Firm* — Fish & Richardson P.C.

(57) ABSTRACT

Engineered CRISPR from *Prevotella* and *Francisella* 1 (Cpf1) nucleases with altered and improved target specificity and their use in genomic engineering, epigenomic engineering, genome targeting, genome editing, and in vitro diagnostics.

33 Claims, 8 Drawing Sheets

Specification includes a Sequence Listing.

(56) References Cited

OTHER PUBLICATIONS

Gootenberg et al., "Supplementary Materials for Multiplexed and portable nucleic acid detection platform with Cas13, Cas12a, and Csm6," Science, 2018, 85 pages.
Gootenberg et al., "Supplementary Materials for Nucleic acid detection with CRISPR-Cas13a/C2c2," Science, 2017, 45 pages.
International Preliminary Report on Patentability in International Appln. No. PCT/US2018/028919, mailed on Oct. 31, 2019, 9 pages.
International Search Report and Written Opinion in International Application No. PCT/US2018/028919, mailed on Oct. 1, 2018, 17 pages.
Invitation to Pay Additional Fees in International Appln. No. PCT/US2018/028919, mailed on Aug. 7, 2018, 3 pages.
Kim et al., "Erratum: Genome-wide analysis reveals specificities of Cpf1 endonucleases in human cells," Nat Biotechnol. 2016, 34(8): 888.
Kim et al., "Genome-wide analysis reveals specificities of Cpf1 endonucleases in human cells," Nat Biotechnol. 2016, 34(8):863-8.
Kim et al., "Increasing the genome-targeting scope and precision of base editing with engineered Cas9-cytidine deaminase fusions," Nat Biotechnol, 2017, 35(4):371-376, 15 pages.
Komor et al., "Improved base excision repair inhibition and bacteriophage Mu Gam protein yields C:G-to-T:A base editors with higher efficiency and product purity," Sci Adv, 2017, 3(8):eaao4774, 9 pages.
Komor et al., "Programmable editing of a target base in genomic DNA without double-stranded DNA cleavage," Nature, 2016, 533(7603):420-4, 25 pages.
Moreno-Mateos et al., "CRISPR-Cpf1 mediates efficient homology-directed repair and temperature-controlled genome editing," Nat Commun., 2017, 8:2024, 9 pages.
Nishida et al., "Targeted nucleotide editing using hybrid prokaryotic and vertebrate adaptive immune systems," Science. 2016, 353(6305): 10 pages.
Rohland and Reich, "Cost-effective, high-throughput DNA sequencing libraries for multiplexed target capture," Genome Res, 2012, 22:939-46.
Shmakov et al., "Discovery and Functional Characterization of Diverse Class 2 CRISPR-Cas Systems," Mol Cell, 2015, 60(3):385-97.
Zetsche et al., "Multiplex gene editing by CRISPR-Cpf1 through autonomous processing of a single crRNA array," Nat Biotechnol., 2017, 35:31-34, 8 pages.
Anders et al., "Structural basis of PAM-dependent target DNA recognition by the Cas9 endonuclease," Nature, Sep. 2014, 513(7519):569-573, 16 pages.
International Search Report and Written Opinion in International Appln. No. PCT/US2016/020756, dated Jul. 26, 2016, 12 pages.
International Search Report and Written Opinion in International Appln. No. PCT/US2016/049147, dated on Dec. 23, 2016, 12 pages.
International Search Report and Written Opinion in International Appln. No. PCT/US2018/036293, dated Nov. 8, 2018, 12 pages.
International Search Report and Written Opinion in International Appln. No. PCT/US2018/047577, dated Jan. 29, 2019, 12 pages.
International Search Report and Written Opinion in International Appln. No. PCT/US2021/014900, dated Jul. 21, 2021, 12 pages.
International Search Report and Written Opinion in International Appln. No. PCT/US2021/014933, dated Jul. 20, 2021, 12 pages.
Nishimasu et al., "Engineered CRISPR-Cas9 nuclease with expanded targeting space," Science, Aug. 2018, 361(6408):1259-1262, 8 pages.
Office Action in Australian Appln. No. 2017302551, dated Oct. 28, 2022, 4 pages.
Protein Data Bank (PDB) [online], "4UN3-Crystal structure of Cas9 bound to PAM-containing DNA target," Sequence Display for the Entities in PDB 4UN3, Jul. 23, 2014, retrieved May 6, 2015, retrieved from URL <http://www.rcsb.org/pdb/explore/explore.do?structureid=4UN3>, 2 pages.
Bae et al., "Cas-OFFinder: a fast and versatile algorithm that searches for potential off-target sites of Cas9 RNA-guided endonucleases," Bioinformatics, 2014, 30: 1473-1475.
Bolukbasi et al., "DNA-binding-domain fusions enhance the targeting range and precision of Cas9," Nat Methods, 2015, 12:1150-1156.
Chen et al., "Enhanced proofreading governs CRISPR-Cas9 targeting accuracy," Nature, Oct. 2017, 550(7676):407-410.
Cong et al., "Multiplex genome engineering using CRISPR/Cas systems," Science, 2013, 339:819-823.
Deltcheva et al., "CRISPR RNA maturation by trans-encoded small RNA and host factor RNase III," Nature, 2011, 471:602-607.
Dong et al., "The crystal structure of Cpf1 in complex with CRISPR RNA," Nature, 2016, 532(7600):522-6.
Doudna and Charpentier, "Genome editing. The new frontier of genome engineering with CRISPR-Cas9," Science, 2014, 346: 1258096 (11 pages).
EP Partial Supplementary European Search Report in European Appln. No. 17835126.8, dated Jan. 2, 2020, 12 pages.
EP Partial Supplementary European Search Report in European Appln. No. 17835126.8, dated Apr. 2, 2020, 9 pages.
Fagerlund et al., "The Cpf1 CRISPR-Cas protein expands genome-editing tools," Genome Biol, 2015, 16:251.
U.S. Appl. No. 62/488,426, filed Apr. 21, 2017, Joung et al.
Fonfara et al., "The CRISPR-associated DNA-cleaving enzyme Cpf1 also processes precursor CRISPR RNA," Nature, 2016, 532(7600):517-21.
Friedland et al., "Characterization of *Staphylococcus aureus* Cas9: a smaller Cas9 for all-in-one adeno-associated virus delivery and paired nickase applications," Genome Biol, 2015, 16: 257 (10 pages).
Frock et al., "Genome-wide detection of DNA double-stranded breaks induced by engineered nucleases," Nat Biotechnol, 2015, 33:179-186.
Fu et al., "Improving CRISPR-Cas nuclease specificity using truncated guide RNAs," Nat Biotechnol, 2014, 32:279-284.
GenBank Accession No. EOS46485.1, "The Genome Sequence of Lachnospiraceae bacterium COE1," May 29, 2013, retrieved on Nov. 7, 2017, https://www.ncbi.nlm.nih.gov/protein/EOS46485, 2 pages.
Hsu et al., "Development and applications of CRISPR-Cas9 for genome engineering," Cell, 2014, 157:1262-1278.
International Preliminary Report on Patentability in International Application No. PCT/US2017/043753, mailed on Feb. 7, 2019, 10 pages.
International Search Report and Written Opinion in International Application No. PCT/US1 7/43753, mailed on Dec. 28, 2017, 18 pages.
Invitation to Pay Additional Fees in International Appln. No. PCT/US2017/043753, dated Oct. 24, 2017, 2 pages.
Jinek et al., "A programmable dual-RNA-guided DNA endonuclease in adaptive bacterial immunity," Science, 2012, 337: 816-821.
Jinek et al., "RNA-programmed genome editing in human cells," Elife, 2013, 2:e00471.
Kim et al., "Digenome-seq: genome-wide profiling of CRISPR-Cas9 off-target effects in human cells," Nat Methods, Mar. 2015, 12: 237-243.
Kleinstiver et al., "Broadening the targeting range of *Staphylococcus aureus* CRISPR-Cas9 by modifying PAM recognition," Nat Biotechnol, 2015, 33: 1293-1298.
Kleinstiver et al., "Engineered CRISPR-Cas9 nucleases with altered specificities," Nature, 2015, 523:481-485.
Kleinstiver et al., "Genome-wide specificities of CRISPR-Cas Cpf1 nucleases in human cells," Nat Biotechnol, 2016, 34(8):869-74.
Kleinstiver et al., "High-fidelity CRISPR-Cas9 nucleases with no detectable genome-wide off-target effects," Nature, 2016, 529:490-495.
Maeder and Gersbach, "Genome-editing Technologies for Gene and Cell Therapy," Mol Ther, 2016, 24: 430-446.
Makarova et al., "An updated evolutionary classification of CRISPR-Cas systems," Nat Rev Microbiol, 2015, 13:722-736.
Mali et al., "RNA-guided human genome engineering via Cas9," Science, 2013, 339: 823-826.

(56) References Cited

OTHER PUBLICATIONS

Office Action in Chinese Appln. No. 201780059001.5, dated Jul. 19, 2022, 21 pages (with English translation).
Reyon et al., "FLASH assembly of TALENs for high-throughput genome editing," Nat Biotechnol, May 2012, 30: 460-465.
Sander and Joung, "CRISPR-Cas systems for editing, regulating and targeting genomes," Nat Biotechnol, 2014, 32:347-355.
Schunder et al., "First indication for a functional CRISPR/Cas system in Francisella tularensis," Int J Med Microbiol, 2013, 303:51-60.
Slaymaker et al., "Rationally engineered Cas9 nucleases with improved specificity," Science, 2016, 351:84-88.
Tak et al., "Inducible, tunable and multiplex human gene regulation using CRISPR-Cpf1-based transcription factors," bioRxiv, 2017, 150656 (21 pages).
Tsai et al., "Dimeric CRISPR RNA-guided FokI nucleases for highly specific genome editing," Nat Biotechnol, 2014, 32:569-576.
Tsai et al., "GUIDE-seq enables genome-wide profiling of off-target cleavage by CRISPR-Cas nucleases," Nat Biotechnol, 2015, 33:187-197.
Tsai et al., "Open-source guideseq software for analysis of GUIDE-seq data," Nat Biotechnol, 2016, 34:483.
Wang et al., "Unbiased detection of off-target cleavage by CRISPR-Cas9 and TALENs using integrase-defective lentiviral vectors," Nat Biotechnol, 2015, 33:175-178.
Wright et al., "Biology and Applications of CRISPR Systems: Harnessing Nature's Toolbox for Genome Engineering," Cell, Jan. 2016, 164: 29-44.
Yamano et al., "Crystal Structure of Cpf1 in Complex with Guide RNA and Target DNA," Cell, 2016, 165(4):949-62.
Yin et al., "Therapeutic genome editing by combined viral and non-viral delivery of CRISPR system components in vivo," Nat Biotechnol, Mar. 2016, 34: 328-333.
Zetsche et al., "Cpf1 Is a Single RNA-Guided Endonuclease of a Class 2 CRISPR-Cas System," Cell, 2015, 163:759-771.
Office Action in Chinese Appln. No. 201780059001.5, dated Nov. 15, 2023, 15 pages (with English translation).
Zhang et al., "Boosting genome editing efficiency in human cells and plants with novel LbCas12a variants," Genome Biol., Apr. 2023, 24(1): 102, 19 pages.
Office Action in Australian Appln. No. 2023208113, mailed on Apr. 16, 2025, 4 pages.

SEQUENCE LISTING

```
<160> NUMBER OF SEQ ID NOS: 198

<210> SEQ ID NO 1
<211> LENGTH: 1246
<212> TYPE: PRT
<213> ORGANISM: Unknown
```

-continued

```
<220> FEATURE:
<223> OTHER INFORMATION: Description of Unknown:
      Lachnospiraceae bacterium polypeptide

<400> SEQUENCE: 1

Met Leu Lys Asn Val Gly Ile Asp Arg Leu Asp Val Glu Lys Gly Arg
1               5                   10                  15

Lys Asn Met Ser Lys Leu Glu Lys Phe Thr Asn Cys Tyr Ser Leu Ser
            20                  25                  30

Lys Thr Leu Arg Phe Lys Ala Ile Pro Val Gly Lys Thr Gln Glu Asn
        35                  40                  45

Ile Asp Asn Lys Arg Leu Leu Val Glu Asp Glu Lys Arg Ala Glu Asp
    50                  55                  60

Tyr Lys Gly Val Lys Lys Leu Leu Asp Arg Tyr Tyr Leu Ser Phe Ile
65                  70                  75                  80

Asn Asp Val Leu His Ser Ile Lys Leu Lys Asn Leu Asn Asn Tyr Ile
                85                  90                  95

Ser Leu Phe Arg Lys Lys Thr Arg Thr Glu Lys Glu Asn Lys Glu Leu
            100                 105                 110

Glu Asn Leu Glu Ile Asn Leu Arg Lys Glu Ile Ala Lys Ala Phe Lys
        115                 120                 125

Gly Asn Glu Gly Tyr Lys Ser Leu Phe Lys Lys Asp Ile Ile Glu Thr
    130                 135                 140

Ile Leu Pro Glu Phe Leu Asp Asp Lys Asp Glu Ile Ala Leu Val Asn
145                 150                 155                 160

Ser Phe Asn Gly Phe Thr Thr Ala Phe Thr Gly Phe Phe Asp Asn Arg
                165                 170                 175

Glu Asn Met Phe Ser Glu Glu Ala Lys Ser Thr Ser Ile Ala Phe Arg
            180                 185                 190

Cys Ile Asn Glu Asn Leu Thr Arg Tyr Ile Ser Asn Met Asp Ile Phe
        195                 200                 205

Glu Lys Val Asp Ala Ile Phe Asp Lys His Glu Val Gln Glu Ile Lys
    210                 215                 220

Glu Lys Ile Leu Asn Ser Asp Tyr Asp Val Glu Asp Phe Phe Glu Gly
225                 230                 235                 240

Glu Phe Phe Asn Phe Val Leu Thr Gln Glu Gly Ile Asp Val Tyr Asn
                245                 250                 255

Ala Ile Ile Gly Gly Phe Val Thr Glu Ser Gly Glu Lys Ile Lys Gly
            260                 265                 270

Leu Asn Glu Tyr Ile Asn Leu Tyr Asn Gln Lys Thr Lys Gln Lys Leu
        275                 280                 285

Pro Lys Phe Lys Pro Leu Tyr Lys Gln Val Leu Ser Asp Arg Glu Ser
    290                 295                 300

Leu Ser Phe Tyr Gly Glu Gly Tyr Thr Ser Asp Glu Glu Val Leu Glu
305                 310                 315                 320

Val Phe Arg Asn Thr Leu Asn Lys Asn Ser Glu Ile Phe Ser Ser Ile
                325                 330                 335

Lys Lys Leu Glu Lys Leu Phe Lys Asn Phe Asp Glu Tyr Ser Ser Ala
            340                 345                 350

Gly Ile Phe Val Lys Asn Gly Pro Ala Ile Ser Thr Ile Ser Lys Asp
        355                 360                 365

Ile Phe Gly Glu Trp Asn Val Ile Arg Asp Lys Trp Asn Ala Glu Tyr
    370                 375                 380

Asp Asp Ile His Leu Lys Lys Lys Ala Val Val Thr Glu Lys Tyr Glu
```

-continued

```
385                 390                 395                 400

Asp Asp Arg Arg Lys Ser Phe Lys Lys Ile Gly Ser Phe Ser Leu Glu
                405                 410                 415

Gln Leu Gln Glu Tyr Ala Asp Ala Asp Leu Ser Val Val Glu Lys Leu
            420                 425                 430

Lys Glu Ile Ile Ile Gln Lys Val Asp Glu Ile Tyr Lys Val Tyr Gly
        435                 440                 445

Ser Ser Glu Lys Leu Phe Asp Ala Asp Phe Val Leu Glu Lys Ser Leu
    450                 455                 460

Lys Lys Asn Asp Ala Val Val Ala Ile Met Lys Asp Leu Leu Asp Ser
465                 470                 475                 480

Val Lys Ser Phe Glu Asn Tyr Ile Lys Ala Phe Phe Gly Glu Gly Lys
                485                 490                 495

Glu Thr Asn Arg Asp Glu Ser Phe Tyr Gly Asp Phe Val Leu Ala Tyr
            500                 505                 510

Asp Ile Leu Leu Lys Val Asp His Ile Tyr Asp Ala Ile Arg Asn Tyr
        515                 520                 525

Val Thr Gln Lys Pro Tyr Ser Lys Asp Lys Phe Lys Leu Tyr Phe Gln
    530                 535                 540

Asn Pro Gln Phe Met Gly Gly Trp Asp Lys Asp Lys Glu Thr Asp Tyr
545                 550                 555                 560

Arg Ala Thr Ile Leu Arg Tyr Gly Ser Lys Tyr Tyr Leu Ala Ile Met
                565                 570                 575

Asp Lys Lys Tyr Ala Lys Cys Leu Gln Lys Ile Asp Lys Asp Asp Val
            580                 585                 590

Asn Gly Asn Tyr Glu Lys Ile Asn Tyr Lys Leu Leu Pro Gly Pro Asn
        595                 600                 605

Lys Met Leu Pro Lys Val Phe Phe Ser Lys Lys Trp Met Ala Tyr Tyr
    610                 615                 620

Asn Pro Ser Glu Asp Ile Gln Lys Ile Tyr Lys Asn Gly Thr Phe Lys
625                 630                 635                 640

Lys Gly Asp Met Phe Asn Leu Asn Asp Cys His Lys Leu Ile Asp Phe
                645                 650                 655

Phe Lys Asp Ser Ile Ser Arg Tyr Pro Lys Trp Ser Asn Ala Tyr Asp
            660                 665                 670

Phe Asn Phe Ser Glu Thr Glu Lys Tyr Lys Asp Ile Ala Gly Phe Tyr
        675                 680                 685

Arg Glu Val Glu Glu Gln Gly Tyr Lys Val Ser Phe Glu Ser Ala Ser
    690                 695                 700

Lys Lys Glu Val Asp Lys Leu Val Glu Glu Gly Lys Leu Tyr Met Phe
705                 710                 715                 720

Gln Ile Tyr Asn Lys Asp Phe Ser Asp Lys Ser His Gly Thr Pro Asn
                725                 730                 735

Leu His Thr Met Tyr Phe Lys Leu Leu Phe Asp Glu Asn Asn His Gly
            740                 745                 750

Gln Ile Arg Leu Ser Gly Gly Ala Glu Leu Phe Met Arg Arg Ala Ser
        755                 760                 765

Leu Lys Lys Glu Glu Leu Val Val His Pro Ala Asn Ser Pro Ile Ala
    770                 775                 780

Asn Lys Asn Pro Asp Asn Pro Lys Lys Thr Thr Thr Leu Ser Tyr Asp
785                 790                 795                 800

Val Tyr Lys Asp Lys Arg Phe Ser Glu Asp Gln Tyr Glu Leu His Ile
                805                 810                 815
```

-continued

```
Pro Ile Ala Ile Asn Lys Cys Pro Lys Asn Ile Phe Lys Ile Asn Thr
            820                 825                 830

Glu Val Arg Val Leu Leu Lys His Asp Asp Asn Pro Tyr Val Ile Gly
        835                 840                 845

Ile Asp Arg Gly Glu Arg Asn Leu Leu Tyr Ile Val Val Val Asp Gly
    850                 855                 860

Lys Gly Asn Ile Val Glu Gln Tyr Ser Leu Asn Glu Ile Ile Asn Asn
865                 870                 875                 880

Phe Asn Gly Ile Arg Ile Lys Thr Asp Tyr His Ser Leu Leu Asp Lys
                885                 890                 895

Lys Glu Lys Glu Arg Phe Glu Ala Arg Gln Asn Trp Thr Ser Ile Glu
            900                 905                 910

Asn Ile Lys Glu Leu Lys Ala Gly Tyr Ile Ser Gln Val Val His Lys
        915                 920                 925

Ile Cys Glu Leu Val Glu Lys Tyr Asp Ala Val Ile Ala Leu Glu Asp
    930                 935                 940

Leu Asn Ser Gly Phe Lys Asn Ser Arg Val Lys Val Glu Lys Gln Val
945                 950                 955                 960

Tyr Gln Lys Phe Glu Lys Met Leu Ile Asp Lys Leu Asn Tyr Met Val
                965                 970                 975

Asp Lys Lys Ser Asn Pro Cys Ala Thr Gly Gly Ala Leu Lys Gly Tyr
            980                 985                 990

Gln Ile Thr Asn Lys Phe Glu Ser  Phe Lys Ser Met Ser  Thr Gln Asn
        995                 1000                1005

Gly Phe  Ile Phe Tyr Ile Pro  Ala Trp Leu Thr Ser  Lys Ile Asp
    1010                1015                1020

Pro Ser  Thr Gly Phe Val Asn  Leu Leu Lys Thr Lys  Tyr Thr Ser
    1025                1030                1035

Ile Ala  Asp Ser Lys Lys Phe  Ile Ser Ser Phe Asp  Arg Ile Met
    1040                1045                1050

Tyr Val  Pro Glu Glu Asp Leu  Phe Glu Phe Ala Leu  Asp Tyr Lys
    1055                1060                1065

Asn Phe  Ser Arg Thr Asp Ala  Asp Tyr Ile Lys Lys  Trp Lys Leu
    1070                1075                1080

Tyr Ser  Tyr Gly Asn Arg Ile  Arg Ile Phe Arg Asn  Pro Lys Lys
    1085                1090                1095

Asn Asn  Val Phe Asp Trp Glu  Glu Val Cys Leu Thr  Ser Ala Tyr
    1100                1105                1110

Lys Glu  Leu Phe Asn Lys Tyr  Gly Ile Asn Tyr Gln  Gln Gly Asp
    1115                1120                1125

Ile Arg  Ala Leu Leu Cys Glu  Gln Ser Asp Lys Ala  Phe Tyr Ser
    1130                1135                1140

Ser Phe  Met Ala Leu Met Ser  Leu Met Leu Gln Met  Arg Asn Ser
    1145                1150                1155

Ile Thr  Gly Arg Thr Asp Val  Asp Phe Leu Ile Ser  Pro Val Lys
    1160                1165                1170

Asn Ser  Asp Gly Ile Phe Tyr  Asp Ser Arg Asn Tyr  Glu Ala Gln
    1175                1180                1185

Glu Asn  Ala Ile Leu Pro Lys  Asn Ala Asp Ala Asn  Gly Ala Tyr
    1190                1195                1200

Asn Ile  Ala Arg Lys Val Leu  Trp Ala Ile Gly Gln  Phe Lys Lys
    1205                1210                1215
```

-continued

```
Ala Glu  Asp Glu Lys Leu Asp  Lys Val Lys Ile Ala  Ile Ser Asn
    1220                 1225                 1230

Lys Glu  Trp Leu Glu Tyr Ala  Gln Thr Ser Val Lys  His
    1235                 1240                 1245


<210> SEQ ID NO 2
<211> LENGTH: 1307
<212> TYPE: PRT
<213> ORGANISM: Acidaminococcus sp.

<400> SEQUENCE: 2

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350
```

-continued

```
Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765
```

-continued

```
Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys  Ser Lys Arg Thr Gly  Ile Ala Glu
        995                 1000                1005

Lys Ala  Val Tyr Gln Gln Phe  Glu Lys Met Leu Ile  Asp Lys Leu
    1010                1015                1020

Asn Cys  Leu Val Leu Lys Asp  Tyr Pro Ala Glu Lys  Val Gly Gly
    1025                1030                1035

Val Leu  Asn Pro Tyr Gln Leu  Thr Asp Gln Phe Thr  Ser Phe Ala
    1040                1045                1050

Lys Met  Gly Thr Gln Ser Gly  Phe Leu Phe Tyr Val  Pro Ala Pro
    1055                1060                1065

Tyr Thr  Ser Lys Ile Asp Pro  Leu Thr Gly Phe Val  Asp Pro Phe
    1070                1075                1080

Val Trp  Lys Thr Ile Lys Asn  His Glu Ser Arg Lys  His Phe Leu
    1085                1090                1095

Glu Gly  Phe Asp Phe Leu His  Tyr Asp Val Lys Thr  Gly Asp Phe
    1100                1105                1110

Ile Leu  His Phe Lys Met Asn  Arg Asn Leu Ser Phe  Gln Arg Gly
    1115                1120                1125

Leu Pro  Gly Phe Met Pro Ala  Trp Asp Ile Val Phe  Glu Lys Asn
    1130                1135                1140

Glu Thr  Gln Phe Asp Ala Lys  Gly Thr Pro Phe Ile  Ala Gly Lys
    1145                1150                1155

Arg Ile  Val Pro Val Ile Glu  Asn His Arg Phe Thr  Gly Arg Tyr
    1160                1165                1170

Arg Asp  Leu Tyr Pro Ala Asn  Glu Leu Ile Ala Leu  Leu Glu Glu
```

-continued

```
    1175                1180                1185

Lys Gly  Ile Val Phe Arg Asp  Gly Ser Asn Ile Leu  Pro Lys Leu
    1190                1195                1200

Leu Glu  Asn Asp Asp Ser His  Ala Ile Asp Thr Met  Val Ala Leu
    1205                1210                1215

Ile Arg  Ser Val Leu Gln Met  Arg Asn Ser Asn Ala  Ala Thr Gly
    1220                1225                1230

Glu Asp  Tyr Ile Asn Ser Pro  Val Arg Asp Leu Asn  Gly Val Cys
    1235                1240                1245

Phe Asp  Ser Arg Phe Gln Asn  Pro Glu Trp Pro Met  Asp Ala Asp
    1250                1255                1260

Ala Asn  Gly Ala Tyr His Ile  Ala Leu Lys Gly Gln  Leu Leu Leu
    1265                1270                1275

Asn His  Leu Lys Glu Ser Lys  Asp Leu Lys Leu Gln  Asn Gly Ile
    1280                1285                1290

Ser Asn  Gln Asp Trp Leu Ala  Tyr Ile Gln Glu Leu  Arg Asn
    1295                1300                1305


<210> SEQ ID NO 3
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

aaaaggccgg cggccacgaa aaaggccggc caggcaaaaa agaaaaag                  48


<210> SEQ ID NO 4
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

tacccatacg atgttccaga ttacgcttat ccctacgacg tgcctgatta tgcataccca     60

tatgatgtcc ccgactatgc c                                               81


<210> SEQ ID NO 5
<211> LENGTH: 4059
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

atgacacagt tcgagggctt taccaacctg tatcaggtga gcaagacact gcggtttgag     60

ctgatcccac agggcaagac cctgaagcac atccaggagc agggcttcat cgaggaggac    120

aaggcccgca atgatcacta caaggagctg aagcccatca tcgatcggat ctacaagacc    180

tatgccgacc agtgcctgca gctggtgcag ctggattggg agaacctgag cgccgccatc    240

gactcctata gaaaggagaa aaccgaggag acaaggaacg ccctgatcga ggagcaggcc    300

acatatcgca atgccatcca cgactacttc atcggccgga cagacaacct gaccgatgcc    360

atcaataaga gacacgccga gatctacaag ggcctgttca aggccgagct gtttaatggc    420
```

-continued

```
aaggtgctga agcagctggg caccgtgacc acaaccgagc acgagaacgc cctgctgcgg    480
agcttcgaca agtttacaac ctacttctcc ggcttttatg agaacaggaa gaacgtgttc    540
agcgccgagg atatcagcac agccatccca caccgcatcg tgcaggacaa cttccccaag    600
tttaaggaga attgtcacat cttcacacgc ctgatcaccg ccgtgcccag cctgcgggag    660
cactttgaga acgtgaagaa ggccatcggc atcttcgtga gcacctccat cgaggaggtg    720
ttttccttcc ctttttataa ccagctgctg acacagaccc agatcgacct gtataaccag    780
ctgctgggag gaatctctcg ggaggcaggc accgagaaga tcaagggcct gaacgaggtg    840
ctgaatctgg ccatccagaa gaatgatgag acagcccaca tcatcgcctc cctgccacac    900
agattcatcc ccctgtttaa gcagatcctg tccgatagga acaccctgtc tttcatcctg    960
gaggagttta agagcgacga ggaagtgatc cagtccttct gcaagtacaa gacactgctg   1020
agaaacgaga acgtgctgga gacagccgag gccctgttta acgagctgaa cagcatcgac   1080
ctgacacaca tcttcatcag ccacaagaag ctggagacaa tcagcagcgc cctgtgcgac   1140
cactgggata cactgaggaa tgccctgtat gagcggagaa tctccgagct gacaggcaag   1200
atcaccaagt ctgccaagga gaaggtgcag cgcagcctga agcacgagga tatcaacctg   1260
caggagatca tctctgccgc aggcaaggag ctgagcgagg ccttcaagca gaaaaccagc   1320
gagatcctgt cccacgcaca cgccgccctg gatcagccac tgcctacaac cctgaagaag   1380
caggaggaga aggagatcct gaagtctcag ctggacagcc tgctgggcct gtaccacctg   1440
ctggactggt ttgccgtgga tgagtccaac gaggtggacc ccgagttctc tgcccggctg   1500
accggcatca agctggagat ggagccttct ctgagcttct acaacaaggc cagaaattat   1560
gccaccaaga agccctactc cgtggagaag ttcaagctga actttcagat gcctacactg   1620
gcctctggct gggacgtgaa taaggagaag aacaatggcg ccatcctgtt tgtgaagaac   1680
ggcctgtact atctgggcat catgccaaag cagaagggca ggtataaggc cctgagcttc   1740
gagcccacag agaaaaccag cgagggcttt gataagatgt actatgacta cttccctgat   1800
gccgccaaga tgatcccaaa gtgcagcacc cagctgaagg ccgtgacagc ccactttcag   1860
acccacacaa cccccatcct gctgtccaac aatttcatcg agcctctgga gatcacaaag   1920
gagatctacg acctgaacaa tcctgagaag gagccaaaga agtttcagac agcctacgcc   1980
aagaaaaccg gcgaccagaa gggctacaga gaggccctgt gcaagtggat cgacttcaca   2040
agggattttc tgtccaagta taccaagaca acctctatcg atctgtctag cctgcggcca   2100
tcctctcagt ataaggacct gggcgagtac tatgccgagc tgaatcccct gctgtaccac   2160
atcagcttcc agagaatcgc cgagaaggag atcatggatg ccgtggagac aggcaagctg   2220
tacctgttcc agatctataa caaggacttt gccaagggcc accacggcaa gcctaatctg   2280
cacacactgt attggaccgg cctgttttct ccagagaacc tggccaagac aagcatcaag   2340
ctgaatggcc aggccgagct gttctaccgc cctaagtcca ggatgaagag gatggcacac   2400
cggctgggag agaagatgct gaacaagaag ctgaaggatc agaaaacccc aatccccgac   2460
accctgtacc aggagctgta cgactatgtg aatcacagac tgtcccacga cctgtctgat   2520
gaggccaggg ccctgctgcc caacgtgatc accaaggagg tgtctcacga gatcatcaag   2580
gataggcgct ttaccagcga caagttcttt ttccacgtgc ctatcacact gaactatcag   2640
gccgccaatt ccccatctaa gttcaaccag agggtgaatg cctacctgaa ggagcacccc   2700
gagacaccta tcatcggcat cgatcggggc gagagaaacc tgatctatat cacagtgatc   2760
gactccaccg gcaagatcct ggagcagcgg agcctgaaca ccatccagca gtttgattac   2820
```

-continued

```
cagaagaagc tggacaacag ggagaaggag agggtggcag caaggcaggc ctggtctgtg      2880

gtgggcacaa tcaaggatct gaagcagggc tatctgagcc aggtcatcca cgagatcgtg      2940

gacctgatga tccactacca ggccgtggtg gtgctggaga acctgaattt cggctttaag      3000

agcaagagga ccggcatcgc cgagaaggcc gtgtaccagc agttcgagaa gatgctgatc      3060

gataagctga attgcctggt gctgaaggac tatccagcag agaaagtggg aggcgtgctg      3120

aacccatacc agctgacaga ccagttcacc tcctttgcca agatgggcac ccagtctggc      3180

ttcctgtttt acgtgcctgc cccatataca tctaagatcg atcccctgac cggcttcgtg      3240

gaccccttcg tgtggaaaac catcaagaat cacgagagcc gcaagcactt cctggagggc      3300

ttcgactttc tgcactacga cgtgaaaacc ggcgacttca tcctgcactt taagatgaac      3360

agaaatctgt ccttccagag gggcctgccc ggctttatgc ctgcatggga tatcgtgttc      3420

gagaagaacg agacacagtt tgacgccaag ggcacccctt tcatcgccgg caagagaatc      3480

gtgccagtga tcgagaatca cagattcacc ggcagatacc gggacctgta tcctgccaac      3540

gagctgatcg ccctgctgga ggagaagggc atcgtgttca gggatggctc caacatcctg      3600

ccaaagctgc tggagaatga cgattctcac gccatcgaca ccatggtggc cctgatccgc      3660

agcgtgctgc agatgcggaa ctccaatgcc gccacaggcg aggactatat caacagcccc      3720

gtgcgcgatc tgaatggcgt gtgcttcgac tcccggtttc agaacccaga gtggcccatg      3780

gacgccgatg ccaatggcgc ctaccacatc gccctgaagg gccagctgct gctgaatcac      3840

ctgaaggaga gcaaggatct gaagctgcag aacggcatct ccaatcagga ctggctggcc      3900

tacatccagg agctgcgcaa caaaaggccg gcggccacga aaaaggccgg ccaggcaaaa      3960

aagaaaaagg gatcctaccc atacgatgtt ccagattacg cttatcccta cgacgtgcct      4020

gattatgcat acccatatga tgtccccgac tatgcctaa                              4059
```

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 6

Lys Arg Pro Ala Ala Thr Lys Lys Ala Gly Gln Ala Lys Lys Lys Lys
1               5                   10                  15

Gly Ser

<210> SEQ ID NO 7
<211> LENGTH: 27
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 7

Tyr Pro Tyr Asp Val Pro Asp Tyr Ala Tyr Pro Tyr Asp Val Pro Asp
1               5                   10                  15

Tyr Ala Tyr Pro Tyr Asp Val Pro Asp Tyr Ala
            20                  25

<210> SEQ ID NO 8
<211> LENGTH: 1352

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 8

```
Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380
```

-continued

```
Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800
```

-continued

```
Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys  Ser Lys Arg Thr Gly  Ile Ala Glu
        995                 1000                1005

Lys Ala  Val Tyr Gln Gln Phe  Glu Lys Met Leu Ile  Asp Lys Leu
    1010                 1015                 1020

Asn Cys  Leu Val Leu Lys Asp  Tyr Pro Ala Glu Lys  Val Gly Gly
    1025                 1030                 1035

Val Leu  Asn Pro Tyr Gln Leu  Thr Asp Gln Phe Thr  Ser Phe Ala
    1040                 1045                 1050

Lys Met  Gly Thr Gln Ser Gly  Phe Leu Phe Tyr Val  Pro Ala Pro
    1055                 1060                 1065

Tyr Thr  Ser Lys Ile Asp Pro  Leu Thr Gly Phe Val  Asp Pro Phe
    1070                 1075                 1080

Val Trp  Lys Thr Ile Lys Asn  His Glu Ser Arg Lys  His Phe Leu
    1085                 1090                 1095

Glu Gly  Phe Asp Phe Leu His  Tyr Asp Val Lys Thr  Gly Asp Phe
    1100                 1105                 1110

Ile Leu  His Phe Lys Met Asn  Arg Asn Leu Ser Phe  Gln Arg Gly
    1115                 1120                 1125

Leu Pro  Gly Phe Met Pro Ala  Trp Asp Ile Val Phe  Glu Lys Asn
    1130                 1135                 1140

Glu Thr  Gln Phe Asp Ala Lys  Gly Thr Pro Phe Ile  Ala Gly Lys
    1145                 1150                 1155

Arg Ile  Val Pro Val Ile Glu  Asn His Arg Phe Thr  Gly Arg Tyr
    1160                 1165                 1170

Arg Asp  Leu Tyr Pro Ala Asn  Glu Leu Ile Ala Leu  Leu Glu Glu
    1175                 1180                 1185

Lys Gly  Ile Val Phe Arg Asp  Gly Ser Asn Ile Leu  Pro Lys Leu
    1190                 1195                 1200

Leu Glu  Asn Asp Asp Ser His  Ala Ile Asp Thr Met  Val Ala Leu
```

-continued

```
    1205                 1210                 1215

Ile Arg  Ser Val Leu Gln Met  Arg Asn Ser Asn Ala  Ala Thr Gly
    1220                 1225                 1230

Glu Asp  Tyr Ile Asn Ser Pro  Val Arg Asp Leu Asn  Gly Val Cys
    1235                 1240                 1245

Phe Asp  Ser Arg Phe Gln Asn  Pro Glu Trp Pro Met  Asp Ala Asp
    1250                 1255                 1260

Ala Asn  Gly Ala Tyr His Ile  Ala Leu Lys Gly Gln  Leu Leu Leu
    1265                 1270                 1275

Asn His  Leu Lys Glu Ser Lys  Asp Leu Lys Leu Gln  Asn Gly Ile
    1280                 1285                 1290

Ser Asn  Gln Asp Trp Leu Ala  Tyr Ile Gln Glu Leu  Arg Asn Lys
    1295                 1300                 1305

Arg Pro  Ala Ala Thr Lys Lys  Ala Gly Gln Ala Lys  Lys Lys Lys
    1310                 1315                 1320

Gly Ser  Tyr Pro Tyr Asp Val  Pro Asp Tyr Ala Tyr  Pro Tyr Asp
    1325                 1330                 1335

Val Pro  Asp Tyr Ala Tyr Pro  Tyr Asp Val Pro Asp  Tyr Ala
    1340                 1345                 1350
```

<210> SEQ ID NO 9
<211> LENGTH: 3822
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
atgagcaagc tggagaagtt tacaaactgc tactccctgt ctaagaccct gaggttcaag     60

gccatccctg tgggcaagac ccaggagaac atcgacaata agcggctgct ggtggaggac    120

gagaagagag ccgaggatta taagggcgtg aagaagctgc tggatcgcta ctatctgtct    180

tttatcaacg acgtgctgca cagcatcaag ctgaagaatc tgaacaatta catcagcctg    240

ttccggaaga aaaccagaac cgagaaggag aataaggagc tggagaacct ggagatcaat    300

ctgcggaagg agatcgccaa ggccttcaag ggcaacgagg gctacaagtc cctgtttaag    360

aaggatatca tcgagacaat cctgccagag ttcctggacg ataaggacga gatcgccctg    420

gtgaacagct tcaatggctt taccacagcc ttcaccggct tctttgataa cagagagaat    480

atgttttccg aggaggccaa gagcacatcc atcgccttca ggtgtatcaa cgagaatctg    540

acccgctaca tctctaatat ggacatcttc gagaaggtgg acgccatctt tgataagcac    600

gaggtgcagg agatcaagga gaagatcctg aacagcgact atgatgtgga ggatttcttt    660

gagggcgagt tctttaactt tgtgctgaca caggagggca tcgacgtgta taacgccatc    720

atcggcggct tcgtgaccga gagcggcgag aagatcaagg gcctgaacga gtacatcaac    780

ctgtataatc agaaaaccaa gcagaagctg cctaagttta agccactgta taagcaggtg    840

ctgagcgatc gggagtctct gagcttctac ggcgagggct atacatccga tgaggaggtg    900

ctggaggtgt ttagaaacac cctgaacaag aacagcgaga tcttcagctc catcaagaag    960

ctggagaagc tgttcaagaa ttttgacgag tactctagcg ccggcatctt tgtgaagaac   1020

ggccccgcca tcagcacaat ctccaaggat atcttcggcg agtggaacgt gatccgggac   1080

aagtggaatg ccgagtatga cgatatccac ctgaagaaga aggccgtggt gaccgagaag   1140

tacgaggacg atcggagaaa gtccttcaag aagatcggct ccttttctct ggagcagctg   1200
```

-continued

```
caggagtacg ccgacgccga tctgtctgtg gtggagaagc tgaaggagat catcatccag   1260
aaggtggatg agatctacaa ggtgtatggc tcctctgaga agctgttcga cgccgatttt   1320
gtgctggaga agagcctgaa gaagaacgac gccgtggtgg ccatcatgaa ggacctgctg   1380
gattctgtga agagcttcga gaattacatc aaggccttct ttggcgaggg caaggagaca   1440
aacagggacg agtccttcta tggcgatttt gtgctggcct acgacatcct gctgaaggtg   1500
gaccacatct acgatgccat ccgcaattat gtgacccaga agccctactc taaggataag   1560
ttcaagctgt attttcagaa ccctcagttc atgggcggct gggacaagga taaggagaca   1620
gactatcggg ccaccatcct gagatacggc tccaagtact atctggccat catggataag   1680
aagtacgcca agtgcctgca gaagatcgac aaggacgatg tgaacggcaa ttacgagaag   1740
atcaactata agctgctgcc cggccctaat aagatgctgc caaaggtgtt cttttctaag   1800
aagtggatgg cctactataa ccccagcgag gacatccaga agatctacaa gaatggcaca   1860
ttcaagaagg gcgatatgtt taacctgaat gactgtcaca agctgatcga cttctttaag   1920
gatagcatct cccggtatcc aaagtggtcc aatgcctacg atttcaactt ttctgagaca   1980
gagaagtata aggacatcgc cggcttttac agagaggtgg aggagcaggg ctataaggtg   2040
agcttcgagt ctgccagcaa gaaggaggtg gataagctgg tggaggaggg caagctgtat   2100
atgttccaga tctataacaa ggacttttcc gataagtctc acggcacacc caatctgcac   2160
accatgtact tcaagctgct gtttgacgag aacaatcacg gacagatcag gctgagcgga   2220
ggagcagagc tgttcatgag gcgcgcctcc ctgaagaagg aggagctggt ggtgcaccca   2280
gccaactccc ctatcgccaa caagaatcca gataatccca agaaaaccac aaccctgtcc   2340
tacgacgtgt ataaggataa gaggttttct gaggaccagt acgagctgca catcccaatc   2400
gccatcaata agtgccccaa gaacatcttc aagatcaata cagaggtgcg cgtgctgctg   2460
aagcacgacg ataaccccta tgtgatcggc atcgataggg gcgagcgcaa tctgctgtat   2520
atcgtggtgg tggacggcaa gggcaacatc gtggagcagt attccctgaa cgagatcatc   2580
aacaacttca acggcatcag gatcaagaca gattaccact ctctgctgga caagaaggag   2640
aaggagaggt tcgaggcccg ccagaactgg acctccatcg agaatatcaa ggagctgaag   2700
gccggctata tctctcaggt ggtgcacaag atctgcgagc tggtggagaa gtacgatgcc   2760
gtgatcgccc tggaggacct gaactctggc tttaagaata gccgcgtgaa ggtggagaag   2820
caggtgtatc agaagttcga gaagatgctg atcgataagc tgaactacat ggtggacaag   2880
aagtctaatc cttgtgcaac aggcggcgcc ctgaagggct atcagatcac caataagttc   2940
gagagcttta agtccatgtc tacccagaac ggcttcatct tttacatccc tgcctggctg   3000
acatccaaga tcgatccatc taccggcttt gtgaacctgc tgaaaaccaa gtataccagc   3060
atcgccgatt ccaagaagtt catcagctcc tttgacagga tcatgtacgt gcccgaggag   3120
gatctgttcg agtttgccct ggactataag aacttctctc gcacagacgc cgattacatc   3180
aagaagtgga agctgtactc ctacggcaac cggatcagaa tcttccggaa tcctaagaag   3240
aacaacgtgt tcgactggga ggaggtgtgc ctgaccagcg cctataagga gctgttcaac   3300
aagtacggca tcaattatca gcagggcgat atcagagccc tgctgtgcga gcagtccgac   3360
aaggccttct actctagctt tatggccctg atgagcctga tgctgcagat gcggaacagc   3420
atcacaggcc gcaccgacgt ggattttctg atcagccctg tgaagaactc cgacggcatc   3480
ttctacgata gccggaacta tgaggcccag gagaatgcca tcctgccaaa gaacgccgac   3540
```

```
gccaatggcg cctataacat cgccagaaag gtgctgtggg ccatcggcca gttcaagaag   3600

gccgaggacg agaagctgga taaggtgaag atcgccatct ctaacaagga gtggctggag   3660

tacgcccaga ccagcgtgaa gcacaaaagg ccggcggcca cgaaaaaggc cggccaggca   3720

aaaaagaaaa agggatccta cccatacgat gttccagatt acgcttatcc ctacgacgtg   3780

cctgattatg catacccata tgatgtcccc gactatgcct aa                      3822


<210> SEQ ID NO 10
<211> LENGTH: 1273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
```

-continued 305 310 315 320

Leu Glu Lys Leu Phe Lys Asn Phe Asp Glu Tyr Ser Ser Ala Gly Ile
325 330 335

Phe Val Lys Asn Gly Pro Ala Ile Ser Thr Ile Ser Lys Asp Ile Phe
340 345 350

Gly Glu Trp Asn Val Ile Arg Asp Lys Trp Asn Ala Glu Tyr Asp Asp
355 360 365

Ile His Leu Lys Lys Lys Ala Val Val Thr Glu Lys Tyr Glu Asp Asp
370 375 380

Arg Arg Lys Ser Phe Lys Lys Ile Gly Ser Phe Ser Leu Glu Gln Leu
385 390 395 400

Gln Glu Tyr Ala Asp Ala Asp Leu Ser Val Val Glu Lys Leu Lys Glu
405 410 415

Ile Ile Ile Gln Lys Val Asp Glu Ile Tyr Lys Val Tyr Gly Ser Ser
420 425 430

Glu Lys Leu Phe Asp Ala Asp Phe Val Leu Glu Lys Ser Leu Lys Lys
435 440 445

Asn Asp Ala Val Val Ala Ile Met Lys Asp Leu Leu Asp Ser Val Lys
450 455 460

Ser Phe Glu Asn Tyr Ile Lys Ala Phe Phe Gly Glu Gly Lys Glu Thr
465 470 475 480

Asn Arg Asp Glu Ser Phe Tyr Gly Asp Phe Val Leu Ala Tyr Asp Ile
485 490 495

Leu Leu Lys Val Asp His Ile Tyr Asp Ala Ile Arg Asn Tyr Val Thr
500 505 510

Gln Lys Pro Tyr Ser Lys Asp Lys Phe Lys Leu Tyr Phe Gln Asn Pro
515 520 525

Gln Phe Met Gly Gly Trp Asp Lys Asp Lys Glu Thr Asp Tyr Arg Ala
530 535 540

Thr Ile Leu Arg Tyr Gly Ser Lys Tyr Tyr Leu Ala Ile Met Asp Lys
545 550 555 560

Lys Tyr Ala Lys Cys Leu Gln Lys Ile Asp Lys Asp Asp Val Asn Gly
565 570 575

Asn Tyr Glu Lys Ile Asn Tyr Lys Leu Leu Pro Gly Pro Asn Lys Met
580 585 590

Leu Pro Lys Val Phe Phe Ser Lys Lys Trp Met Ala Tyr Tyr Asn Pro
595 600 605

Ser Glu Asp Ile Gln Lys Ile Tyr Lys Asn Gly Thr Phe Lys Lys Gly
610 615 620

Asp Met Phe Asn Leu Asn Asp Cys His Lys Leu Ile Asp Phe Phe Lys
625 630 635 640

Asp Ser Ile Ser Arg Tyr Pro Lys Trp Ser Asn Ala Tyr Asp Phe Asn
645 650 655

Phe Ser Glu Thr Glu Lys Tyr Lys Asp Ile Ala Gly Phe Tyr Arg Glu
660 665 670

Val Glu Glu Gln Gly Tyr Lys Val Ser Phe Glu Ser Ala Ser Lys Lys
675 680 685

Glu Val Asp Lys Leu Val Glu Glu Gly Lys Leu Tyr Met Phe Gln Ile
690 695 700

Tyr Asn Lys Asp Phe Ser Asp Lys Ser His Gly Thr Pro Asn Leu His
705 710 715 720

Thr Met Tyr Phe Lys Leu Leu Phe Asp Glu Asn Asn His Gly Gln Ile
725 730 735

-continued

```
Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Val Asp Gly Lys Gly
        835                 840                 845

Asn Ile Val Glu Gln Tyr Ser Leu Asn Glu Ile Ile Asn Asn Phe Asn
    850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Glu Asp Leu Asn
        915                 920                 925

Ser Gly Phe Lys Asn Ser Arg Val Lys Val Glu Lys Gln Val Tyr Gln
    930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu  Thr Ser Lys Ile Asp  Pro Ser Thr
        995                 1000                1005

Gly Phe  Val Asn Leu Leu Lys  Thr Lys Tyr Thr Ser  Ile Ala Asp
    1010                1015                1020

Ser Lys  Lys Phe Ile Ser Ser  Phe Asp Arg Ile Met  Tyr Val Pro
    1025                1030                1035

Glu Glu  Asp Leu Phe Glu Phe  Ala Leu Asp Tyr Lys  Asn Phe Ser
    1040                1045                1050

Arg Thr  Asp Ala Asp Tyr Ile  Lys Lys Trp Lys Leu  Tyr Ser Tyr
    1055                1060                1065

Gly Asn  Arg Ile Arg Ile Phe  Arg Asn Pro Lys Lys  Asn Asn Val
    1070                1075                1080

Phe Asp  Trp Glu Glu Val Cys  Leu Thr Ser Ala Tyr  Lys Glu Leu
    1085                1090                1095

Phe Asn  Lys Tyr Gly Ile Asn  Tyr Gln Gln Gly Asp  Ile Arg Ala
    1100                1105                1110

Leu Leu  Cys Glu Gln Ser Asp  Lys Ala Phe Tyr Ser  Ser Phe Met
    1115                1120                1125

Ala Leu  Met Ser Leu Met Leu  Gln Met Arg Asn Ser  Ile Thr Gly
    1130                1135                1140
```

-continued

```
Arg Thr  Asp Val Asp Phe Leu  Ile Ser Pro Val Lys  Asn Ser Asp
    1145                1150                1155

Gly Ile  Phe Tyr Asp Ser Arg  Asn Tyr Glu Ala Gln  Glu Asn Ala
    1160                1165                1170

Ile Leu  Pro Lys Asn Ala Asp  Ala Asn Gly Ala Tyr  Asn Ile Ala
    1175                1180                1185

Arg Lys  Val Leu Trp Ala Ile  Gly Gln Phe Lys Lys  Ala Glu Asp
    1190                1195                1200

Glu Lys  Leu Asp Lys Val Lys  Ile Ala Ile Ser Asn  Lys Glu Trp
    1205                1210                1215

Leu Glu  Tyr Ala Gln Thr Ser  Val Lys His Lys Arg  Pro Ala Ala
    1220                1225                1230

Thr Lys  Lys Ala Gly Gln Ala  Lys Lys Lys Lys Gly  Ser Tyr Pro
    1235                1240                1245

Tyr Asp  Val Pro Asp Tyr Ala  Tyr Pro Tyr Asp Val  Pro Asp Tyr
    1250                1255                1260

Ala Tyr  Pro Tyr Asp Val Pro  Asp Tyr Ala
    1265                1270
```

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 11
tttccctcac tcctgctcgg tgaattt 27

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 12
tttcggtcac tcctgctcgg tgaattt 27

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 13
tttcccagac tcctgctcgg tgaattt 27

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 14
tttccctctg tcctgctcgg tgaattt 27

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 15
tttccctcac agctgctcgg tgaattt 27

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 16
tttccctcac tcgagctcgg tgaattt 27

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 17
tttccctcac tcctcgtcgg tgaattt 27

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 18
tttccctcac tcctgcaggg tgaattt 27

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19
tttccctcac tcctgctccc tgaattt 27

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 20
tttccctcac tcctgctcgg acaattt 27

-continued

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 21
tttccctcac tcctgctcgg tgttttt 27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 22
tttccctcac tcctgctcgg tgaaaat 27

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 23
tttccctcac tcctgctcgg tgaataa 27

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 24
tttcgctcac tcctgctcgg tgaattt 27

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 25
tttccgtcac tcctgctcgg tgaattt 27

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 26
tttcccacac tcctgctcgg tgaattt 27

<210> SEQ ID NO 27

-continued

<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 27
tttccctgac tcctgctcgg tgaattt 27

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 28
tttccctctc tcctgctcgg tgaattt 27

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 29
tttccctcag tcctgctcgg tgaattt 27

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 30
tttccctcac acctgctcgg tgaattt 27

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 31
tttccctcac tgctgctcgg tgaattt 27

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 32
tttccctcac tcgtgctcgg tgaattt 27

<210> SEQ ID NO 33
<211> LENGTH: 27

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 33
tttccctcac tccagctcgg tgaattt 27

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 34
tttccctcac tcctcctcgg tgaattt 27

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 35
tttccctcac tcctggtcgg tgaattt 27

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 36
tttccctcac tcctgcacgg tgaattt 27

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 37
tttccctcac tcctgctggg tgaattt 27

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 38
tttccctcac tcctgctccg tgaattt 27

<210> SEQ ID NO 39
<211> LENGTH: 27
<212> TYPE: DNA

-continued

<213> ORGANISM: Artificial Sequence
<220> FEATURE:
<223> OTHER INFORMATION: Description of Artificial Sequence: Synthetic
oligonucleotide

<400> SEQUENCE: 39
tttccctcac tcctgctcgc tgaattt 27

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 40
tttccctcac tcctgctcgg agaattt 27

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 41
tttccctcac tcctgctcgg tcaattt 27

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 42
tttccctcac tcctgctcgg tgtattt 27

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 43
tttccctcac tcctgctcgg tgatttt 27

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 44
tttccctcac tcctgctcgg tgaaatt 27

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tttccctcac tcctgctcgg tgaatat 27

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tttccctcac tcctgctcgg tgaatta 27

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tttccctcac tcctgctcgg tgaatttggc 30

<210> SEQ ID NO 48
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tttccctcac tcctgctcgg tgaatttgg 29

<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tttccctcac tcctgctcgg tgaatttg 28

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tttccctcac tcctgctcgg tgaatt 26

<210> SEQ ID NO 51
<211> LENGTH: 25
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 51
tttccctcac tcctgctcgg tgaat 25

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tttccctcac tcctgctcgg tgaa 24

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tttcgctcac tcctgctcgg tgaa 24

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
tttccgtcac tcctgctcgg tgaa 24

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
tttcccacac tcctgctcgg tgaa 24

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tttccctgac tcctgctcgg tgaa 24

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 57
tttccctctc tcctgctcgg tgaa 24

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 58
tttccctcag tcctgctcgg tgaa 24

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 59
tttccctcac acctgctcgg tgaa 24

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 60
tttccctcac tgctgctcgg tgaa 24

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 61
tttccctcac tcgtgctcgg tgaa 24

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 62
tttccctcac tccagctcgg tgaa 24

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 63
tttccctcac tcctcctcgg tgaa 24

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 64
tttccctcac tcctggtcgg tgaa 24

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 65
tttccctcac tcctgcacgg tgaa 24

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 66
tttccctcac tcctgctggg tgaa 24

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 67
tttccctcac tcctgctccg tgaa 24

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 68
tttccctcac tcctgctcgc tgaa 24

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 69
tttccctcac tcctgctcgg agaa 24

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 70
tttccctcac tcctgctcgg tcaa 24

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 71
tttccctcac tcctgctcgg tgta 24

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 72
tttccctcac tcctgctcgg tgat 24

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 73
tttccctcac tcctgctcgg tga 23

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 74
tttccctcac tcctgctcgg tg 22

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 75
tttccctcac tcctgctcgg t 21

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 76
tttccctcac tcctgctcgg 20

<210> SEQ ID NO 77
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 77
tttgaggagt gttcagtctc cgtgaac 27

<210> SEQ ID NO 78
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 78
tttcctgatg gtccatgtct gttactc 27

<210> SEQ ID NO 79
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 79
tttcgagatg gtccatgtct gttactc 27

<210> SEQ ID NO 80
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 80
tttcctcttg gtccatgtct gttactc 27

<210> SEQ ID NO 81
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 81
tttcctgaac gtccatgtct gttactc 27

<210> SEQ ID NO 82
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 82
tttcctgatg caccatgtct gttactc 27

<210> SEQ ID NO 83
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 83
tttcctgatg gtggatgtct gttactc 27

<210> SEQ ID NO 84
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 84
tttcctgatg gtcctagtct gttactc 27

<210> SEQ ID NO 85
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 85
tttcctgatg gtccatcact gttactc 27

<210> SEQ ID NO 86
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 86
tttcctgatg gtccatgtga gttactc 27

<210> SEQ ID NO 87
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 87
tttcctgatg gtccatgtct catactc 27

<210> SEQ ID NO 88
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 88
tttcctgatg gtccatgtct gtatctc 27

<210> SEQ ID NO 89
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 89
tttcctgatg gtccatgtct gttagac 27

<210> SEQ ID NO 90
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 90
tttcctgatg gtccatgtct gttacag 27

<210> SEQ ID NO 91
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 91
tttcgtgatg gtccatgtct gttactc 27

<210> SEQ ID NO 92
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 92
tttccagatg gtccatgtct gttactc 27

<210> SEQ ID NO 93
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 93
tttcctcatg gtccatgtct gttactc 27

<210> SEQ ID NO 94
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 94
tttcctgttg gtccatgtct gttactc 27

<210> SEQ ID NO 95
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 95
tttcctgaag gtccatgtct gttactc 27

<210> SEQ ID NO 96
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 96
tttcctgatc gtccatgtct gttactc 27

<210> SEQ ID NO 97
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 97
tttcctgatg ctccatgtct gttactc 27

<210> SEQ ID NO 98
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 98
tttcctgatg gaccatgtct gttactc 27

<210> SEQ ID NO 99
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 99
tttcctgatg gtgcatgtct gttactc 27

-continued

<210> SEQ ID NO 100
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 100
tttcctgatg gtcgatgtct gttactc 27

<210> SEQ ID NO 101
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 101
tttcctgatg gtccttgtct gttactc 27

<210> SEQ ID NO 102
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 102
tttcctgatg gtccaagtct gttactc 27

<210> SEQ ID NO 103
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 103
tttcctgatg gtccatctct gttactc 27

<210> SEQ ID NO 104
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 104
tttcctgatg gtccatgact gttactc 27

<210> SEQ ID NO 105
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 105
tttcctgatg gtccatgtgt gttactc 27

<210> SEQ ID NO 106

<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 106
tttcctgatg gtccatgtca gttactc 27

<210> SEQ ID NO 107
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 107
tttcctgatg gtccatgtct cttactc 27

<210> SEQ ID NO 108
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 108
tttcctgatg gtccatgtct gatactc 27

<210> SEQ ID NO 109
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 109
tttcctgatg gtccatgtct gtaactc 27

<210> SEQ ID NO 110
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 110
tttcctgatg gtccatgtct gtttctc 27

<210> SEQ ID NO 111
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 111
tttcctgatg gtccatgtct gttagtc 27

<210> SEQ ID NO 112
<211> LENGTH: 27

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 112
tttcctgatg gtccatgtct gttacac 27

<210> SEQ ID NO 113
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 113
tttcctgatg gtccatgtct gttactg 27

<210> SEQ ID NO 114
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 114
tttcctgatg gtccatgtct gttactcgcc 30

<210> SEQ ID NO 115
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 115
tttcctgatg gtccatgtct gttactcgc 29

<210> SEQ ID NO 116
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 116
tttcctgatg gtccatgtct gttactcg 28

<210> SEQ ID NO 117
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 117
tttcctgatg gtccatgtct gttact 26

<210> SEQ ID NO 118
<211> LENGTH: 25
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 118
tttcctgatg gtccatgtct gttac 25

<210> SEQ ID NO 119
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 119
tttcctgatg gtccatgtct gtta 24

<210> SEQ ID NO 120
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 120
tttcgtgatg gtccatgtct gtta 24

<210> SEQ ID NO 121
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 121
tttccagatg gtccatgtct gtta 24

<210> SEQ ID NO 122
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 122
tttcctcatg gtccatgtct gtta 24

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 123
tttcctgttg gtccatgtct gtta 24

<210> SEQ ID NO 124
<211> LENGTH: 24
<212> TYPE: DNA
<213> ORGANISM: Artificial Sequence -continued
<220> FEATURE:
<223> OTHER INFORMATION: Description of Artificial Sequence: Synthetic
oligonucleotide

<400> SEQUENCE: 124
tttcctgaag gtccatgtct gtta 24

<210> SEQ ID NO 125
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 125
tttcctgatc gtccatgtct gtta 24

<210> SEQ ID NO 126
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 126
tttcctgatg ctccatgtct gtta 24

<210> SEQ ID NO 127
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 127
tttcctgatg gaccatgtct gtta 24

<210> SEQ ID NO 128
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 128
tttcctgatg gtgcatgtct gtta 24

<210> SEQ ID NO 129
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 129
tttcctgatg gtcgatgtct gtta 24

<210> SEQ ID NO 130
<211> LENGTH: 24
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 130
tttcctgatg gtccttgtct gtta 24

<210> SEQ ID NO 131
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 131
tttcctgatg gtccaagtct gtta 24

<210> SEQ ID NO 132
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 132
tttcctgatg gtccatctct gtta 24

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 133
tttcctgatg gtccatgact gtta 24

<210> SEQ ID NO 134
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 134
tttcctgatg gtccatgtgt gtta 24

<210> SEQ ID NO 135
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 135
tttcctgatg gtccatgtca gtta 24

<210> SEQ ID NO 136
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 136
tttcctgatg gtccatgtct ctta 24

<210> SEQ ID NO 137
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 137
tttcctgatg gtccatgtct gata 24

<210> SEQ ID NO 138
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 138
tttcctgatg gtccatgtct gtaa 24

<210> SEQ ID NO 139
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 139
tttcctgatg gtccatgtct gttt 24

<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 140
tttcctgatg gtccatgtct gtt 23

<210> SEQ ID NO 141
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 141
tttcctgatg gtccatgtct gt 22

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 142
tttcctgatg gtccatgtct g 21

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 143
tttcctgatg gtccatgtct 20

<210> SEQ ID NO 144
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 144
tttatttccc ttcagctaaa ataaagg 27

<210> SEQ ID NO 145
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 145
tttattttag ctgaagggaa ataaaag 27

<210> SEQ ID NO 146
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 146
ttttatttcc cttcagctaa aataaag 27

<210> SEQ ID NO 147
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 147
tttggctcag caggcacctg cctcagc 27

<210> SEQ ID NO 148
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 148
tttgcgtcag caggcacctg cctcagc 27

<210> SEQ ID NO 149
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 149
tttggcagag caggcacctg cctcagc 27

<210> SEQ ID NO 150
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 150
tttggctctc caggcacctg cctcagc 27

<210> SEQ ID NO 151
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 151
tttggctcag gtggcacctg cctcagc 27

<210> SEQ ID NO 152
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 152
tttggctcag cacccacctg cctcagc 27

<210> SEQ ID NO 153
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 153
tttggctcag cagggtcctg cctcagc 27

<210> SEQ ID NO 154
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 154
tttggctcag caggcaggtg cctcagc 27

<210> SEQ ID NO 155
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 155
tttggctcag caggcaccac cctcagc 27

<210> SEQ ID NO 156
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 156
tttggctcag caggcacctg ggtcagc 27

<210> SEQ ID NO 157
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 157
tttggctcag caggcacctg ccagagc 27

<210> SEQ ID NO 158
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 158
tttggctcag caggcacctg cctctcc 27

<210> SEQ ID NO 159
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 159
tttggctcag caggcacctg cctcacg 27

<210> SEQ ID NO 160
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 160
tttggctcag caggcacctg cctcagctgc 30

<210> SEQ ID NO 161
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 161
tttggctcag caggcacctg cctcagctg 29

<210> SEQ ID NO 162
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 162
tttggctcag caggcacctg cctcagct 28

<210> SEQ ID NO 163
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 163
tttggctcag caggcacctg cctcag 26

<210> SEQ ID NO 164
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 164
tttggctcag caggcacctg cctca 25

<210> SEQ ID NO 165
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 165
tttggctcag caggcacctg cctc 24

<210> SEQ ID NO 166
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 166
tttggctcag caggcacctg cct 23

<210> SEQ ID NO 167
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 167
tttggctcag caggcacctg cc 22

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 168
tttggctcag caggcacctg c 21

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 169
tttggctcag caggcacctg 20

<210> SEQ ID NO 170
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 170
tttctcatct gtgcccctcc ctccctg 27

<210> SEQ ID NO 171
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 171
tttgtcctcc ggttctggaa ccacacc 27

<210> SEQ ID NO 172
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 172
tttgtggttg cccaccctag tcattgg 27

<210> SEQ ID NO 173
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 173
tttgtacttt gtcctccggt tctggaa 27

<210> SEQ ID NO 174
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 174
tttgggcggg gtccagttcc gggatta 27

<210> SEQ ID NO 175
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 175
tttggtcggc atggccccat tcgcacg 27

<210> SEQ ID NO 176
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 176
ttttccgagc ttctggcggt ctcaagc 27

<210> SEQ ID NO 177
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 177
tttcaccttg gagacggcga ctctctg 27

<210> SEQ ID NO 178
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 178
ttttcaggag gaagcgatgg cttcaga 27

-continued

<210> SEQ ID NO 179
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 179
tttcgctccg aaggtaaaag aaatcat 27

<210> SEQ ID NO 180
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 180
tttcagcctc acccctctag ccctaca 27

<210> SEQ ID NO 181
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 181
tttcttctcc cctctgctgg atacctc 27

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 182
gtcactctgg ggaacacgcc 20

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 183
gagtgctaag ggaacgttca 20

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 184
gagactgaac actcctcaaa 20

<210> SEQ ID NO 185

-continued

<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ggagtgaggg aaacggcccc 20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
gagtccgagc agaagaagaa 20

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
gtcacctcca atgactaggg 20

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
ggaatccctt ctgcagcacc 20

<210> SEQ ID NO 189
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
gctgcagaag ggattccatg 20

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
gcattttcag gaggaagcga 20

<210> SEQ ID NO 191
<211> LENGTH: 20

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 191
gggagaagaa agagagatgt 20

<210> SEQ ID NO 192
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 192

Gly Gly Gly Gly Ser
1 5

<210> SEQ ID NO 193
<211> LENGTH: 7
<212> TYPE: PRT
<213> ORGANISM: Simian virus 40

<400> SEQUENCE: 193

Pro Lys Lys Lys Arg Arg Val
1 5

<210> SEQ ID NO 194
<211> LENGTH: 16
<212> TYPE: PRT
<213> ORGANISM: Unknown
<220> FEATURE:
<223> OTHER INFORMATION: Description of Unknown:
Nucleoplasmin NLS peptide

<400> SEQUENCE: 194

Lys Arg Pro Ala Ala Thr Lys Lys Ala Gly Gln Ala Lys Lys Lys Lys
1 5 10 15

<210> SEQ ID NO 195
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 195

Gly Gly Gly Ser
1

<210> SEQ ID NO 196
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 196

His His His His His His
1 5

<210> SEQ ID NO 197

-continued

```
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197

tttccagttg gtccatgtct gttactc                                         27


<210> SEQ ID NO 198
<211> LENGTH: 6
<212> TYPE: PRT
<213> ORGANISM: Unknown
<220> FEATURE:
<223> OTHER INFORMATION: Description of Unknown:
      Lachnospiraceae bacterium peptide

<400> SEQUENCE: 198

Met Ser Lys Leu Glu Lys
1               5
```

VARIANTS OF CRISPR FROM *PREVOTELLA* AND *FRANCISELLA* 1 (CPF1)

CLAIM OF PRIORITY

This application is a divisional of U.S. patent application Ser. No. 15/659,499, filed Jul. 25, 2017, which claims the benefit of U.S. Patent Application Ser. No. 62/366,976, filed on Jul. 26, 2016. The entire contents of the foregoing are hereby incorporated by reference.

FEDERALLY SPONSORED RESEARCH OR DEVELOPMENT

This invention was made with Government support under Grant Nos. HG009490, GM118158, and GM105378 awarded by the National Institutes of Health. The Government has certain rights in the invention.

SEQUENCE LISTING

This application contains a Sequence Listing that has been submitted electronically as an ASCII text file named “Sequence_Listing.txt.” The ASCII text file, created on Oct. 8, 2021, is 101,336 bytes in size. The material in the ASCII text file is hereby incorporated by reference in its entirety.

TECHNICAL FIELD

The invention relates, at least in part, to engineered CRISPR from *Prevotella* and *Francisella* 1 (Cpf1) nucleases with altered and improved target specificity and their use in genomic engineering, epigenomic engineering, genome targeting, genome editing, and in vitro diagnostics.

BACKGROUND

CRISPR systems enable efficient genome editing in a wide variety of organisms and cell types. The genome-wide specificity of engineered nucleases, including those derived from CRISPR bacterial immune systems such as Cas9 and Cpf1, is of utmost importance when considering such tools for both research and therapeutic applications.

SUMMARY

As described herein, Cpf1 Proteins can be engineered to show increased specificity, theoretically by reducing the binding affinity of Cpf1 for DNA. Thus, described herein are a number of Cpf1 variants, e.g., from *Acidaminococcus* sp. BV31.6 and *Lachnospiraceae bacterium* ND2006 (AsCpf1 and LbCpf1, respectively), that have been engineered to exhibit increased specificity (i.e., induce substantially fewer off target effects) as compared to the wild type protein, as well as methods of using them.

In a first aspect, the invention provides isolated *Lachnospiraceae bacterium* ND2006 Cpf1 (LbCpf1) proteins, with one or more mutations listed in Table 1, e.g., with mutations at one, two, three, four, five, six or all seven of the following positions: S186 N274, N278, K290, K367, K532, K609, K915, Q962, K963, K966, K1002 and/or S1003, e.g., comprising a sequence that is at least 80% identical to the amino acid sequence of at least amino acids 23-1246 SEQ ID NO:1 (or at least amino acids 18-of SEQ ID NO:1) with mutations at one, two, three, four, five, six, or seven of the following positions S186, N274, N278, K290, K367, K532, K609, K915, Q962, K963, K966, K1002 and/or S1003, and optionally one or more of a nuclear localization sequence, cell penetrating peptide sequence, and/or affinity tag. A mutation alters the amino acid to an amino acid other than the native amino acid (e.g., 497 is anything but N). In preferred embodiments the mutation changes the amino acid to any amino acid other than the native one, arginine or lysine; in some embodiments, the amino acid is alanine.

In some embodiments, the variant LbCpf1 proteins comprise one, two, three, or all four of the following mutations: S186, N274A, N278A, K290A, K367A, K532A, K609A, K915A, Q962A, K963A, K966A, K1002A and/or S1003A.

In some embodiments, the variant LbCpf1 proteins also comprise one or more mutations that decrease nuclease activity selected from the group consisting of mutations listed in Table A, e.g., mutations at D832 and/or E925, e.g., D832A and E925A.

Also provided herein are isolated *Acidaminococcus* sp. BV31.6 Cpf1 (AsCpf1) proteins, with one or more mutations listed in Table 1, e.g., with mutations at one, two, three, four, five, or six of the following positions: N178, N278, N282, R301, T315, S376, N515, K523, K524, K603, K965, Q1013, and/or K1054, e.g., comprising a sequence that is at least 80% identical to the amino acid sequence of SEQ ID NO:2 with mutations at one, two, three, four, or five, or six of the following positions: N178, N278, N282, R301, T315, S376, N515, K523, K524, K603, K965, Q1013, and/or K1054, and optionally one or more of a nuclear localization sequence, cell penetrating peptide sequence, and/or affinity tag. In some embodiments, the AsCpf1 variants described herein include the amino acid sequence of SEQ ID NO:2, with mutations at one, two, three, four, five, or all six of the following positions: N178A, N278A, N282A, R301A, T315A, S376A, N515A, K523A, K524A, K603A, K965A, Q1013A, and/or K1054A.

In some embodiments, the variant AsCpf1 proteins also comprise one or more mutations that decrease nuclease activity selected from the group consisting of mutations listed in Table A, e.g., mutations at D908 and/or E993, e.g., D908A and/or E993A.

Also provided herein are fusion proteins comprising the isolated variant Cpf1 proteins described herein fused to a heterologous functional domain, with an optional intervening linker, wherein the linker does not interfere with activity of the fusion protein. In preferred embodiments, the heterologous functional domain acts on DNA or protein, e.g., on chromatin. In some embodiments, the heterologous functional domain is a transcriptional activation domain. In some embodiments, the transcriptional activation domain is from VP64 or NF-κB p65. In some embodiments, the heterologous functional domain is a transcriptional silencer or transcriptional repression domain. In some embodiments, the transcriptional repression domain is a Kruppel-associated box (KRAB) domain, ERF repressor domain (ERD), or mSin3A interaction domain (SID). In some embodiments, the transcriptional silencer is Heterochromatin Protein 1 (HP1), e.g., HP1α or HP1β. In some embodiments, the heterologous functional domain is an enzyme that modifies the methylation state of DNA. In some embodiments, the enzyme that modifies the methylation state of DNA is a DNA methyltransferase (DNMT) or the entirety or the dioxygenase domain of a TET protein, e.g., a catalytic module comprising the cysteine-rich extension and the 2OGFeDO domain encoded by 7 highly conserved exons, e.g., the Tet1 catalytic domain comprising amino acids 1580-2052, Tet2 comprising amino acids 1290-1905 and Tet3 comprising amino acids 966-1678. In some embodiments, the TET protein or TET-derived dioxygenase domain is from TET1. In some embodiments, the heterologous functional domain is an enzyme that modifies a histone subunit. In some embodiments, the enzyme that modifies a histone subunit is a histone acetyltransferase (HAT), histone deacetylase (HDAC), histone methyltransferase (HMT), or histone demethylase. In some embodiments, the heterologous functional domain is a biological tether. In some embodiments, the biological tether is MS2, Csy4 or lambda N protein. In some embodiments, the heterologous functional domain is FokI.

Also provided herein are nucleic acids, isolated nucleic acids encoding the variant Cpf1 proteins described herein, as well as vectors comprising the isolated nucleic acids, optionally operably linked to one or more regulatory domains for expressing the variant Cpf1 proteins described herein. Also provided herein are host cells, e.g., bacterial, yeast, insect, or mammalian host cells or transgenic animals (e.g., mice), comprising the nucleic acids described herein, and optionally expressing the variant Cpf1 proteins described herein.

Also provided herein are methods of altering the genome of a cell, by expressing in the cell isolated variant Cpf1 proteins as described herein, in the presence of at least one guide RNA having a region complementary to a selected portion of the genome of the cell with optimal nucleotide spacing at the genomic target site.

Also provided herein are methods of altering the genome of a cell, by expressing in the cell an isolated variant Cpf1 protein described herein, in the presence of at least one guide RNA having a region complementary to a selected portion of the genome of the cell with optimal nucleotide spacing at the genomic target site.

Also provided herein are isolated nucleic acids encoding the Cpf1 variants, as well as vectors comprising the isolated nucleic acids, optionally operably linked to one or more regulatory domains for expressing the variants, and host cells, e.g., mammalian host cells, comprising the nucleic acids, and optionally expressing the variant proteins.

Also provided herein are methods for altering, e.g., selectively altering, the genome of a cell by contacting the cell with, or expressing in the cell, a variant protein as described herein, and a guide RNA having a region complementary to a selected portion of the genome of the cell. In some embodiments, the isolated protein or fusion protein comprises one or more of a nuclear localization sequence, cell penetrating peptide sequence, and/or affinity tag.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A discloses the DNMT1 site 1 sequences as SEQ ID NOS 11-13 and 23, respectively, in order of appearance, the DNMT1 site 3 sequences as SEQ ID NOS 78-80 and 90, respectively, in order of appearance, and the DNMT1 site 7 sequences as SEQ ID NOS 147-149 and 159, respectively, in order of appearance. FIG. 1B discloses the DNMT1 site 1 sequences as SEQ ID NOS 11, 24, 25 and 46, respectively, in order of appearance, and the DNMT1 site 3 sequences as SEQ ID NOS 78, 91, 197 and 113, respectively, in order of appearance.

DETAILED DESCRIPTION

Figure 1A:
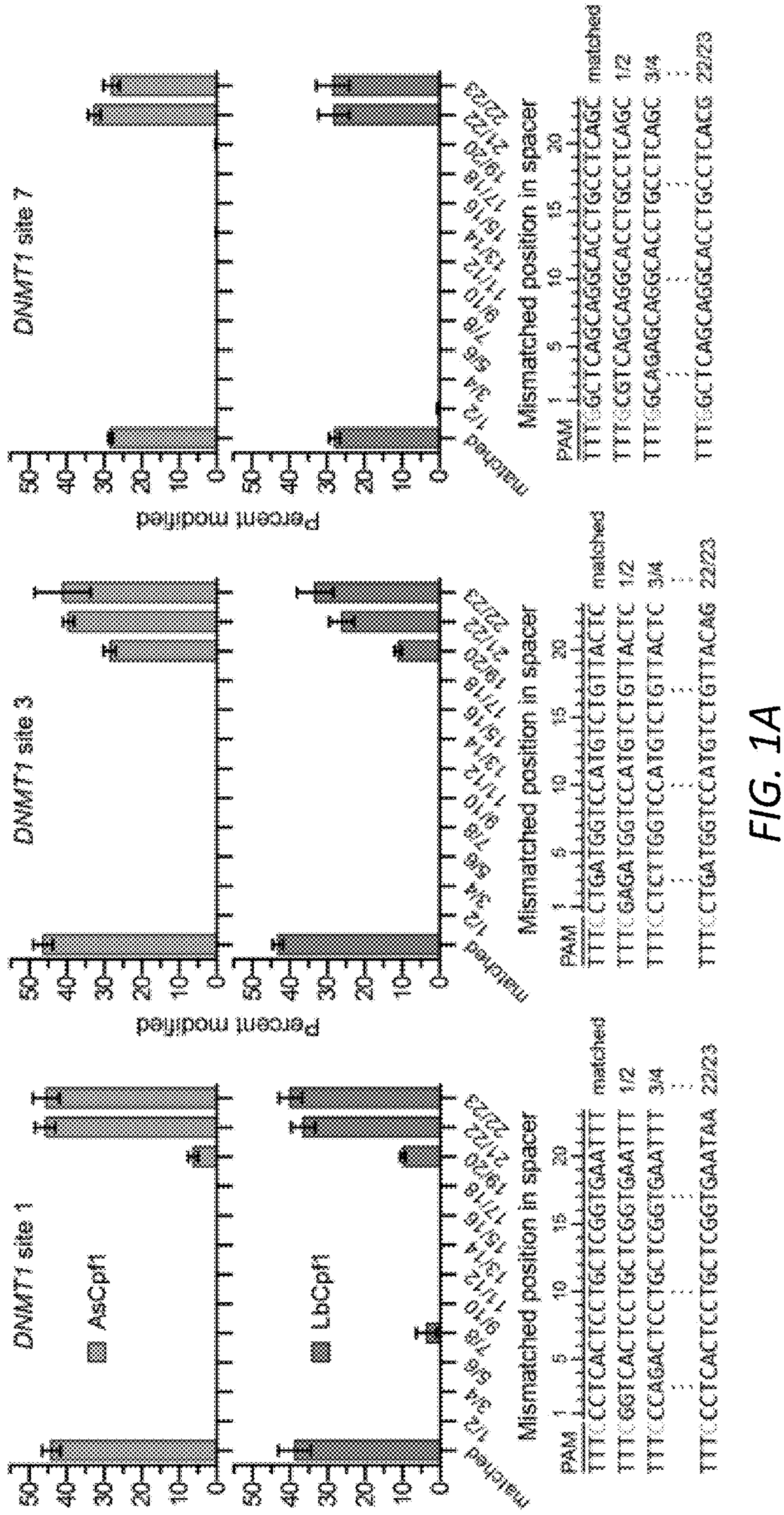
FIGS. 1A-B are bar graphs showing tolerance of AsCpf1 and LbCpf1 to mismatched crRNAs for DNMT1 sites 1 and 3. (A, B) Endogenous gene modification by AsCpf1 and LbCpf1 using crRNAs that contain pairs of mismatched bases (1A) or singly mismatched bases (1B). Activity determined by T7E1 assay; error bars, s.e.m.; n=3.

The on- and off-target activities of two CRISPR-Cas Cpf1 orthologues from *Acidaminococcus* sp. BV3L6 and *Lachnospiraceae bacterium* ND2006 (AsCpf1 and LbCpf1, respectively) were recently characterized; see Kleinstiver & Tsai et al., "Genome-wide specificities of CRISPR-Cas Cpf1 nucleases in human cells," Nature Biotechnology 2016 Jun. 27. doi: 10.1038/nbt.3620, Epub ahead of print). Using crRNAs with intentionally mismatched positions (to mimic mismatched off-target sites) and an unbiased genome-wide detection assay named GUIDE-seq (Tsai et al., Nat Biotechnol 33, 187-197 (2015)), it was determined that both AsCpf1 and LbCpf1 have generally high genome-wide specificities but can still tolerate nucleotide mismatches in parts of the crRNA.

Thus, to generate variants with higher fidelity (i.e., less likelihood of binding to target sites with one or more mismatches, like the *Streptococcus pyogenes* Cas9 variants (SpCas9-HF) described in Kleinstiver et al., Nature 529, 490-495 (2016)), we made site directed mutations in the Cpf1 coding sequence to improve their genome-wide specificities. The site directed mutations in residues that presumably make contacts to the DNA-backbone of either the target or non-target DNA strand are meant to improve the fidelity of the enzymes by imparting a heightened ability to discriminate against off-target sites. We have identified a number of mutations that can provide such an effect. These studies are performed on AsCpf1 and LbCpf1, enzymes whose specificities have not yet been altered. Importantly, because the Cas9 and Cpf1 enzymes are substantially different at both the primary amino acid sequence level and in their three-dimensional domain organization and structures, it is not at all obvious which amino acid change(s) will be needed to create high-fidelity versions of Cpf1 enzymes. Furthermore, while a crystal structure has been solved for AsCpf1 providing insight into which residues to mutate, for LbCpf1 we are identifying residues to mutate based on alignment with other Cpf1 orthologues.

These higher fidelity Cpf1 (Cpf1-HF) enzymes are useful in both research and therapeutic settings, e.g., for genomic engineering, epigenomic engineering, genome targeting, and genome editing (for example, if you can target an allele with single nucleotide precision, then you can target either the wild-type (reference genome) sequence or the disease allele. This would allow genotyping at disease loci). Methods for using Cpf1 enzymes are known in the art, see, e.g., Yamano et al., Cell. 2016 May 5; 165(4):949-62; Fonfara et al., Nature. 2016 Apr. 28; 532(7600):517-21; Dong et al., Nature. 2016 Apr. 28; 532(7600):522-6; and Zetsche et al., Cell. 2015 Oct. 22; 163(3):759-71.

Cpf1

Clustered, regularly interspaced, short palindromic repeat (CRISPR) systems encode RNA-guided endonucleases that are essential for bacterial adaptive immunity (Wright et al., Cell 164, 29-44 (2016)). CRISPR-associated (Cas) nucleases can be readily programmed to cleave target DNA sequences for genome editing in various organisms[2-5]. One class of these nucleases, referred to as Cas9 proteins, complex with two short RNAs: a crRNA and a trans-activating crRNA (tracrRNA)[7, 8]. The most commonly used Cas9 ortholog, SpCas9, uses a crRNA that has 20 nucleotides (nt) at its 5' end that are complementary to the "protospacer" region of the target DNA site. Efficient cleavage also requires that SpCas9 recognizes a protospacer adjacent motif (PAM). The crRNA and tracrRNA are usually combined into a single ~100-nt guide RNA (gRNA)[7, 9-11] that directs the DNA cleavage activity of SpCas9. The genome-wide specificities of SpCas9 nucleases paired with different gRNAs have been characterized using many different approaches[12-15]. SpCas9 variants with substantially improved genome-wide specificities have also been engineered[16, 17].

Recently, a Cas protein named Cpf1 has been identified that can also be programmed to cleave target DNA sequences[1, 18-20]. Unlike SpCas9, Cpf1 requires only a single 42-nt crRNA, which has 23 nt at its 3' end that are complementary to the protospacer of the target DNA sequence[1]. Furthermore, whereas SpCas9 recognizes an NGG PAM sequence that is 3' of the protospacer, AsCpf1 and LbCp1 recognize TTTN PAMs that are found 5' of the protospacer[1]. Early experiments with AsCpf1 and LbCpf1 showed that these nucleases can be programmed to edit target sites in human cells[1] but they were tested on only a small number of sites. On-target activities and genome-wide specificities of both AsCpf1 and LbCpf1 were characterized in Kleinstiver & Tsai et al., Nature Biotechnology 2016.

The present findings provide support for AsCpf1 and LbCpf1 variants, referred to collectively herein as "variants" or "the variants".

All of the variants described herein can be rapidly incorporated into existing and widely used vectors, e.g., by simple site-directed mutagenesis.

Thus, provided herein are Cpf1 variants, including LbCpf1 variants. The LbCpf1 wild type protein sequence is as follows:

Type V CRISPR-associated protein Cpf1 [*Lachnospiraceae bacterium* ND2006], GenBank Acc No. WP_051666128.1

(SEQ ID NO: 1)

```
  1 MLKNVGIDRL DVEKGRKNMS KLEKFTNCYS LSKTLRFKAI PVGKTQENID NKRLLVEDEK
 61 RAEDYKGVKK LLDRYYLSFI NDVLHSIKLK NLNNYISLFR KKTRTEKENK ELENLEINLR
121 KEIAKAFKGN EGYKSLFKKD IIETILPEFL DDKDEIALVN SFNGFTTAFT GFFDNRENMF
181 SEEAKSTSIA FRCINENLTR YISNMDIFEK VDAIFDKHEV QEIKEKILNS DYDVEDFFEG
241 EFFNFVLTQE GIDVYNAIIG GFVTESGEKI KGLNEYINLY NQKTKQKLPK FKPLYKQVLS
301 DRESLSFYGE GYTSDEEVLE VFRNTLNKNS EIFSSIKKLE KLFKNFDEYS SAGIFVKNGP
361 AISTISKDIF GEWNVIRDKW NAEYDDIHLK KKAVVTEKYE DDRRKSFKKI GSFSLEQLQE
421 YADADLSVVE KLKEIIIQKV DEIYKVYGSS EKLFDADFVL EKSLKKNDAV VAIMKDLLDS
481 VKSFENYIKA FFGEGKETNR DESFYGDFVL AYDILLKVDH IYDAIRNYVT QKPYSKDKFK
541 LYFQNPQFMG GWDKDKETDY RATILRYGSK YYLAIMDKKY AKCLQKIDKD DVNGNYEKIN
601 YKLLPGPNKM LPKVFFSKKW MAYYNPSEDI QKIYKNGTFK KGDMFNLNDC HKLIDFFKDS
661 ISRYPKWSNA YDFNFSETEK YKDIAGFYRE VEEQGYKVSF ESASKKEVDK LVEEGKLYMF
721 QIYNKDFSDK SHGTPNLHTM YFKLLFDENN HGQIRLSGGA ELFMRRASLK KEELVVHPAN
781 SPIANKNPDN PKKTTTLSYD VYKDKRFSED QYELHIPIAI NKCPKNIFKI NTEVRVLLKH
841 DDNPYVIGID RGERNLLYIV VVDGKGNIVE QYSLNEIINN FNGIRIKTDY HSLLDKKEKE
901 RFEARQNWTS IENIKELKAG YISQVVHKIC ELVEKYDAVI ALEDLNSGFK NSRVKVEKQV
961 YQKFEKMLID KLNYMVDKKS NPCATGGALK GYQITNKFES FKSMSTQNGF IFYIPAWLTS
```

-continued

| Type V CRISPR-associated protein Cpf1 [*Lachnospiraceae bacterium* ND2006], GenBank Acc No. WP_051666128.1 |
|---|
| 1021 KIDPSTGFVN LLKTKYTSIA DSKKFISSFD RIMYVPEEDL FEFALDYKNF SRTDADYIKK |
| 1081 WKLYSYGNRI RIFRNPKKNN VFDWEEVCLT SAYKELFNKY GINYQQGDIR ALLCEQSDKA |
| 1141 FYSSFMALMS LMLQMRNSIT GRTDVDFLIS PVKNSDGIFY DSRNYEAQEN AILPKNADAN |
| 1201 GAYNIARKVL WAIGQFKKAE DEKLDKVKIA ISNKEWLEYA QTSVKH |

The LbCpf1 variants described herein can include the amino acid sequence of SEQ ID NO:1, e.g., at least comprising amino acids 23-1246 of SEQ ID NO:1, with mutations (i.e., replacement of the native amino acid with a different amino acid, e.g., alanine, glycine, or serine), at one or more positions in Table 1, e.g., at the following positions: S168, N256, N260, K272, K349, K514, K591, K897, Q944, K945, K948, K984, and/or S985 of SEQ ID NO: 10 (or at positions analogous thereto, e.g., S186, N274, N278, K290, K367, K532, K609, K915, Q962, K963, K966, K1002, and/or S1003 of SEQ ID NO:1); amino acids 19-1246 of SEQ ID NO: 1 are identical to amino acids 1-1228 of SEQ ID NO:10 (amino acids 1-1228 of SEQ ID NO: 10 are referred to herein as LbCPF1 (−18)). In some embodiments, the LbCpf1 variants are at least 80%, e.g., at least 85%, 90%, or 95% identical to the amino acid sequence of SEQ ID NO:1, e.g., have differences at up to 5%, 10%, 15%, or 20% of the residues of SEQ ID NO: 1 replaced, e.g., with conservative mutations, in addition to the mutations described herein. In preferred embodiments, the variant retains desired activity of the parent, e.g., the nuclease activity (except where the parent is a nickase or a dead Cpf1), and/or the ability to interact with a guide RNA and target DNA). The version of LbCpf1 used in the present working examples starts at the MSKLEK motif (SEQ ID NO: 198), omitting the first 18 amino acids boxed above as described in Zetsche et al. Cell 163, 759-771 (2015).

Type V CRISPR-associated protein Cpf1 [*Acidaminococcus* sp. BV3L6], NCBI Reference Sequence: WP_021736722.1

(SEQ ID NO: 2)

```
   1 MTQFEGFTNL YQVSKTLRFE LIPQGKTLKH IQEQGFIEED
     KARNDHYKEL KPIIDRIYKT
  61 YADQCLQLVQ LDWENLSAAI DSYRKEKTEE TRNALIEEQA
     TYRNAIHDYF IGRIDNLIDA
 121 INKRHAEIYK GLFKAELFNG KVLKQLGTVT TTEHENALLR
     SFDKFTTYFS GFYENRKNVF
 181 SAEDISTAIP HRIVQDNFPK FKENCHIFTR LITAVPSLRE
     HFENVKKAIG IFVSTSIEEV
 241 FSFPFYNQLL TQTQIDLYNQ LLGGISREAG TEKIKGLNEV
     LNLAIQKNDE TAHIIASLPH
 301 RFIPLFKQIL SDRNTLSFIL EEFKSDEEVI QSFCKYKTLL
     RNENVLETAE ALFNELNSID
```

-continued

```
 361 LTHIFISHKK LETISSALCD HWDTLRNALY ERRISELTGK
     ITKSAKEKVQ RSLKHEDINL
 421 QEIISAAGKE LSEAFKQKTS EILSHAHAAL DQPLPTTLKK
     QEEKEILKSQ LDSLLGLYHL
 481 LDWFAVDESN EVDPEFSARL TGIKLEMEPS LSFYNKARNY
     ATKKPYSVEK FKLNFQMPTL
 541 ASGWDVNKEK NNGAILFVKN GLYYLGIMPK QKGRYKALSF
     EPTEKTSEGF DKMYYDYFPD
 601 AAKMIPKCST QLKAVTAHFQ THTTPILLSN NFIEPLEITK
     EIYDLNNPEK EPKKFQTAYA
 661 KKTGDQKGYR EALCKWIDFT RDFLSKYTKT TSIDLSSLRP
     SSQYKDLGEY YAELNPLLYH
 721 ISFQRIAEKE IMDAVETGKL YLFQIYNKDF AKGHHGKPNL
     HTLYWTGLFS PENLAKTSIK
 781 LNGQAELFYR PKSRMKRMAH RLGEKMLNKK LKDQKTPIPD
     TLYQELYDYV NHRLSHDLSD
 841 EARALLPNVI TKEVSHEIIK DRRFTSDKFF FHVPITLNYQ
     AANSPSKFNQ RVNAYLKEHP
 901 ETPIIGIDRG ERNLIYITVI DSTGKILEQR SLNTIQQFDY
     QKKLDNREKE RVAARQAWSV
 961 VGTIKDLKQG YLSQVIHEIV DLMIHYQAVV VLENLNFGFK
     SKRTGIAEKA VYQQFEKMLI
1021 DKLNCLVLKD YPAEKVGGVL NPYQLTDQFT SFAKMGTQSG
     FLFYVPAPYT SKIDPLTGFV
1081 DPFVWKTIKN HESRKHFLEG FDFLHYDVKT GDFILHFKMN
     RNLSFQRGLP GFMPAWDIVF
1141 EKNETQFDAK GTPFIAGKRI VPVIENHRFT GRYRDLYPAN
     ELIALLEEKG IVFRDGSNIL
1201 PKLLENDDSH AIDTMVALIR SVLQMRNSNA ATGEDYINSP
     VRDLNGVCFD SRFQNPEWPM
1261 DADANGAYHI ALKGQLLLNH LKESKDLKLQ NGISNQDWLA
     YIQELRN
```

The AsCpf1 variants described herein can include the amino acid sequence of SEQ ID NO:2, e.g., at least comprising amino acids 1-1307 of SEQ ID NO:2, with mutations (i.e., replacement of the native amino acid with a different amino acid, e.g., alanine, glycine, or serine (except where the native amino acid is serine)), at one or more positions in Table 1, e.g., at the following positions: N178, S186, N278, N282, R301, T315, S376, N515, K523, K524, K603, K965, Q1013, Q1014, and/or K1054 of SEQ ID NO: 2 (or at positions analogous thereto, e.g., of SEQ ID NO:8). In some embodiments, the AsCpf1 variants are at least 80%, e.g., at least 85%, 90%, or 95% identical to the amino acid sequence of SEQ ID NO:2, e.g., have differences at up to 5%, 10%, 15%, or 20% of the residues of SEQ ID NO:2 replaced, e.g., with conservative mutations, in addition to the mutations described herein. In preferred embodiments, the variant retains desired activity of the parent, e.g., the nuclease activity (except where the parent is a nickase or a dead Cpf1), and/or the ability to interact with a guide RNA and target DNA).

To determine the percent identity of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The nucleotides at corresponding amino acid positions or nucleotide positions are then compared. When a position in the first sequence is occupied by the same nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences. Percent identity between two polypeptides or nucleic acid sequences is determined in various ways that are within the skill in the art, for instance, using publicly available computer software such as Smith Waterman Alignment (Smith, T. F. and M. S. Waterman (1981) J Mol Biol 147:195-7); "BestFit" (Smith and Waterman, Advances in Applied Mathematics, 482-489 (1981)) as incorporated into GeneMatcher Plus™, Schwarz and Dayhof (1979) Atlas of Protein Sequence and Structure, Dayhof, M. O., Ed, pp 353-358; BLAST program (Basic Local Alignment Search Tool; (Altschul, S. F., W. Gish, et al. (1990) J Mol Biol 215:403-10), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins or nucleic acids, the length of comparison can be any length, up to and including full length (e.g., 5%, 10%, 20%, 30%, 40%, 50%, 60%, 70%, 80%, 90%, 95%, or 100%). For purposes of the present compositions and methods, at least 80% of the full length of the sequence is aligned.

For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

In some embodiments, the mutants have alanine in place of the wild type amino acid. In some embodiments, the mutants have any amino acid other than arginine or lysine (or the native amino acid).

In some embodiments, the Cpf1 variants also include one of the following mutations listed in Table A, which reduce or destroy the nuclease activity of the Cpf1:

TABLE A

| | AsCpf1 | LbCpf1 | LbCpf1 (−18) | FnCpf1 |
|---|---|---|---|---|
| Residues involved in DNA and RNA catalysis | | | | |
| DNA targeting | D908 | D850 | D832 | D917 |
| | E911 | E853 | E835 | E920 |
| | N913 | N855 | N837 | H922 |
| | Y916 | Y858 | Y840 | Y925 |
| | E993 | E943 | E925 | E1006 |
| | R1226 | R1156 | R1138 | R1218 |
| | S1228 | S1158 | S1140 | S1220 |
| | D1235 | D1166 | D1148 | D1227 |
| | D1263 | D1198 | D1180 | D1255 |
| | H800 | H777 | H759 | H843 |
| RNA processing | K809 | K786 | K768 | K852 |
| | K860 | K803 | K785 | K869 |
| | F864 | F807 | F789 | F873 |
| Mutations that turn Cpf1 into a nickase | | | | |
| | R1226A | R1156A | R1138A | R1218A |

See, e.g., Yamano et al., Cell. 2016 May 5; 165(4):949-62; Fonfara et al., Nature. 2016 Apr. 28; 532(7600):517-21; Dong et al., Nature. 2016 Apr. 28; 532(7600):522-6; and Zetsche et al., Cell. 2015 Oct. 22; 163(3):759-71. Note that "LbCpf1 (−18)" refers to the sequence of LbCpf1 in Zetsche et al., also shown herein as amino acids 1-1228 of SEQ ID NO: 10 and amino acids 19-1246 of SEQ ID NO:1.

Thus, in some embodiments, for AsCpf1, catalytic activity-destroying mutations are made at D908 and E993, e.g., D908A and E993A; and for LbCpf1 catalytic activity-destroying mutations at D832 and E925, e.g., D832A and E925A.

Also provided herein are isolated nucleic acids encoding the Cpf1 variants, vectors comprising the isolated nucleic acids, optionally operably linked to one or more regulatory domains for expressing the variant proteins, and host cells, e.g., mammalian host cells, comprising the nucleic acids, and optionally expressing the variant proteins.

The variants described herein can be used for altering the genome of a cell; the methods generally include expressing the variant proteins in the cells, along with a guide RNA having a region complementary to a selected portion of the genome of the cell. Methods for selectively altering the genome of a cell are known in the art, see, e.g., U.S. Pat. No. 8,993,233; US20140186958; U.S. Pat. No. 9,023,649; WO/2014/099744; WO 2014/089290; WO2014/144592; WO144288; WO2014/204578; WO2014/152432; WO2115/099850; U.S. Pat. No. 8,697,359; US20160024529; US20160024524; US20160024523; US20160024510; US20160017366; US20160017301; US20150376652; US20150356239; US20150315576; US20150291965; US20150252358; US20150247150; US20150232883; US20150232882; US20150203872; US20150191744; US20150184139; US20150176064; US20150167000; US20150166969; US20150159175; US20150159174; US20150093473; US20150079681; US20150067922;

US20150056629; US20150044772; US20150024500; US20150024499; US20150020223; US20140356867; US20140295557; US20140273235; US20140273226; US20140273037; US20140189896; US20140113376; US20140093941; US20130330778; US20130288251; US20120088676; US20110300538; US20110236530; US20110217739; US20110002889; US20100076057; US20110189776; US20110223638; US20130130248; US20150050699; US20150071899; US20150045546; US20150031134; US20150024500; US20140377868; US20140357530; US20140349400; US20140335620; US20140335063; US20140315985; US20140310830; US20140310828; US20140309487; US20140304853; US20140298547; US20140295556; US20140294773; US20140287938; US20140273234; US20140273232; US20140273231; US20140273230; US20140271987; US20140256046; US20140248702; US20140242702; US20140242700; US20140242699; US20140242664; US20140234972; US20140227787; US20140212869; US20140201857; US20140199767; US20140189896; US20140186958; US20140186919; US20140186843; US20140179770; US20140179006; US20140170753; WO/2008/108989; WO/2010/054108; WO/2012/164565; WO/2013/098244; WO/2013/176772; Makarova et al., "Evolution and classification of the CRISPR-Cas systems" 9(6) Nature Reviews Microbiology 467-477 (1-23) (June 2011); Wiedenheft et al., "RNA-guided genetic silencing systems in bacteria and archaea" 482 Nature 331-338 (Feb. 16, 2012); Gasiunas et al., "Cas9-crRNA ribonucleoprotein complex mediates specific DNA cleavage for adaptive immunity in bacteria" 109(39) Proceedings of the National Academy of Sciences USA E2579-E2586 (Sep. 4, 2012); Jinek et al., "A Programmable Dual-RNA-Guided DNA Endonuclease in Adaptive Bacterial Immunity" 337 Science 816-821 (Aug. 17, 2012); Carroll, "A CRISPR Approach to Gene Targeting" 20(9) Molecular Therapy 1658-1660 (September 2012); U.S. Appl. No. 61/652,086, filed May 25, 2012; Al-Attar et al., Clustered Regularly Interspaced Short Palindromic Repeats (CRISPRs): The Hallmark of an Ingenious Antiviral Defense Mechanism in Prokaryotes, Biol Chem. (2011) vol. 392, Issue 4, pp. 277-289; Hale et al., Essential Features and Rational Design of CRISPR RNAs That Function With the Cas RAMP Module Complex to Cleave RNAs, Molecular Cell, (2012) vol. 45, Issue 3, 292-302.

The variant proteins described herein can be used in place of or in addition to any of the Cas9 or Cpf1 proteins described in the foregoing references, or in combination with analogous mutations described therein. When replacing the Cas9, of course a guide RNA appropriate for the selected Cpf1 is used. In addition, the variants described herein can be used in fusion proteins in place of the wild-type Cas9 or other Cas9 mutations (such as the dCas9 or Cas9 nickase) as known in the art, e.g., a fusion protein with a heterologous functional domains as described in U.S. Pat. No. 8,993,233; US20140186958; U.S. Pat. No. 9,023,649; WO/2014/099744; WO 2014/089290; WO2014/144592; WO144288; WO2014/204578; WO2014/152432; WO2115/099850; U.S. Pat. No. 8,697,359; US2010/0076057; US2011/0189776; US2011/0223638; US2013/0130248; WO/2008/108989; WO/2010/054108; WO/2012/164565; WO/2013/098244; WO/2013/176772; US20150050699; US20150071899 and WO 2014/124284. For example, the variants, preferably comprising one or more nuclease-reducing or killing mutation, can be fused on the N or C terminus of the Cpf1 to a transcriptional activation domain or other heterologous functional domains (e.g., transcriptional repressors (e.g., KRAB, ERD, SID, and others, e.g., amino acids 473-530 of the ets2 repressor factor (ERF) repressor domain (ERD), amino acids 1-97 of the KRAB domain of KOX1, or amino acids 1-36 of the Mad mSIN3 interaction domain (SID); see Beerli et al., PNAS USA 95:14628-14633 (1998)) or silencers such as Heterochromatin Protein 1 (HP1, also known as swi6), e.g., HP1α or HP1β; proteins or peptides that could recruit long non-coding RNAs (lncRNAs) fused to a fixed RNA binding sequence such as those bound by the MS2 coat protein, endoribonuclease Csy4, or the lambda N protein; enzymes that modify the methylation state of DNA (e.g., DNA methyltransferase (DNMT) or TET proteins); or enzymes that modify histone subunits (e.g., histone acetyltransferases (HAT), histone deacetylases (HDAC), histone methyltransferases (e.g., for methylation of lysine or arginine residues) or histone demethylases (e.g., for demethylation of lysine or arginine residues)) as are known in the art can also be used. A number of sequences for such domains are known in the art, e.g., a domain that catalyzes hydroxylation of methylated cytosines in DNA. Exemplary proteins include the Ten-Eleven-Translocation (TET) 1-3 family, enzymes that converts 5-methylcytosine (5-mC) to 5-hydroxymethylcytosine (5-hmC) in DNA.

Sequences for human TET1-3 are known in the art and are shown in the following table:

| | GenBank Accession Nos. | |
|---|---|---|
| Gene | Amino Acid | Nucleic Acid |
| TET1 | NP_085128.2 | NM_030625.2 |
| TET2* | NP_001120680.1 (var 1) | NM_001127208.2 |
| | NP_060098.3 (var 2) | NM_017628.4 |
| TET3 | NP_659430.1 | NM_144993.1 |

*Variant (1) represents the longer transcript and encodes the longer isoform (a). Variant (2) differs in the 5' UTR and in the 3' UTR and coding sequence compared to variant 1. The resulting isoform (b) is shorter and has a distinct C-terminus compared to isoform a.

In some embodiments, all or part of the full-length sequence of the catalytic domain can be included, e.g., a catalytic module comprising the cysteine-rich extension and the 2OGFeDO domain encoded by 7 highly conserved exons, e.g., the Tet1 catalytic domain comprising amino acids 1580-2052, Tet2 comprising amino acids 1290-1905 and Tet3 comprising amino acids 966-1678. See, e.g., FIG. 1 of Iyer et al., Cell Cycle. 2009 Jun. 1; 8(11):1698-710. Epub 2009 Jun. 27, for an alignment illustrating the key catalytic residues in all three Tet proteins, and the supplementary materials thereof (available at ftp site ftp.ncbi.nih.gov/pub/aravind/DONS/supplementary_material_DONS.html) for full length sequences (see, e.g., seq 2c); in some embodiments, the sequence includes amino acids 1418-2136 of Tet1 or the corresponding region in Tet2/3.

Other catalytic modules can be from the proteins identified in Iyer et al., 2009.

In some embodiments, the heterologous functional domain is a biological tether, and comprises all or part of (e.g., DNA binding domain from) the MS2 coat protein, endoribonuclease Csy4, or the lambda N protein. These proteins can be used to recruit RNA molecules containing a specific stem-loop structure to a locale specified by the dCpf1 gRNA targeting sequences. For example, a dCpf1 variant fused to MS2 coat protein, endoribonuclease Csy4, or lambda N can be used to recruit a long non-coding RNA (lncRNA) such as XIST or HOTAIR; see, e.g., Keryer-Bibens et al., Biol. Cell 100:125-138 (2008), that is linked to the Csy4, MS2 or lambda N binding sequence. Alternatively, the Csy4, MS2 or lambda N protein binding sequence can be linked to another protein, e.g., as described in Keryer-Bibens et al., supra, and the protein can be targeted to the dCpf1 variant binding site using the methods and compositions described herein. In some embodiments, the Csy4 is catalytically inactive. In some embodiments, the Cpf1 variant, preferably a dCpf1 variant, is fused to FokI as described in U.S. Pat. No. 8,993,233; US20140186958; U.S. Pat. No. 9,023,649; WO/2014/099744; WO 2014/089290; WO2014/144592; WO144288; WO2014/204578; WO2014/152432; WO2115/099850; U.S. Pat. No. 8,697,359; US2010/0076057; US2011/0189776; US2011/0223638; US2013/0130248; WO/2008/108989; WO/2010/054108; WO/2012/164565; WO/2013/098244; WO/2013/176772; US20150050699; US20150071899 and WO 2014/204578.

In some embodiments, the fusion proteins include a linker between the Cpf1 variant and the heterologous functional domains. Linkers that can be used in these fusion proteins (or between fusion proteins in a concatenated structure) can include any sequence that does not interfere with the function of the fusion proteins. In preferred embodiments, the linkers are short, e.g., 2-20 amino acids, and are typically flexible (i.e., comprising amino acids with a high degree of freedom such as glycine, alanine, and serine). In some embodiments, the linker comprises one or more units consisting of GGGS (SEQ ID NO:195) or GGGGS (SEQ ID NO:192), e.g., two, three, four, or more repeats of the GGGS (SEQ ID NO: 195) or GGGGS (SEQ ID NO: 192) unit. Other linker sequences can also be used.

In some embodiments, the variant protein includes a cell-penetrating peptide sequence that facilitates delivery to the intracellular space, e.g., HIV-derived TAT peptide, penetratins, transportans, or hCT derived cell-penetrating peptides, see, e.g., Caron et al., (2001) Mol Ther. 3(3):310-8; Langel, Cell-Penetrating Peptides: Processes and Applications (CRC Press, Boca Raton FL 2002); El-Andaloussi et al., (2005) Curr Pharm Des. 11(28):3597-611; and Deshayes et al., (2005) Cell Mol Life Sci. 62(16):1839-49.

Cell penetrating peptides (CPPs) are short peptides that facilitate the movement of a wide range of biomolecules across the cell membrane into the cytoplasm or other organelles, e.g. the mitochondria and the nucleus. Examples of molecules that can be delivered by CPPs include therapeutic drugs, plasmid DNA, oligonucleotides, siRNA, peptide-nucleic acid (PNA), proteins, peptides, nanoparticles, and liposomes. CPPs are generally 30 amino acids or less, are derived from naturally or non-naturally occurring protein or chimeric sequences, and contain either a high relative abundance of positively charged amino acids, e.g. lysine or arginine, or an alternating pattern of polar and non-polar amino acids. CPPs that are commonly used in the art include Tat (Frankel et al., (1988) Cell. 55:1189-1193, Vives et al., (1997) J. Biol. Chem. 272:16010-16017), penetratin (Derossi et al., (1994) J. Biol. Chem. 269:10444-10450), polyarginine peptide sequences (Wender et al., (2000) Proc. Natl. Acad. Sci. USA 97:13003-13008, Futaki et al., (2001) J. Biol. Chem. 276:5836-5840), and transportan (Pooga et al., (1998) Nat. Biotechnol. 16:857-861).

CPPs can be linked with their cargo through covalent or non-covalent strategies. Methods for covalently joining a CPP and its cargo are known in the art, e.g. chemical cross-linking (Stetsenko et al., (2000) J. Org. Chem. 65:4900-4909, Gait et al. (2003) Cell. Mol. Life. Sci. 60:844-853) or cloning a fusion protein (Nagahara et al., (1998) Nat. Med. 4:1449-1453). Non-covalent coupling between the cargo and short amphipathic CPPs comprising polar and non-polar domains is established through electrostatic and hydrophobic interactions.

CPPs have been utilized in the art to deliver potentially therapeutic biomolecules into cells. Examples include cyclosporine linked to polyarginine for immunosuppression (Rothbard et al., (2000) Nature Medicine 6(11):1253-1257), siRNA against cyclin B1 linked to a CPP called MPG for inhibiting tumorigenesis (Crombez et al., (2007) Biochem Soc. Trans. 35:44-46), tumor suppressor p53 peptides linked to CPPs to reduce cancer cell growth (Takenobu et al., (2002) Mol. Cancer Ther. 1(12):1043-1049, Snyder et al., (2004) PLOS Biol. 2:E36), and dominant negative forms of Ras or phosphoinositol 3 kinase (PI3K) fused to Tat to treat asthma (Myou et al., (2003) J. Immunol. 171:4399-4405).

CPPs have been utilized in the art to transport contrast agents into cells for imaging and biosensing applications. For example, green fluorescent protein (GFP) attached to Tat has been used to label cancer cells (Shokolenko et al., (2005) DNA Repair 4(4):511-518). Tat conjugated to quantum dots have been used to successfully cross the blood-brain barrier for visualization of the rat brain (Santra et al., (2005) Chem. Commun. 3144-3146). CPPs have also been combined with magnetic resonance imaging techniques for cell imaging (Liu et al., (2006) Biochem. and Biophys. Res. Comm. 347(1):133-140). See also Ramsey and Flynn, Pharmacol Ther. 2015 Jul. 22. pii: S0163-7258(15) 00141-2.

Alternatively or in addition, the variant proteins can include a nuclear localization sequence, e.g., SV40 large T antigen NLS (PKKKRRV (SEQ ID NO:193)) and nucleoplasmin NLS (KRPAATKKAGQAKKKK (SEQ ID NO:194)). Other NLSs are known in the art; see, e.g., Cokol et al., EMBO Rep. 2000 Nov. 15; 1(5): 411-415; Freitas and Cunha, Curr Genomics. 2009 December; 10(8): 550-557.

In some embodiments, the variants include a moiety that has a high affinity for a ligand, for example GST, FLAG or hexahistidine sequences (SEQ ID NO: 196). Such affinity tags can facilitate the purification of recombinant variant proteins.

For methods in which the variant proteins are delivered to cells, the proteins can be produced using any method known in the art, e.g., by in vitro translation, or expression in a suitable host cell from nucleic acid encoding the variant protein; a number of methods are known in the art for producing proteins. For example, the proteins can be produced in and purified from yeast, *E. coli*, insect cell lines, plants, transgenic animals, or cultured mammalian cells; see, e.g., Palomares et al., "Production of Recombinant Proteins: Challenges and Solutions," Methods Mol Biol. 2004; 267: 15-52. In addition, the variant proteins can be linked to a moiety that facilitates transfer into a cell, e.g., a lipid nanoparticle, optionally with a linker that is cleaved once the protein is inside the cell. See, e.g., LaFountaine et al., Int J Pharm. 2015 Aug. 13; 494(1):180-194.

Expression Systems

To use the Cpf1 variants described herein, it may be desirable to express them from a nucleic acid that encodes them. This can be performed in a variety of ways. For example, the nucleic acid encoding the Cpf1 variant can be cloned into an intermediate vector for transformation into prokaryotic or eukaryotic cells for replication and/or expression. Intermediate vectors are typically prokaryote vectors, e.g., plasmids, or shuttle vectors, or insect vectors, for storage or manipulation of the nucleic acid encoding the Cpf1 variant for production of the Cpf1 variant. The nucleic acid encoding the Cpf1 variant can also be cloned into an expression vector, for administration to a plant cell, animal cell, preferably a mammalian cell or a human cell, fungal cell, bacterial cell, or protozoan cell.

To obtain expression, a sequence encoding a Cpf1 variant is typically subcloned into an expression vector that contains a promoter to direct transcription. Suitable bacterial and eukaryotic promoters are well known in the art and described, e.g., in Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 2010). Bacterial expression systems for expressing the engineered protein are available in, e.g., *E. coli, Bacillus* sp., and *Salmonella* (Palva et al., 1983, Gene 22:229-235). Kits for such expression systems are commercially available. Eukaryotic expression systems for mammalian cells, yeast, and insect cells are well known in the art and are also commercially available.

The promoter used to direct expression of a nucleic acid depends on the particular application. For example, a strong constitutive promoter is typically used for expression and purification of fusion proteins. In contrast, when the Cpf1 variant is to be administered in vivo for gene regulation, either a constitutive or an inducible promoter can be used, depending on the particular use of the Cpf1 variant. In addition, a preferred promoter for administration of the Cpf1 variant can be a weak promoter, such as HSV TK or a promoter having similar activity. The promoter can also include elements that are responsive to transactivation, e.g., hypoxia response elements, Gal4 response elements, lac repressor response element, and small molecule control systems such as tetracycline-regulated systems and the RU-486 system (see, e.g., Gossen & Bujard, 1992, Proc. Natl. Acad. Sci. USA, 89:5547; Oligino et al., 1998, Gene Ther., 5:491-496; Wang et al., 1997, Gene Ther., 4:432-441; Neering et al., 1996, Blood, 88:1147-55; and Rendahl et al., 1998, Nat. Biotechnol., 16:757-761).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the Cpf1 variant, and any signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the Cpf1 variant, e.g., expression in plants, animals, bacteria, fungus, protozoa, etc. Standard bacterial expression vectors include plasmids such as pBR322 based plasmids, pSKF, pET23D, and commercially available tag-fusion expression systems such as GST and LacZ.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

The vectors for expressing the Cpf1 variants can include RNA Pol III promoters to drive expression of the guide RNAs, e.g., the H1, U6 or 7SK promoters. These human promoters allow for expression of Cpf1 variants in mammalian cells following plasmid transfection.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with the gRNA encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., 1989, J. Biol. Chem., 264:17619-22; Guide to Protein Purification, in Methods in Enzymology, vol. 182 (Deutscher, ed., 1990)). Transformation of eukaryotic and prokaryotic cells are performed according to standard techniques (see, e.g., Morrison, 1977, J. Bacteriol. 132:349-351; Clark-Curtiss & Curtiss, Methods in Enzymology 101:347-362 (Wu et al., eds, 1983).

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the Cpf1 variant.

The present invention also includes the vectors and cells comprising the vectors.

EXAMPLES

The invention is further described in the following examples, which do not limit the scope of the invention described in the claims.

Sequences

The following constructs were used in the Examples below.

---

```
Nucleotide sequence of pCAG-humanAsCpf1-NLS-3xHA
Human codon optimized AsCpf1 in normal font (NTs 1-3921), NLS in lower case
(aaaaggccggcggccacgaaaaaggccggccaggcaaaaaagaaaaag, SEQ ID NO: 3), 3xHA tag
(TACCCATACGATGTTCCAGATTACGCTTATCCCTACGACGTGCCTGATTATGCATACCCATAT
GATGTCCCCGACTATGCC, SEQ ID NO: 4) in bold
ATGACACAGTTCGAGGGCTTTACCAACCTGTATCAGGTGAGCAAGACACTGCGGTTTGAGCTGATCCCACAG
GGCAAGACCCTGAAGCACATCCAGGAGCAGGGCTTCATCGAGGAGGACAAGGCCCGCAATGATCACTACAAGGAGCT
```

-continued

GAAGCCCATCATCGATCGGATCTACAAGACCTATGCCGACCAGTGCCTGCAGCTGGTGCAGCTGGATTGGGAGAACCT
GAGCGCCGCCATCGACTCCTATAGAAAGGAGAAAACCGAGGAGACAAGGAACGCCCTGATCGAGGAGCAGGCCACAT
ATCGCAATGCCATCCACGACTACTTCATCGGCCGGACAGACAACCTGACCGATGCCATCAATAAGAGACACGCCGAGA
TCTACAAGGGCCTGTTCAAGGCCGAGCTGTTTAATGGCAAGGTGCTGAAGCAGCTGGGCACCGTGACCACAACCGAG
CACGAGAACGCCCTGCTGCGGAGCTTCGACAAGTTTACAACCTACTTCTCCGGCTTTTATGAGAACAGGAAGAACGTG
TTCAGCGCCGAGGATATCAGCACAGCCATCCCACACCGCATCGTGCAGGACAACTTCCCCAAGTTTAAGGAGAATTGT
CACATCTTCACACGCCTGATCACCGCCGTGCCCAGCCTGCGGGAGCACTTTGAGAACGTGAAGAAGGCCATCGGCAT
CTTCGTGAGCACCTCCATCGAGGAGGTGTTTTCCTTCCCTTTTTATAACCAGCTGCTGACACAGACCCAGATCGACCTG
TATAACCAGCTGCTGGGAGGAATCTCTCGGGAGGCAGGCACCGAGAAGATCAAGGGCCTGAACGAGGTGCTGAATCT
GGCCATCCAGAAGAATGATGAGACAGCCCACATCATCGCCTCCCTGCCACACAGATTCATCCCCCTGTTTAAGCAGAT
CCTGTCCGATAGGAACACCCTGTCTTTCATCCTGGAGGAGTTTAAGAGCGACGAGGAAGTGATCCAGTCCTTCTGCAA
GTACAAGACACTGCTGAGAAACGAGAACGTGCTGGAGACAGCCGAGGCCCTGTTTAACGAGCTGAACAGCATCGACC
TGACACACATCTTCATCAGCCACAAGAAGCTGGAGACAATCAGCAGCGCCCTGTGCGACCACTGGGATACACTGAGGA
ATGCCCTGTATGAGCGGAGAATCTCCGAGCTGACAGGCAAGATCACCAAGTCTGCCAAGGAGAAGGTGCAGCGCAGC
CTGAAGCACGAGGATATCAACCTGCAGGAGATCATCTCTGCCGCAGGCAAGGAGCTGAGCGAGGCCTTCAAGCAGAA
AACCAGCGAGATCCTGTCCCACGCACACGCCGCCCTGGATCAGCCACTGCCTACAACCCTGAAGAAGCAGGAGGAGA
AGGAGATCCTGAAGTCTCAGCTGGACAGCCTGCTGGGCCTGTACCACCTGCTGGACTGGTTTGCCGTGGATGAGTCC
AACGAGGTGGACCCCGAGTTCTCTGCCCGGCTGACCGGCATCAAGCTGGAGATGGAGCCTTCTCTGAGCTTCTACAA
CAAGGCCAGAAATTATGCCACCAAGAAGCCCTACTCCGTGGAGAAGTTCAAGCTGAACTTTCAGATGCCTACACTGGC
CTCTGGCTGGGACGTGAATAAGGAGAAGAACAATGGCGCCATCCTGTTTGTGAAGAACGGCCTGTACTATCTGGGCAT
CATGCCAAAGCAGAAGGGCAGGTATAAGGCCCTGAGCTTCGAGCCCACAGAGAAAACCAGCGAGGGCTTTGATAAGA
TGTACTATGACTACTTCCCTGATGCCGCCAAGATGATCCCAAAGTGCAGCACCCAGCTGAAGGCCGTGACAGCCCACT
TTCAGACCCACACAACCCCCATCCTGCTGTCCAACAATTTCATCGAGCCTCTGGAGATCACAAAGGAGATCTACGACCT
GAACAATCCTGAGAAGGAGCCAAAGAAGTTTCAGACAGCCTACGCCAAGAAAACCGGCGACCAGAAGGGCTACAGAG
AGGCCCTGTGCAAGTGGATCGACTTCACAAGGGATTTTCTGTCCAAGTATACCAAGACAACCTCTATCGATCTGTCTAG
CCTGCGGCCATCCTCTCAGTATAAGGACCTGGGCGAGTACTATGCCGAGCTGAATCCCCTGCTGTACCACATCAGCTT
CCAGAGAATCGCCGAGAAGGAGATCATGGATGCCGTGGAGACAGGCAAGCTGTACCTGTTCCAGATCTATAACAAGGA
CTTTGCCAAGGGCCACCACGGCAAGCCTAATCTGCACACACTGTATTGGACCGGCCTGTTTTCTCCAGAGAACCTGGC
CAAGACAAGCATCAAGCTGAATGGCCAGGCCGAGCTGTTCTACCGCCCTAAGTCCAGGATGAAGAGGATGGCACACC
GGCTGGGAGAGAAGATGCTGAACAAGAAGCTGAAGGATCAGAAAACCCCAATCCCCGACACCCTGTACCAGGAGCTG
TACGACTATGTGAATCACAGACTGTCCCACGACCTGTCTGATGAGGCCAGGGCCCTGCTGCCCAACGTGATCACCAAG
GAGGTGTCTCACGAGATCATCAAGGATAGGCGCTTTACCAGCGACAAGTTCTTTTTCCACGTGCCTATCACACTGAACT
ATCAGGCCGCCAATTCCCCATCTAAGTTCAACCAGAGGGTGAATGCCTACCTGAAGGAGCACCCCGAGACACCTATCA
TCGGCATCGATCGGGGCGAGAGAAACCTGATCTATATCACAGTGATCGACTCCACCGGCAAGATCCTGGAGCAGCGG
AGCCTGAACACCATCCAGCAGTTTGATTACCAGAAGAAGCTGGACAACAGGGAGAAGGAGAGGGTGGCAGCAAGGCA
GGCCTGGTCTGTGGTGGGCACAATCAAGGATCTGAAGCAGGGCTATCTGAGCCAGGTCATCCACGAGATCGTGGACC
TGATGATCCACTACCAGGCCGTGGTGGTGCTGGAGAACCTGAATTTCGGCTTTAAGAGCAAGAGGACCGGCATCGCC
GAGAAGGCCGTGTACCAGCAGTTCGAGAAGATGCTGATCGATAAGCTGAATTGCCTGGTGCTGAAGGACTATCCAGCA
GAGAAAGTGGGAGGCGTGCTGAACCCATACCAGCTGACAGACCAGTTCACCTCCTTTGCCAAGATGGGCACCCAGTCT
GGCTTCCTGTTTTACGTGCCTGCCCCATATACATCTAAGATCGATCCCCTGACCGGCTTCGTGGACCCCTTCGTGTGGA
AAACCATCAAGAATCACGAGAGCCGCAAGCACTTCCTGGAGGGCTTCGACTTTCTGCACTACGACGTGAAAACCGGCG
ACTTCATCCTGCACTTTAAGATGAACAGAAATCTGTCCTTCCAGAGGGGCCTGCCCGGCTTTATGCCTGCATGGGATAT
CGTGTTCGAGAAGAACGAGACACAGTTTGACGCCAAGGGCACCCCTTTCATCGCCGGCAAGAGAATCGTGCCAGTGAT
CGAGAATCACAGATTCACCGGCAGATACCGGGACCTGTATCCTGCCAACGAGCTGATCGCCCTGCTGGAGGAGAAGG
GCATCGTGTTCAGGGATGGCTCCAACATCCTGCCAAAGCTGCTGGAGAATGACGATTCTCACGCCATCGACACCATGG
TGGCCCTGATCCGCAGCGTGCTGCAGATGCGGAACTCCAATGCCGCCACAGGCGAGGACTATATCAACAGCCCCGTG
CGCGATCTGAATGGCGTGTGCTTCGACTCCCGGTTTCAGAACCCAGAGTGGCCCATGGACGCCGATGCCAATGGCGC
CTACCACATCGCCCTGAAGGGCCAGCTGCTGCTGAATCACCTGAAGGAGAGCAAGGATCTGAAGCTGCAGAACGGCA
TCTCCAATCAGGACTGGCTGGCCTACATCCAGGAGCTGCGCAACcaaaaggccggeggccacgaaaaaggccggccaggcaaaaaaagaa
aaagGGATCCTACCCATACGATGTTCCAGATTACGCTTATCCCTACGACGTGCCTGATTATGCATACCCATATGATGTC
CCCGACTATGCCTAA (SEQ ID NO: 5)

Amino acid sequence of AsCpf1-NLS-3xHA
AsCpf1 in normal font (AAs 1-1306), NLS (krpaatkkagqakkkkgs, SEQ ID NO: 6) in lower case, 3xHA tag (YPYDVPDYAYPYDVPDYAYPYDVPDYA, SEQ ID NO: 7) in bold
MTQFEGFTNLYQVSKTLRFELIPQGKTLKHIQEQGFIEEDKARNDHYKELKPIIDRIYKTYADQCLQLVQLDWENLS
AAIDSYRKEKTEETRNALIEEQATYRNAIHDYFIGRTDNLTDAINKRHAEIYKGLFKAELFNGKVLKQLGTVTTTEHENALLRSF
DKFTTYFSGFYENRKNVFSAEDISTAIPHRIVQDNFPKFKENCHIFTRLITAVPSLREHFENVKKAIGIFVSTSIEEVFSFPFYNQ
LLTQTQIDLYNQLLGGISREAGTEKIKGLNEVLNLAIQKNDETAHIIASLPHRFIPLFKQILSDRNTLSFILEEFKSDEEVIQSFCKY
KTLLRNENVLETAEALFNELNSIDLTHIFISHKKLETISSALCDHWDTLRNALYERRISELTGKITKSAKEKVQRSLKHEDINLQEI
ISAAGKELSEAFKQKTSEILSHAHAALDQPLPTTLKKQEEKEILKSQLDSLLGLYHLLDWFAVDESNEVDPEFSARLTGIKLEM
EPSLSFYNKARNYATKKPYSVEKFKLNFQMPTLASGWDVNKEKNNGAILFVKNGLYYLGIMPKQKGRYKALSFEPTEKTSEG
FDKMYYDYFPDAAKMIPKCSTQLKAVTAHFQTHTTPILLSNNFIEPLEITKEIYDLNNPEKEPKKFQTAYAKKTGDQKGYREAL
CKWIDFTRDFLSKYTKTTSIDLSSLRPSSQYKDLGEYYAELNPLLYHISFQRIAEKEIMDAVETGKLYLFQIYNKDFAKGHHGKP
NLHTLYWTGLFSPENLAKTSIKLNGQAELFYRPKSRMKRMAHRLGEKMLNKKLKDQKTPIPDTLYQELYDYVNHRLSHDLSD
EARALLPNVITKEVSHEIIKDRRFTSDKFFFHVPITLNYQAANSPSKFNQRVNAYLKEHPETPIIGIDRGERNLIYITVIDSTGKILE
QRSLNTIQQFDYQKKLDNREKERVAARQAWSVVGTIKDLKQGYLSQVIHEIVDLMIHYQAVVVLENLNFGFKSKRTGIAEKAV
YQQFEKMLIDKLNCLVLKDYPAEKVGGVLNPYQLTDQFTSFAKMGTQSGFLFYVPAPYTSKIDPLTGFVDPFVWKTIKNHES
RKHFLEGFDFLHYDVKTGDFILHFKMNRNLSFQRGLPGFMPAWDIVFEKNETQFDAKGTPFIAGKRIVPVIENHRFTGRYRDL
YPANELIALLEEKGIVFRDGSNILPKLLENDDSHAIDTMVALIRSVLQMRNSNAATGEDYINSPVRDLNGVCFDSRFQNPEWP
MDADANGAYHIALKGQLLLNHLKESKDLKLQNGISNQDWLAYIQELRNkrpaatkkaggakkkkgsYPYDVPDYAYPYDVPDYAYP
YDVPDYA (SEQ ID NO: 8)

-continued

Nucleotide sequence of SQT1665 pCAG-humanLbCpf1-NLS-3xHA
Human codon optimized LbCpf1 in normal font, nts 1-3684), NLS
(aaaaggccggcggccacgaaaaaggccggccaggcaaaaaagaaaaag, SEQ ID NO: 3) in lower case, 3xHA
tag
(TACCCATACGATGTTCCAGATTACGCTTATCCCTACGACGTGCCTGATTATGCATACCCATAT
GATGTCCCCGACTATGCC, SEQ ID NO: 4) in BOLD
ATGAGCAAGCTGGAGAAGTTTACAAACTGCTACTCCCTGTCTAAGACCCTGAGGTTCAAGGCCATCCCTGTG
GGCAAGACCCAGGAGAACATCGACAATAAGCGGCTGCTGGTGGAGGACGAGAAGAGAGCCGAGGATTATAAGGGCGT
GAAGAAGCTGCTGGATCGCTACTATCTGTCTTTTATCAACGACGTGCTGCACAGCATCAAGCTGAAGAATCTGAACAAT
TACATCAGCCTGTTCCGGAAGAAAACCAGAACCGAGAAGGAGAATAAGGAGCTGGAGAACCTGGAGATCAATCTGCGG
AAGGAGATCGCCAAGGCCTTCAAGGGCAACGAGGGCTACAAGTCCCTGTTTAAGAAGGATATCATCGAGACAATCCTG
CCAGAGTTCCTGGACGATAAGGACGAGATCGCCCTGGTGAACAGCTTCAATGGCTTTACCACAGCCTTCACCGGCTTC
TTTGATAACAGAGAGAATATGTTTTCCGAGGAGGCCAAGAGCACATCCATCGCCTTCAGGTGTATCAACGAGAATCTGA
CCCGCTACATCTCTAATATGGACATCTTCGAGAAGGTGGACGCCATCTTTGATAAGCACGAGGTGCAGGAGATCAAGG
AGAAGATCCTGAACAGCGACTATGATGTGGAGGATTTCTTTGAGGGCGAGTTCTTTAACTTTGTGCTGACACAGGAGG
GCATCGACGTGTATAACGCCATCATCGGCGGCTTCGTGACCGAGAGCGGCGAGAAGATCAAGGGCCTGAACGAGTAC
ATCAACCTGTATAATCAGAAAACCAAGCAGAAGCTGCCTAAGTTTAAGCCACTGTATAAGCAGGTGCTGAGCGATCGGG
AGTCTCTGAGCTTCTACGGCGAGGGCTATACATCCGATGAGGAGGTGCTGGAGGTGTTTAGAAACACCCTGAACAAGA
ACAGCGAGATCTTCAGCTCCATCAAGAAGCTGGAGAAGCTGTTCAAGAATTTTGACGAGTACTCTAGCGCCGGCATCTT
TGTGAAGAACGGCCCCGCCATCAGCACAATCTCCAAGGATATCTTCGGCGAGTGGAACGTGATCCGGGACAAGTGGA
ATGCCGAGTATGACGATATCCACCTGAAGAAGAAGGCCGTGGTGACCGAGAAGTACGAGGACGATCGGAGAAAGTCC
TTCAAGAAGATCGGCTCCTTTTCTCTGGAGCAGCTGCAGGAGTACGCCGACGCCGATCTGTCTGTGGTGGAGAAGCTG
AAGGAGATCATCATCCAGAAGGTGGATGAGATCTACAAGGTGTATGGCTCCTCTGAGAAGCTGTTCGACGCCGATTTT
GTGCTGGAGAAGAGCCTGAAGAAGAACGACGCCGTGGTGGCCATCATGAAGGACCTGCTGGATTCTGTGAAGAGCTT
CGAGAATTACATCAAGGCCTTCTTTGGCGAGGGCAAGGAGACAAACAGGGACGAGTCCTTCTATGGCGATTTTGTGCT
GGCCTACGACATCCTGCTGAAGGTGGACCACATCTACGATGCCATCCGCAATTATGTGACCCAGAAGCCCTACTCTAA
GGATAAGTTCAAGCTGTATTTTCAGAACCCTCAGTTCATGGGCGGCTGGGACAAGGATAAGGAGACAGACTATCGGGC
CACCATCCTGAGATACGGCTCCAAGTACTATCTGGCCATCATGGATAAGAAGTACGCCAAGTGCCTGCAGAAGATCGA
CAAGGACGATGTGAACGGCAATTACGAGAAGATCAACTATAAGCTGCTGCCCGGCCCTAATAAGATGCTGCCAAAGGT
GTTCTTTTCTAAGAAGTGGATGGCCTACTATAACCCCAGCGAGGACATCCAGAAGATCTACAAGAATGGCACATTCAAG
AAGGGCGATATGTTTAACCTGAATGACTGTCACAAGCTGATCGACTTCTTTAAGGATAGCATCTCCCGGTATCCAAAGT
GGTCCAATGCCTACGATTTCAACTTTTCTGAGACAGAGAAGTATAAGGACATCGCCGGCTTTTACAGAGAGGTGGAGG
AGCAGGGCTATAAGGTGAGCTTCGAGTCTGCCAGCAAGAAGGAGGTGGATAAGCTGGTGGAGGAGGGCAAGCTGTAT
ATGTTCCAGATCTATAACAAGGACTTTTCCGATAAGTCTCACGGCACACCCAATCTGCACACCATGTACTTCAAGCTGCT
GTTTGACGAGAACAATCACGGACAGATCAGGCTGAGCGGAGGAGCAGAGCTGTTCATGAGGCGCGCCTCCCTGAAGA
AGGAGGAGCTGGTGGTGCACCCAGCCAACTCCCCTATCGCCAACAAGAATCCAGATAATCCCAAGAAAACCACAACCC
TGTCCTACGACGTGTATAAGGATAAGAGGTTTTCTGAGGACCAGTACGAGCTGCACATCCCAATCGCCATCAATAAGTG
CCCCAAGAACATCTTCAAGATCAATACAGAGGTGCGCGTGCTGCTGAAGCACGACGATAACCCCTATGTGATCGGCAT
CGATAGGGGCGAGCGCAATCTGCTGTATATCGTGGTGGTGGACGGCAAGGGCAACATCGTGGAGCAGTATTCCCTGA
ACGAGATCATCAACAACTTCAACGGCATCAGGATCAAGACAGATTACCACTCTCTGCTGGACAAGAAGGAGAAGGAGA
GGTTCGAGGCCCGCCAGAACTGGACCTCCATCGAGAATATCAAGGAGCTGAAGGCCGGCTATATCTCTCAGGTGGTG
CACAAGATCTGCGAGCTGGTGGAGAAGTACGATGCCGTGATCGCCCTGGAGGACCTGAACTCTGGCTTTAAGAATAGC
CGCGTGAAGGTGGAGAAGCAGGTGTATCAGAAGTTCGAGAAGATGCTGATCGATAAGCTGAACTACATGGTGGACAAG
AAGTCTAATCCTTGTGCAACAGGCGGCGCCCTGAAGGGCTATCAGATCACCAATAAGTTCGAGAGCTTTAAGTCCATGT
CTACCCAGAACGGCTTCATCTTTTACATCCCTGCCTGGCTGACATCCAAGATCGATCCATCTACCGGCTTTGTGAACCT
GCTGAAAACCAAGTATACCAGCATCGCCGATTCCAAGAAGTTCATCAGCTCCTTTGACAGGATCATGTACGTGCCCGAG
GAGGATCTGTTCGAGTTTGCCCTGGACTATAAGAACTTCTCTCGCACAGACGCCGATTACATCAAGAAGTGGAAGCTGT
ACTCCTACGGCAACCGGATCAGAATCTTCCGGAATCCTAAGAAGAACAACGTGTTCGACTGGGAGGAGGTGTGCCTGA
CCAGCGCCTATAAGGAGCTGTTCAACAAGTACGGCATCAATTATCAGCAGGGCGATATCAGAGCCCTGCTGTGCGAGC
AGTCCGACAAGGCCTTCTACTCTAGCTTTATGGCCCTGATGAGCCTGATGCTGCAGATGCGGAACAGCATCACAGGCC
GCACCGACGTGGATTTTCTGATCAGCCCTGTGAAGAACTCCGACGGCATCTTCTACGATAGCCGGAACTATGAGGCCC
AGGAGAATGCCATCCTGCCAAAGAACGCCGACGCCAATGGCGCCTATAACATCGCCAGAAAGGTGCTGTGGGCCATC
GGCCAGTTCAAGAAGGCCGAGGACGAGAAGCTGGATAAGGTGAAGATCGCCATCTCTAACAAGGAGTGGCTGGAGTA
CGCCCAGACCAGCGTGAAGCACaaaaggccggcggccacgaaaaaggccggccaggcaaaaaagaaaaagGGATCCTACCCATACGAT
GTTCCAGATTACGCTTATCCCTACGACGTGCCTGATTATGCATACCCATATGATGTCCCCGACTATGCCTAA (SEQ ID
NO: 9)

Amino acid sequence of LbCpf1-NLS-3xHA
LbCpf1 in normal text (AAs 1-1228), NLS (krpaatkkagqakkkkgs, SEQ ID NO: 6) in lower
case, 3xHA tag (YPYDVPDYAYPYDVPDYAYPYDVPDYA, SEQ ID NO: 7) in bold
MSKLEKFTNCYSLSKTLRFKAIPVGKTQENIDNKRLLVEDEKRAEDYKGVKKLLDRYYLSFINDVLHSIKLKNLNNYI
SLFRKKTRTEKENKELENLEINLRKEIAKAFKGNEGYKSLFKKDIIETILPEFLDDKDEIALVNSFNGFTTAFTGFFDNRENMFSE
EAKSTSIAFRCINENLTRYISNMDIFEKVDAIFDKHEVQEIKEKILNSDYDVEDFFEGEFFNFVLTQEGIDVYNAIIGGFVTESGE
KIKGLNEYINLYNQKTKQKLPKFKPLYKQVLSDRESLSFYGEGYTSDEEVLEVFRNTLNKNSEIFSSIKKLEKLFKNFDEYSSA
GIFVKNGPAISTISKDIFGEWNVIRDKWNAEYDDIHLKKKAVVTEKYEDDRRKSFKKIGSFSLEQLQEYADADLSVVEKLKEIIIQ
KVDEIYKVYGSSEKLFDADFVLEKSLKKNDAVVAIMKDLLDSVKSFENYIKAFFGEGKETNRDESFYGDFVLAYDILLKVDHIY
DAIRNYVTQKPYSKDKFKLYFQNPQFMGGWDKDKETDYRATILRYGSKYYLAIMDKKYAKCLQKIDKDDVNGNYEKINYKLL
PGPNKMLPKVFFSKKWMAYYNPSEDIQKIYKNGTFKKGDMFNLNDCHKLIDFFKDSISRYPKWSNAYDFNFSETEKYKDIAG
FYREVEEQGYKVSFESASKKEVDKLVEEGKLYMFQIYNKDFSDKSHGTPNLHTMYFKLLFDENNHGQIRLSGGAELFMRRA
SLKKEELVVHPANSPIANKNPDNPKKTTTLSYDVYKDKRFSEDQYELHIPIAINKCPKNIFKINTEVRVLLKHDDNPYVIGIDRGE -continued RNLLYIVVVDGKGNIVEQYSLNEIINNFNGIRIKTDYHSLLDKKEKERFEARQNWTSIENIKELKAGYISQVVHKICELVEKYDAVI
ALEDLNSGFKNSRVKVEKQVYQKFEKMLIDKLNYMVDKKSNPCATGGALKGYQITNKFESFKSMSTQNGFIFYIPAWLTSKID
PSTGFVNLLKTKYTSIADSKKFISSFDRIMYVPEEDLFEFALDYKNFSRTDADYIKKWKLYSYGNRIRIFRNPKKNNVFDWEEV
CLTSAYKELFNKYGINYQQGDIRALLCEQSDKAFYSSFMALMSLMLQMRNSITGRTDVDFLISPVKNSDGIFYDSRNYEAQEN
AILPKNADANGAYNIARKVLWAIGQFKKAEDEKLDKVKIAISNKEWLEYAQTSVKHkrpaatkkagqakkkkgs**YPYDVPDYAYPYD
VPDYAYPYDVPDYA** (SEQ ID NO: 10)

Cpf1 crRNAs

| Name DNMT1 | Spacer length (nt) | Sequence with Cpf1 PAM at 5' end (TTTC/TTTA/TTTG) | SEQ ID NO |
|---|---|---|---|
| DNMT1 site 1 | 23 | TTTCCCTCACTCCTGCTCGGTGAATTT | 11. |
| DNMT1 site 1 mm 1 & 2 | 23 | TTTCggTCACTCCTGCTCGGTGAATTT | 12. |
| DNMT1 site 1 mm 3 & 4 | 23 | TTTCCCagACTCCTGCTCGGTGAATTT | 13. |
| DNMT1 site 1 mm 5 & 6 | 23 | TTTCCCTCtgTCCTGCTCGGTGAATTT | 14. |
| DNMT1 site 1 mm 7 & 8 | 23 | TTTCCCTCACagCTGCTCGGTGAATTT | 15. |
| DNMT1 site 1 mm 9 & 10 | 23 | TTTCCCTCACTCgaGCTCGGTGAATTT | 16. |
| DNMT1 site 1 mm 11 & 12 | 23 | TTTCCCTCACTCCTcgTCGGTGAATTT | 17. |
| DNMT1 site 1 mm 13 & 14 | 23 | TTTCCCTCACTCCTGCagGGTGAATTT | 18. |
| DNMT1 site 1 mm 15 & 16 | 23 | TTTCCCTCACTCCTGCTCccTGAATTT | 19. |
| DNMT1 site 1 mm 17 & 18 | 23 | TTTCCCTCACTCCTGCTCGGacAATTT | 20. |
| DNMT1 site 1 mm 19 & 20 | 23 | TTTCCCTCACTCCTGCTCGGTGttTTT | 21. |
| DNMT1 site 1 mm 21 & 22 | 23 | TTTCCCTCACTCCTGCTCGGTGAAaaT | 22. |
| DNMT1 site 1 mm 22 & 23 | 23 | TTTCCCTCACTCCTGCTCGGTGAATaa | 23. |
| DNMT1 site 1 mm 1 | 23 | TTTCgCTCACTCCTGCTCGGTGAATTT | 24. |
| DNMT1 site 1 mm 2 | 23 | TTTCCgTCACTCCTGCTCGGTGAATTT | 25. |
| DNMT1 site 1 mm 3 | 23 | TTTCCCaCACTCCTGCTCGGTGAATTT | 26. |
| DNMT1 site 1 mm 4 | 23 | TTTCCCTgACTCCTGCTCGGTGAATTT | 27. |
| DNMT1 site 1 mm 5 | 23 | TTTCCCTCtCTCCTGCTCGGTGAATTT | 28. |
| DNMT1 site 1 mm 6 | 23 | TTTCCCTCAgTCCTGCTCGGTGAATTT | 29. |
| DNMT1 site 1 mm 7 | 23 | TTTCCCTCACaCCTGCTCGGTGAATTT | 30. |
| DNMT1 site 1 mm 8 | 23 | TTTCCCTCACTgCTGCTCGGTGAATTT | 31. |
| DNMT1 site 1 mm 9 | 23 | TTTCCCTCACTCgTGCTCGGTGAATTT | 32. |
| DNMT1 site 1 mm 10 | 23 | TTTCCCTCACTCCaGCTCGGTGAATTT | 33. |
| DNMT1 site 1 mm 11 | 23 | TTTCCCTCACTCCTcCTCGGTGAATTT | 34. |
| DNMT1 site 1 mm 12 | 23 | TTTCCCTCACTCCTGgTCGGTGAATTT | 35. |
| DNMT1 site 1 mm 13 | 23 | TTTCCCTCACTCCTGCaCGGTGAATTT | 36. |
| DNMT1 site 1 mm 14 | 23 | TTTCCCTCACTCCTGCTgGGTGAATTT | 37. |
| DNMT1 site 1 mm 15 | 23 | TTTCCCTCACTCCTGCTCcGTGAATTT | 38. |
| DNMT1 site 1 mm 16 | 23 | TTTCCCTCACTCCTGCTCGcTGAATTT | 39. |
| DNMT1 site 1 mm 17 | 23 | TTTCCCTCACTCCTGCTCGGaGAATTT | 40. |
| DNMT1 site 1 mm 18 | 23 | TTTCCCTCACTCCTGCTCGGTcAATTT | 41. |
| DNMT1 site 1 mm 19 | 23 | TTTCCCTCACTCCTGCTCGGTGtATTT | 42. |
| DNMT1 site 1 mm 20 | 23 | TTTCCCTCACTCCTGCTCGGTGAtTTT | 43. |

-continued

| | | | |
|---|---|---|---|
| DNMT1 site 1 mm 21 | 23 | TTTCCCTCACTCCTGCTCGGTGAAaTT | 44. |
| DNMT1 site 1 mm 22 | 23 | TTTCCCTCACTCCTGCTCGGTGAATaT | 45. |
| DNMT1 site 1 mm 23 | 23 | TTTCCCTCACTCCTGCTCGGTGAATTa | 46. |
| DNMT1 site 1 | 26 | TTTCCCTCACTCCTGCTCGGTGAATTTGGC | 47. |
| DNMT1 site 1 | 25 | TTTCCCTCACTCCTGCTCGGTGAATTTGG | 48. |
| DNMT1 site 1 | 24 | TTTCCCTCACTCCTGCTCGGTGAATTTG | 49. |
| DNMT1 site 1 | 22 | TTTCCCTCACTCCTGCTCGGTGAATT | 50. |
| DNMT1 site 1 | 21 | TTTCCCTCACTCCTGCTCGGTGAAT | 51. |
| DNMT1 site 1 | 20 | TTTCCCTCACTCCTGCTCGGTGAA | 52. |
| DNMT1 site 1 mm 1 | 20 | TTTCgCTCACTCCTGCTCGGTGAA | 53. |
| DNMT1 site 1 mm 2 | 20 | TTTCCgTCACTCCTGCTCGGTGAA | 54. |
| DNMT1 site 1 mm 3 | 20 | TTTCCCaCACTCCTGCTCGGTGAA | 55. |
| DNMT1 site 1 mm 4 | 20 | TTTCCCTgACTCCTGCTCGGTGAA | 56. |
| DNMT1 site 1 mm 5 | 20 | TTTCCCTCtCTCCTGCTCGGTGAA | 57. |
| DNMT1 site 1 mm 6 | 20 | TTTCCCTCAgTCCTGCTCGGTGAA | 58. |
| DNMT1 site 1 mm 7 | 20 | TTTCCCTCACaCCTGCTCGGTGAA | 59. |
| DNMT1 site 1 mm 8 | 20 | TTTCCCTCACTgCTGCTCGGTGAA | 60. |
| DNMT1 site 1 mm 9 | 20 | TTTCCCTCACTCgTGCTCGGTGAA | 61. |
| DNMT1 site 1 mm 10 | 20 | TTTCCCTCACTCCaGCTCGGTGAA | 62. |
| DNMT1 site 1 mm 11 | 20 | TTTCCCTCACTCCTcCTCGGTGAA | 63. |
| DNMT1 site 1 mm 12 | 20 | TTTCCCTCACTCCTGgTCGGTGAA | 64. |
| DNMT1 site 1 mm 13 | 20 | TTTCCCTCACTCCTGCaCGGTGAA | 65. |
| DNMT1 site 1 mm 14 | 20 | TTTCCCTCACTCCTGCTgGGTGAA | 66. |
| DNMT1 site 1 mm 15 | 20 | TTTCCCTCACTCCTGCTCcGTGAA | 67. |
| DNMT1 site 1 mm 16 | 20 | TTTCCCTCACTCCTGCTCGcTGAA | 68. |
| DNMT1 site 1 mm 17 | 20 | TTTCCCTCACTCCTGCTCGGaGAA | 69. |
| DNMT1 site 1 mm 18 | 20 | TTTCCCTCACTCCTGCTCGGTcAA | 70. |
| DNMT1 site 1 mm 19 | 20 | TTTCCCTCACTCCTGCTCGGTGtA | 71. |
| DNMT1 site 1 mm 20 | 20 | TTTCCCTCACTCCTGCTCGGTGAt | 72. |
| DNMT1 site 1 | 19 | TTTCCCTCACTCCTGCTCGGTGA | 73. |
| DNMT1 site 1 | 18 | TTTCCCTCACTCCTGCTCGGTG | 74. |
| DNMT1 site 1 | 17 | TTTCCCTCACTCCTGCTCGGT | 75. |
| DNMT1 site 1 | 16 | TTTCCCTCACTCCTGCTCGG | 76. |
| DNMT1 site 2 | 23 | TTTGAGGAGTGTTCAGTCTCCGTGAAC | 77. |
| DNMT1 site 3 | 23 | TTTCCTGATGGTCCATGTCTGTTACTC | 78. |
| DNMT1 site 3 mm 1 & 2 | 23 | TTTCgaGATGGTCCATGTCTGTTACTC | 79. |
| DNMT1 site 3 mm 3 & 4 | 23 | TTTCCTctTGGTCCATGTCTGTTACTC | 80. |
| DNMT1 site 3 mm 5 & 6 | 23 | TTTCCTGAacGTCCATGTCTGTTACTC | 81. |
| DNMT1 site 3 mm 7 & 8 | 23 | TTTCCTGATGcaCCATGTCTGTTACTC | 82. |
| DNMT1 site 3 mm 9 & 10 | 23 | TTTCCTGATGGTggATGTCTGTTACTC | 83. |

-continued

| | | | |
|---|---|---|---|
| DNMT1 site 3 mm 11 & 12 | 23 | TTTCCTGATGGTCCtaGTCTGTTACTC | 84. |
| DNMT1 site 3 mm 13 & 14 | 23 | TTTCCTGATGGTCCATcaCTGTTACTC | 85. |
| DNMT1 site 3 mm 15 & 16 | 23 | TTTCCTGATGGTCCATGTgaGTTACTC | 86. |
| DNMT1 site 3 mm 17 & 18 | 23 | TTTCCTGATGGTCCATGTCTcaTACTC | 87. |
| DNMT1 site 3 mm 19 & 20 | 23 | TTTCCTGATGGTCCATGTCTGTatCTC | 88. |
| DNMT1 site 3 mm 21 & 22 | 23 | TTTCCTGATGGTCCATGTCTGTTAgaC | 89. |
| DNMT1 site 3 mm 22 & 23 | 23 | TTTCCTGATGGTCCATGTCTGTTACag | 90. |
| DNMT1 site 3 mm 1 | 23 | TTTCgTGATGGTCCATGTCTGTTACTC | 91. |
| DNMT1 site 3 mm 2 | 23 | TTTCCaGATGGTCCATGTCTGTTACTC | 92. |
| DNMT1 site 3 mm 3 | 23 | TTTCCTcATGGTCCATGTCTGTTACTC | 93. |
| DNMT1 site 3 mm 4 | 23 | TTTCCTGtTGGTCCATGTCTGTTACTC | 94. |
| DNMT1 site 3 mm 5 | 23 | TTTCCTGAaGGTCCATGTCTGTTACTC | 95. |
| DNMT1 site 3 mm 6 | 23 | TTTCCTGATcGTCCATGTCTGTTACTC | 96. |
| DNMT1 site 3 mm 7 | 23 | TTTCCTGATGcTCCATGTCTGTTACTC | 97. |
| DNMT1 site 3 mm 8 | 23 | TTTCCTGATGGaCCATGTCTGTTACTC | 98. |
| DNMT1 site 3 mm 9 | 23 | TTTCCTGATGGTgCATGTCTGTTACTC | 99. |
| DNMT1 site 3 mm 10 | 23 | TTTCCTGATGGTCgATGTCTGTTACTC | 100. |
| DNMT1 site 3 mm 11 | 23 | TTTCCTGATGGTCCtTGTCTGTTACTC | 101. |
| DNMT1 site 3 mm 12 | 23 | TTTCCTGATGGTCCAaGTCTGTTACTC | 102. |
| DNMT1 site 3 mm 13 | 23 | TTTCCTGATGGTCCATcTCTGTTACTC | 103. |
| DNMT1 site 3 mm 14 | 23 | TTTCCTGATGGTCCATGaCTGTTACTC | 104. |
| DNMT1 site 3 mm 15 | 23 | TTTCCTGATGGTCCATGTgTGTTACTC | 105. |
| DNMT1 site 3 mm 16 | 23 | TTTCCTGATGGTCCATGTCaGTTACTC | 106. |
| DNMT1 site 3 mm 17 | 23 | TTTCCTGATGGTCCATGTCTcTTACTC | 107. |
| DNMT1 site 3 mm 18 | 23 | TTTCCTGATGGTCCATGTCTGaTACTC | 108. |
| DNMT1 site 3 mm 19 | 23 | TTTCCTGATGGTCCATGTCTGTaACTC | 109. |
| DNMT1 site 3 mm 20 | 23 | TTTCCTGATGGTCCATGTCTGTTtCTC | 110. |
| DNMT1 site 3 mm 21 | 23 | TTTCCTGATGGTCCATGTCTGTTAgTC | 111. |
| DNMT1 site 3 mm 22 | 23 | TTTCCTGATGGTCCATGTCTGTTACaC | 112. |
| DNMT1 site 3 mm 23 | 23 | TTTCCTGATGGTCCATGTCTGTTACTg | 113. |
| DNMT1 site 3 | 26 | TTTCCTGATGGTCCATGTCTGTTACTCGCC | 114. |
| DNMT1 site 3 | 25 | TTTCCTGATGGTCCATGTCTGTTACTCGC | 115. |
| DNMT1 site 3 | 24 | TTTCCTGATGGTCCATGTCTGTTACTCG | 116. |
| DNMT1 site 3 | 22 | TTTCCTGATGGTCCATGTCTGTTACT | 117. |
| DNMT1 site 3 | 21 | TTTCCTGATGGTCCATGTCTGTTAC | 118. |
| DNMT1 site 3 | 20 | TTTCCTGATGGTCCATGTCTGTTA | 119. |
| DNMT1 site 3 mm 1 | 20 | TTTCgTGATGGTCCATGTCTGTTA | 120. |
| DNMT1 site 3 mm 2 | 20 | TTTCCaGATGGTCCATGTCTGTTA | 121. |
| DNMT1 site 3 mm 3 | 20 | TTTCCTcATGGTCCATGTCTGTTA | 122. |

-continued

| | | | |
|---|---|---|---|
| DNMT1 site 3 mm 4 | 20 | TTTCCTGtTGGTCCATGTCTGTTA | 123. |
| DNMT1 site 3 mm 5 | 20 | TTTCCTGAaGGTCCATGTCTGTTA | 124. |
| DNMT1 site 3 mm 6 | 20 | TTTCCTGATcGTCCATGTCTGTTA | 125. |
| DNMT1 site 3 mm 7 | 20 | TTTCCTGATGcTCCATGTCTGTTA | 126. |
| DNMT1 site 3 mm 8 | 20 | TTTCCTGATGGaCCATGTCTGTTA | 127. |
| DNMT1 site 3 mm 9 | 20 | TTTCCTGATGGTgCATGTCTGTTA | 128. |
| DNMT1 site 3 mm 10 | 20 | TTTCCTGATGGTCgATGTCTGTTA | 129. |
| DNMT1 site 3 mm 11 | 20 | TTTCCTGATGGTCCtTGTCTGTTA | 130. |
| DNMT1 site 3 mm 12 | 20 | TTTCCTGATGGTCCAaGTCTGTTA | 131. |
| DNMT1 site 3 mm 13 | 20 | TTTCCTGATGGTCCATcTCTGTTA | 132. |
| DNMT1 site 3 mm 14 | 20 | TTTCCTGATGGTCCATGaCTGTTA | 133. |
| DNMT1 site 3 mm 15 | 20 | TTTCCTGATGGTCCATGTgTGTTA | 134. |
| DNMT1 site 3 mm 16 | 20 | TTTCCTGATGGTCCATGTCaGTTA | 135. |
| DNMT1 site 3 mm 17 | 20 | TTTCCTGATGGTCCATGTCTcTTA | 136. |
| DNMT1 site 3 mm 18 | 20 | TTTCCTGATGGTCCATGTCTGaTA | 137. |
| DNMT1 site 3 mm 19 | 20 | TTTCCTGATGGTCCATGTCTGTaA | 138. |
| DNMT1 site 3 mm 20 | 20 | TTTCCTGATGGTCCATGTCTGTTt | 139. |
| DNMT1 site 3 | 19 | TTTCCTGATGGTCCATGTCTGTT | 140. |
| DNMT1 site 3 | 18 | TTTCCTGATGGTCCATGTCTGT | 141. |
| DNMT1 site 3 | 17 | TTTCCTGATGGTCCATGTCTG | 142. |
| DNMT1 site 3 | 16 | TTTCCTGATGGTCCATGTCT | 143. |
| DNMT1 site 4 | 23 | TTTATTTCCCTTCAGCTAAAATAAAGG | 144. |
| DNMT1 site 5 | 23 | TTTATTTTAGCTGAAGGGAAATAAAAG | 145. |
| DNMT1 site 6 | 23 | TTTTATTTCCCTTCAGCTAAAATAAAG | 146. |
| DNMT1 site 7 | 23 | TTTGGCTCAGCAGGCACCTGCCTCAGC | 147. |
| DNMT1 site 7 mm 1 & 2 | 23 | TTTGcgTCAGCAGGCACCTGCCTCAGC | 148. |
| DNMT1 site 7 mm 3 & 4 | 23 | TTTGGCagAGCAGGCACCTGCCTCAGC | 149. |
| DNMT1 site 7 mm 5 & 6 | 23 | TTTGGCTCtcCAGGCACCTGCCTCAGC | 150. |
| DNMT1 site 7 mm 7 & 8 | 23 | TTTGGCTCAGgtGGCACCTGCCTCAGC | 151. |
| DNMT1 site 7 mm 9 & 10 | 23 | TTTGGCTCAGCAccCACCTGCCTCAGC | 152. |
| DNMT1 site 7 mm 11 & 12 | 23 | TTTGGCTCAGCAGGgtCCTGCCTCAGC | 153. |
| DNMT1 site 7 mm 13 & 14 | 23 | TTTGGCTCAGCAGGCAggTGCCTCAGC | 154. |
| DNMT1 site 7 mm 15 & 16 | 23 | TTTGGCTCAGCAGGCACCacCCTCAGC | 155. |
| DNMT1 site 7 mm 17 & 18 | 23 | TTTGGCTCAGCAGGCACCTGggTCAGC | 156. |
| DNMT1 site 7 mm 19 & 20 | 23 | TTTGGCTCAGCAGGCACCTGCCagAGC | 157. |
| DNMT1 site 7 mm 21 & 22 | 23 | TTTGGCTCAGCAGGCACCTGCCTCtcC | 158. |
| DNMT1 site 7 mm 22 & 23 | 23 | TTTGGCTCAGCAGGCACCTGCCTCAcg | 159. |
| DNMT1 site 7 | 26 | TTTGGCTCAGCAGGCACCTGCCTCAGCTGC | 160. |
| DNMT1 site 7 | 25 | TTTGGCTCAGCAGGCACCTGCCTCAGCTG | 161. |
| DNMT1 site 7 | 24 | TTTGGCTCAGCAGGCACCTGCCTCAGCT | 162. |

-continued

| | | | |
|---|---|---|---|
| DNMT1 site 7 | 22 | TTTGGCTCAGCAGGCACCTGCCTCAG | 163. |
| DNMT1 site 7 | 21 | TTTGGCTCAGCAGGCACCTGCCTCA | 164. |
| DNMT1 site 7 | 20 | TTTGGCTCAGCAGGCACCTGCCTC | 165. |
| DNMT1 site 7 | 19 | TTTGGCTCAGCAGGCACCTGCCT | 166. |
| DNMT1 site 7 | 18 | TTTGGCTCAGCAGGCACCTGCC | 167. |
| DNMT1 site 7 | 17 | TTTGGCTCAGCAGGCACCTGC | 168. |
| DNMT1 site 7 | 16 | TTTGGCTCAGCAGGCACCTG | 169. |
| | | EMX1 | |
| EMX1 site 1 | 23 | TTTCTCATCTGTGCCCCTCCCTCCCTG | 170. |
| EMX1 site 2 | 23 | TTTGTCCTCCGGTTCTGGAACCACACC | 171. |
| EMX1 site 3 | 23 | TTTGTGGTTGCCCACCCTAGTCATTGG | 172. |
| EMX1 site 4 | 23 | TTTGTACTTTGTCCTCCGGTTCTGGAA | 173. |
| | | FANCF | |
| FANCF site 1 | 23 | TTTGGGCGGGGTCCAGTTCCGGGATTA | 174. |
| FANCF site 2 | 23 | TTTGGTCGGCATGGCCCCATTCGCACG | 175. |
| FANCF site 3 | 23 | TTTTCCGAGCTTCTGGCGGTCTCAAGC | 176. |
| FANCF site 4 | 23 | TTTCACCTTGGAGACGGCGACTCTCTG | 177. |
| | | RUNX1 | |
| RUNX1 site 1 | 23 | TTTTCAGGAGGAAGCGATGGCTTCAGA | 178. |
| RUNX1 site 2 | 23 | TTTCGCTCCGAAGGTAAAAGAAATCAT | 179. |
| RUNX1 site 3 | 23 | TTTCAGCCTCACCCCTCTAGCCCTACA | 180. |
| RUNX1 site 4 | 23 | TTTCTTCTCCCCTCTGCTGGATACCTC | 181. |

mm: mismatched positions; mismatches which are shown in lower case

SpCas9 gRNAs

| Name | Spacer length (nt) | Spacer Sequence | |
|---|---|---|---|
| | | DNMT1 | |
| DNMT1 site 1 | 20 | GTCACTCTGGGGAACACGCC | 182. |
| DNMT1 site 2 | 20 | GAGTGCTAAGGGAACGTTCA | 183. |
| DNMT1 site 3 | 20 | GAGACTGAACACTCCTCAAA | 184. |
| DNMT1 site 4 | 20 | GGAGTGAGGGAAACGGCCCC | 185. |
| | | EMX1 | |
| EMX1 site 1 | 20 | GAGTCCGAGCAGAAGAAGAA | 186. |
| EMX1 site 2 | 20 | GTCACCTCCAATGACTAGGG | 187. |
| | | FANCF | |
| FANCF site 1 | 20 | GGAATCCCTTCTGCAGCACC | 188. |
| FANCF site 2 | 20 | GCTGCAGAAGGGATTCCATG | 189. |

-continued

| RUNX1 | | | |
|---|---|---|---|
| RUNX1 site 1 | 20 | GCATTTTCAGGAGGAAGCGA | 190. |
| RUNX1 site 2 | 20 | GGGAGAAGAAAGAGAGATGT | 191. |

Figure 1B:
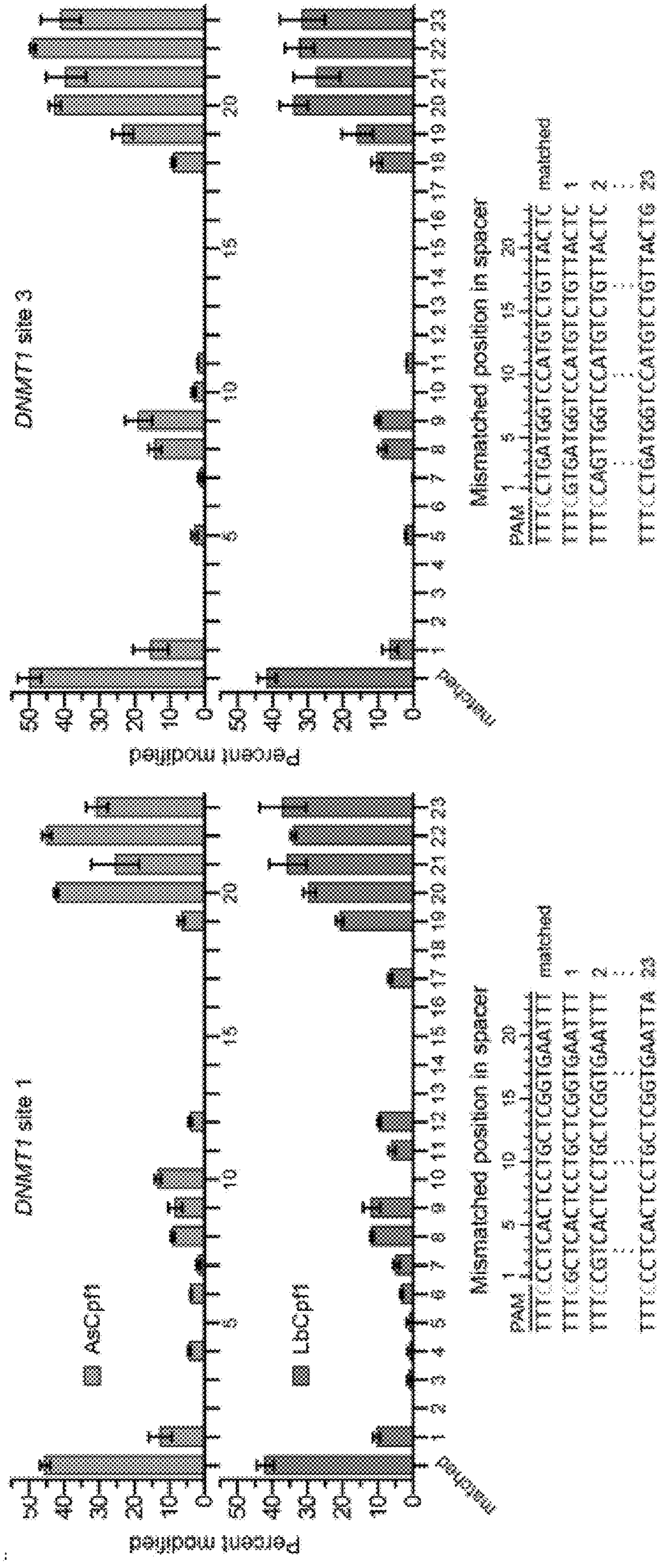

Example 1. Tolerance of AsCpf1 and LbCpf1 to Mismatches in crRNA: Target Site Duplex In a recent publication (Kleinstiver & Tsai et al., Nature Biotechnology 2016) using 3 different crRNAs targeted to endogenous sites in the human DNMT1 gene, it was determined that both AsCpf1 and LbCpf1 are nearly completely intolerant to pairs of adjacent mismatches in their crRNA: target-site duplex (FIG. 1*a*). Compared to the indel formation activity with any of the 3 perfectly matched crRNAs, pairs of mismatches in the crRNA between positions 1/2 to 17/18 nearly completely eliminated detectable indel formation. We also tested the tolerance of both Cpf1s to single mismatches across the length of two different sites and found that AsCpf1 and LbCpf1 could generally discriminate against sites where the crRNA contained a single mismatch at positions 2-6 and 13-17 (FIG. 1*b*). Conversely, both Cpf1 orthologues could tolerate single mismatches at positions 1 and 7-12 with varying degrees of efficiency (FIG. 1*b*). From both singly- and doubly-mismatched crRNA experiments, it was clear that Cpf1 did not have specificity at positions 18-23 of the spacer and could tolerate single and double mismatches in this region.

Figure 2A:
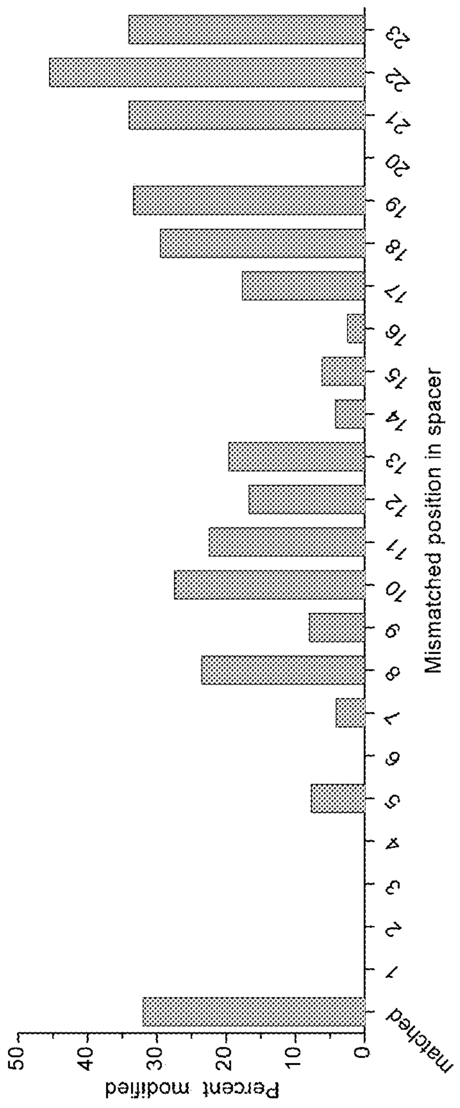
FIGS. 2A-B are bar graphs showing tolerance of LbCpf1 (2A) and AsCpf1 (2B) to singly mismatched crRNAs for DNMT1 site 7. Endogenous gene modification by AsCpf1 and LbCpf1 determined by T7E1 assay; n=1; n.d., not determined.
Figure 2B:
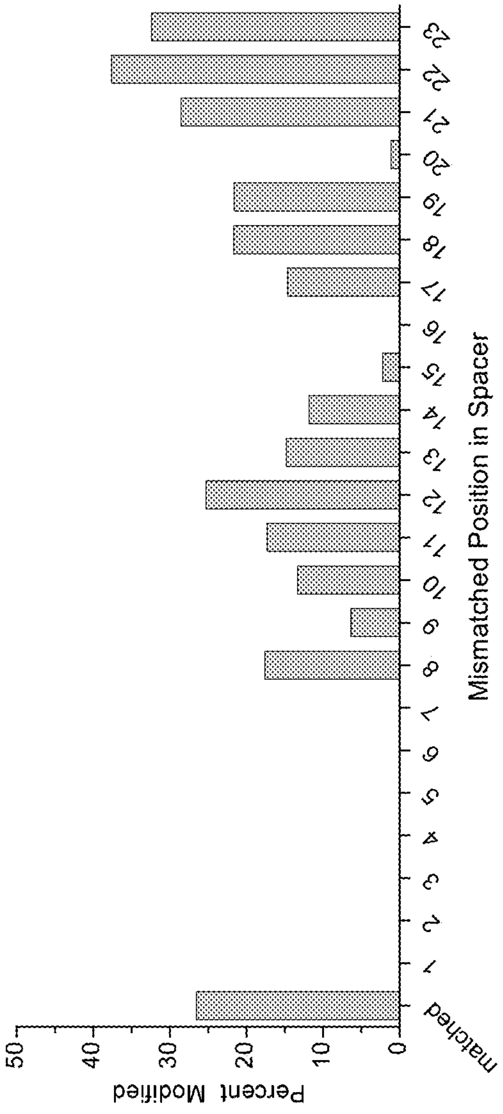

More recently, the tolerance of LbCpf1 and AsCpf1 to single mismatches across a third spacer sequence was also examined; while single mismatches at positions 1-4 and 6 abolished cleavage, the remainder of singly-mismatched crRNAs were competent to generate indel mutations with LbCpf1 and AsCpf1 (FIGS. 2A and 2B, respectively).

Overall, these combined experiments demonstrate that although both AsCpf1 and LbCpf1 generally have high genome-wide specificity and can be intolerant to single mismatches across their target site spacer regions, there are a number of positions at which single substitutions are tolerated and could potentially lead to off-target effects. Thus, we were interested in taking a rational approach to engineer high-fidelity Cpf1 (Cpf1-HF) variants that would be unable to tolerate any singly mismatched positions across the entire spacer sequence. These Cpf1-HF variants would be useful for studies that require single-nucleotide resolution in genome-editing applications, such as distinguishing and preferentially editing alleles that differ by a single base change (such as SNPs).

Example 2. Cpf1-HF

A recent crystal structure of AsCpf1 (Yamano et al., Cell 2016) enabled us to look carefully at the 3D-structure of Cpf1 and examine potential amino acid side chains that make non-specific contacts to the DNA backbone (Table 1). We identified a number of AsCpf1 residues whose side-chains appeared to be within contact distance of either the target or non-target DNA strands as candidates to mutate. Similar amino acid positions of LbCpf1 (for which no crystal structure is publicly available) were predicted by generating sequence alignments with AsCpf1 and other Cpf1 orthologues, and then identifying residues that are in homologous positions and contain similar functional groups (Table 1).

TABLE 1

Amino acids of AsCpf1 and LbCpf1 that are predicted to I tried make non-specific contacts to the target and non-target DNA strands

| Target strand contacts | | Non-target strand contacts | |
|---|---|---|---|
| AsCpf1 | LbCpf1 (−18)* | AsCpf1 | LbCpf1 (−18)* |
| N178 | N160 | K85 | K83 |
| S186 | S168 | K87 | R86 |
| N278 | N256 | R92 | K89, K92 |
| N282 | N260 | N93 | N91 |
| R301 | K272 | R113 | N112 |
| T315 | S286 | K200 | R182 |
| S376 | K349 | R210 | K192 |
| N515 | D505 | K403 | K380 |
| R518 | R508 | K406 | R385, R386, K387 |
| N519 | N509 | Q611 | K600 |
| K523 | Q513 | K613 | K601 |
| K524 | K514 | N647 | N607 |
| K603 | K591 | K653 | K614 |
| K780 | R737 | Q656 | K617, N618 |
| Q784 | G741 | K661 | K622 |
| R951 | R883 | K662 | K623 |
| K965 | K897 | K887 | K811 |
| Q1013 | K944 | R909 | R833 |
| Q1014 | S945 | K1086 | K1017 |
| K1017 | K948i | R1094 | K1025, K1026 |
| K1054 | | K1118 | — |
| | | R1121 | K1050 |
| | | R1127 | R1054 |
| | | R1174 | K1096 |
| | | R1220 | — |
| | | K1288 | K1200, K1205 |
| | | N1291 | K1208 |

*amino acids 1-1228 of SEQ ID NO:10.

Figure 3:
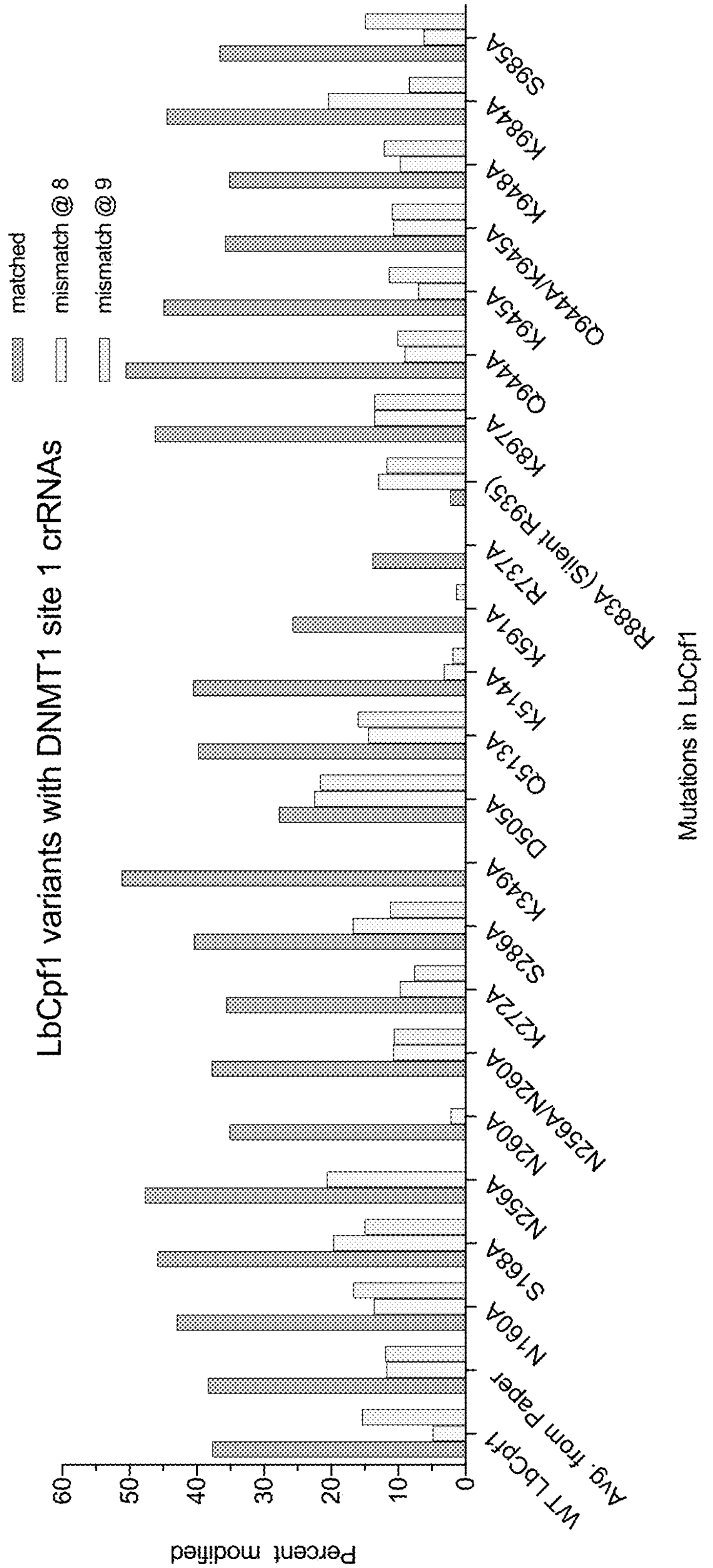
FIG. 3 is a bar graph showing wild-type LbCpf1 and alanine substitution variant activity with matched and singly mismatched crRNAs for DNMT1 site 1. Endogenous gene modification determined by T7E1 assay; n=1.
Figure 4:
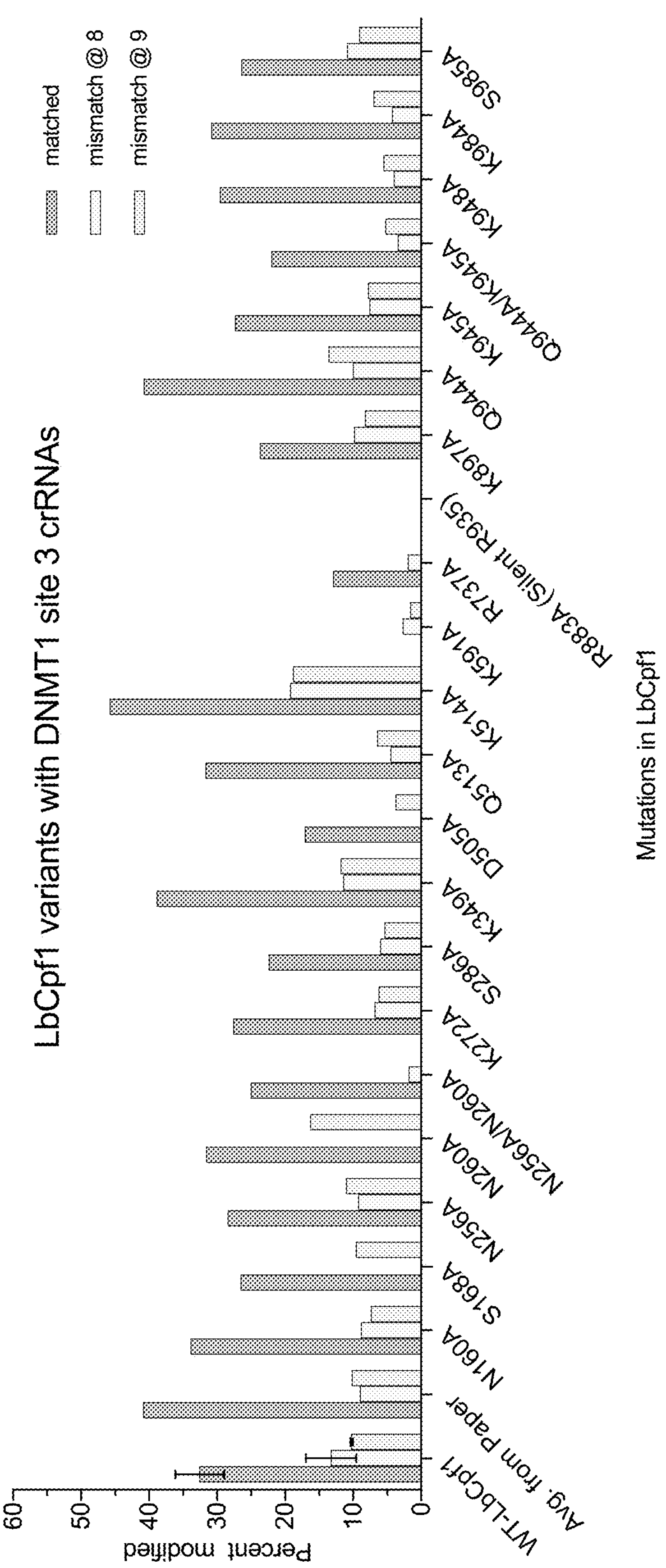
FIG. 4 is a bar graph showing wild-type LbCpf1 and alanine substitution variant activity with matched and singly mismatched crRNAs for DNMT1 site 3. Endogenous gene modification determined by T7E1 assay; n=1; error bars, s.e.m. for n=2.

To test the hypothesis of whether alanine substitution of amino acids that potentially make non-specific contacts to the target strand DNA can reduce tolerance of mismatches in the crRNA: target duplex, the activity of multiple LbCpf1 variants was first examined. Using crRNAs that were either matched (for on-target activity) or contained mismatches at positions 8 or 9 (to mimic off-target sites) targeted to DNMT1 sites 1 and 3 (FIGS. 3 and 4, respectively), a number of variants appear to reduce activities with the mismatched crRNAs without dramatic effects on on-target activities.

Given these initial results, it is very likely that combinations of mutations that show improved specificities individually may show even more substantial improvements in specificities. The activities of such variants are examined using an expanded panel of matched and mismatched crRNAs.

Figure 5A:
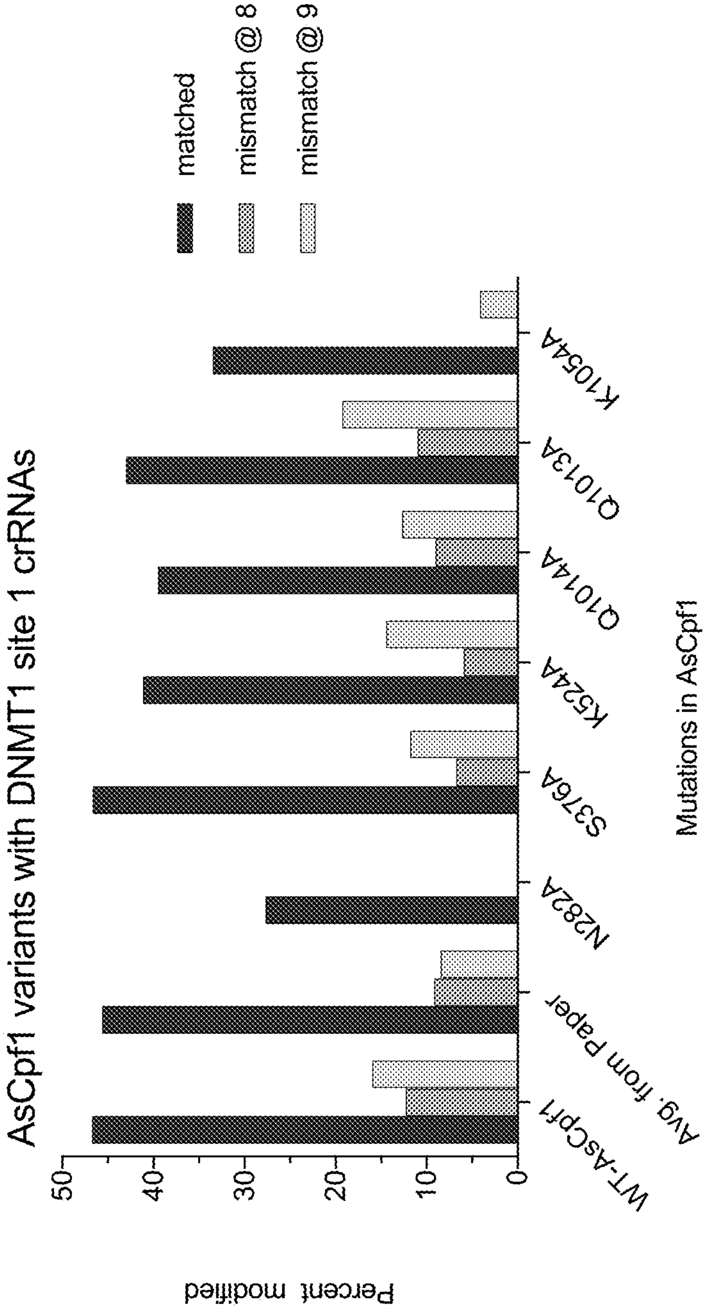
FIG. 5A-B are bar graphs showing wild-type AsCpf1 and alanine substitution variant activity with matched and singly mismatched crRNAs for DNMT1 site 1. Panels A and B are from separate experiments. Endogenous gene modification determined by T7E1 assay; n=1.
Figure 5B:
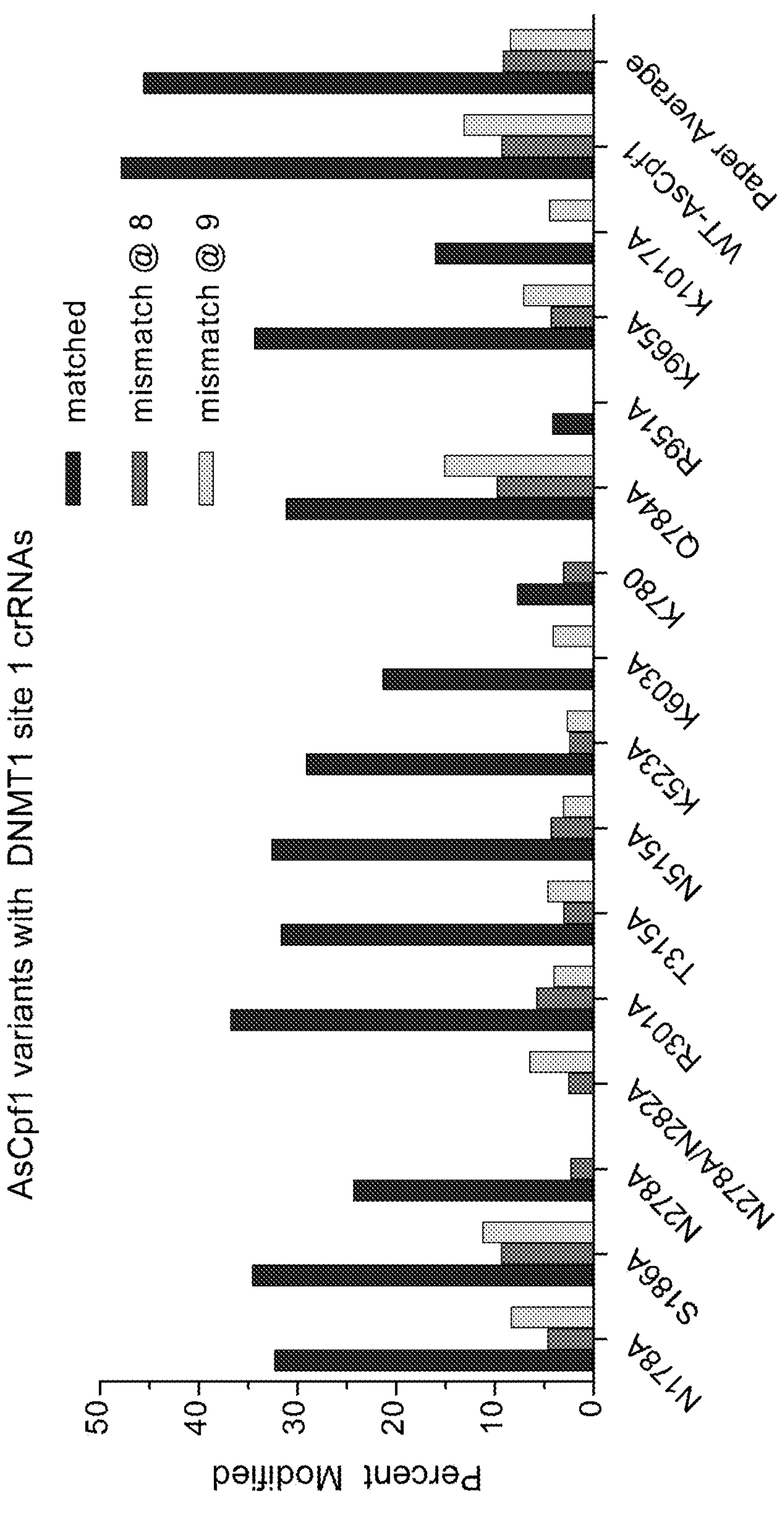
Figure 6:
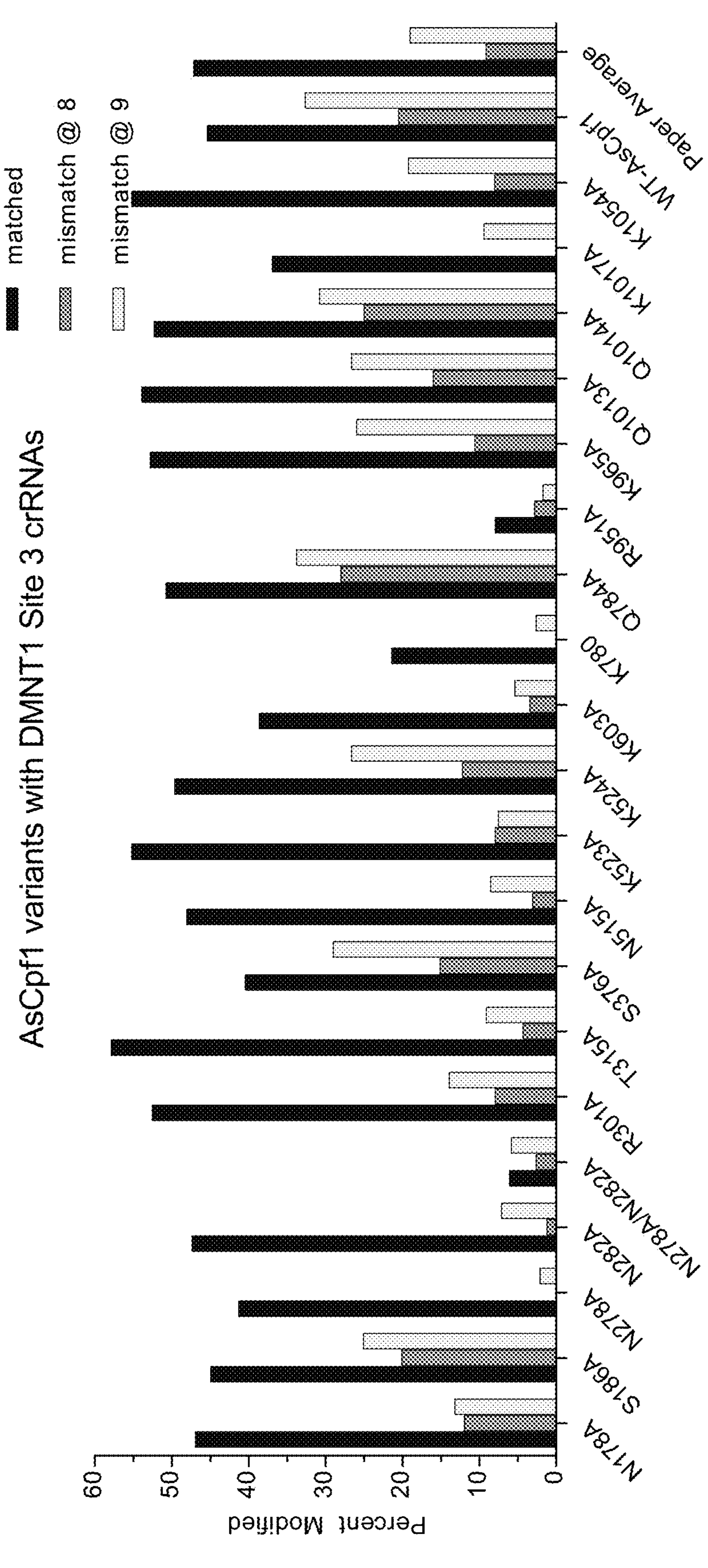
FIG. 6 is a bar graph showing wild-type AsCpf1 and alanine substitution variant activity with matched and singly mismatched crRNAs for DNMT1 site 3. Endogenous gene modification determined by T7E1 assay; n=1.

Next, to perform an initial screen of AsCpf1 variants whose mutations are homologous to those of the LbCpf1 variants that appeared most promising, the activity of a subset of possible variants was examined using the crRNAs that were matched for DNMT1 site 1 or contained single mismatches at positions 8 or 9 (FIGS. 5A and 5B). A larger number of AsCpf1 variants were tested using crRNAs that were either matched (for on-target activity) or contained mismatches at positions 8 or 9 (to mimic off-target sites) targeted to DNMT1 site 3 (FIG. 6). A number of variants appear to reduce activities with the mismatched crRNAs without dramatic effects on on-target activities. Additional untested mutations and combinations thereof may yield improvements in their abilities to discriminate against mismatched sites.

REFERENCES

1. Zetsche, B. et al. Cpf1 Is a Single RNA-Guided Endonuclease of a Class 2 CRISPR-Cas System. Cell 163, 759-771 (2015).
2 Sander, J. D. & Joung, J. K. CRISPR-Cas systems for editing, regulating and targeting genomes. Nat Biotechnol 32, 347-355 (2014).
3. Hsu, P. D., Lander, E. S. & Zhang, F. Development and applications of CRISPR-Cas9 for genome engineering. Cell 157, 1262-1278 (2014).
4. Doudna, J. A. & Charpentier, E. Genome editing. The new frontier of genome engineering with CRISPR-Cas9. Science 346, 1258096 (2014).
5. Maeder, M. L. & Gersbach, C. A. Genome-editing Technologies for Gene and Cell Therapy. Mol Ther (2016).
6. Wright, A. V., Nunez, J. K. & Doudna, J. A. Biology and Applications of CRISPR Systems: Harnessing Nature's Toolbox for Genome Engineering. Cell 164, 29-44 (2016).
7. Jinek, M. et al. A programmable dual-RNA-guided DNA endonuclease in adaptive bacterial immunity. Science 337, 816-821 (2012).
8. Deltcheva, E. et al. CRISPR RNA maturation by trans-encoded small RNA and host factor RNase III. Nature 471, 602-607 (2011).
9. Cong, L. et al. Multiplex genome engineering using CRISPR/Cas systems. Science 339, 819-823 (2013).
10. Mali, P. et al. RNA-guided human genome engineering via Cas9. Science 339, 823-826 (2013).
11. Jinek, M. et al. RNA-programmed genome editing in human cells. Elife 2, e00471 (2013).
12. Tsai, S. Q. et al. GUIDE-seq enables genome-wide profiling of off-target cleavage by CRISPR-Cas nucleases. Nat Biotechnol 33, 187-197 (2015).
13. Frock, R. L. et al. Genome-wide detection of DNA double-stranded breaks induced by engineered nucleases. Nat Biotechnol 33, 179-186 (2015).
14. Wang, X. et al. Unbiased detection of off-target cleavage by CRISPR-Cas9 and TALENs using integrase-defective lentiviral vectors. Nat Biotechnol 33, 175-178 (2015).
15. Kim, D. et al. Digenome-seq: genome-wide profiling of CRISPR-Cas9 off-target effects in human cells. Nat Methods 12, 237-243, 231 p following 243 (2015).
16. Kleinstiver, B. P. et al. High-fidelity CRISPR-Cas9 nucleases with no detectable genome-wide off-target effects. Nature 529, 490-495 (2016).
17. Slaymaker, I. M. et al. Rationally engineered Cas9 nucleases with improved specificity. Science 351, 84-88 (2016).
18. Schunder, E., Rydzewski, K., Grunow, R. & Heuner, K. First indication for a functional CRISPR/Cas system in *Francisella tularensis*. Int J Med Microbiol 303, 51-60 (2013).
19. Makarova, K. S. et al. An updated evolutionary classification of CRISPR-Cas systems. Nat Rev Microbiol 13, 722-736 (2015).
20. Fagerlund, R. D., Staals, R. H. & Fineran, P. C. The Cpf1 CRISPR-Cas protein expands genome-editing tools. Genome Biol 16, 251 (2015).
21. Bae, S., Park, J. & Kim, J. S. Cas-OFFinder: a fast and versatile algorithm that searches for potential off-target sites of Cas9 RNA-guided endonucleases. Bioinformatics 30, 1473-1475 (2014).
22. Fu, Y., Sander, J. D., Reyon, D., Cascio, V. M. & Joung, J. K. Improving CRISPR-Cas nuclease specificity using truncated guide RNAs. Nat Biotechnol 32, 279-284 (2014).
23. Kleinstiver, B. P. et al. Broadening the targeting range of *Staphylococcus aureus* CRISPR-Cas9 by modifying PAM recognition. Nat Biotechnol (2015).
24. Kleinstiver, B. P. et al. Engineered CRISPR-Cas9 nucleases with altered specificities. Nature 523, 481-485 (2015).
25. Yin, H. et al. Therapeutic genome editing by combined viral and non-viral delivery of CRISPR system components in vivo. Nat Biotechnol (2016).
26. Bolukbasi, M. F. et al. DNA-binding-domain fusions enhance the targeting range and precision of Cas9. Nat Methods (2015).
27. Friedland, A. E. et al. Characterization of *Staphylococcus aureus* Cas9: a smaller Cas9 for all-in-one adeno-associated virus delivery and paired nickase applications. Genome Biol 16, 257 (2015).
28. Tsai, S. Q. et al. Dimeric CRISPR RNA-guided FokI nucleases for highly specific genome editing. Nat Biotechnol 32, 569-576 (2014).
29. Reyon, D. et al. FLASH assembly of TALENs for high-throughput genome editing. Nat Biotechnol 30, 460-465 (2012).
30. Tsai, S. Q., Topkar, V. V., Joung, J. K. & Aryee, M. J. Open-source guideseq software for analysis of GUIDE-seq data. Nat Biotechnol 34, 483 (2016).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated CRISPR from *Prevotella* and *Francisella* 1 (Cpf1) protein, wherein the protein is from *Lachnospiraceae bacterium* ND2006 (LbCpf1), comprising a sequence that is at least 80% identical to the amino acid sequence of amino acids 1-1228 of SEQ ID NO: 10, with mutations at one or more of the following positions: N160, S168, N256, N260, K272, S286, K349, D505, Q513, G741, Q944, K945, and/or S985 of amino acids 1-1228 of SEQ ID NO:10.

2. The isolated protein of claim 1, comprising one or more of the following mutations: N160A, S168A, N256A, N260A, K272A, S286A, K349A, D505A, Q513A, G741A, Q944A, K945A, and/or S985A.

3. The isolated protein of claim 1, further comprising one or more mutations that decrease nuclease activity selected from the group consisting of mutations at D832 and E925.

4. The isolated protein of claim 3, comprising mutations D832A and E925A.

5. The isolated protein of claim 1, comprising a sequence that is at least 95% identical to the amino acid sequence of amino acids 1-1228 of SEQ ID NO: 10.

6. The isolated protein of claim 1, further comprising mutations at one or more of the following positions: R508, K514, K591, R737, R883, K897, K948, and/or K984.

7. The isolated protein of claim 6, wherein the mutations are R508A, K514A, K591A, R737A, R883A, K897A, K948A, and/or K984A.

8. A fusion protein comprising the isolated protein of claim 1, fused to a heterologous functional domain, with an optional intervening linker, wherein the Cpf1 protein is capable of interacting with a guide RNA and target DNA.

9. The fusion protein of claim 8, wherein the heterologous functional domain is a transcriptional activation domain.

10. The fusion protein of claim 9, wherein the transcriptional activation domain is from VP64 or NF-κB p65.

11. The fusion protein of claim 8, wherein the heterologous functional domain is a transcriptional silencer or transcriptional repression domain.

12. The fusion protein of claim 11, wherein the transcriptional repression domain is a Krueppel-associated box (KRAB) domain, ERF repressor domain (ERD), or mSin3A interaction domain (SID).

13. The fusion protein of claim 11, wherein the transcriptional silencer is Heterochromatin Protein 1 (HP1).

14. The fusion protein of claim 8, wherein the heterologous functional domain is an enzyme that modifies the methylation state of DNA.

15. The fusion protein of claim 14, wherein the enzyme that modifies the methylation state of DNA is a DNA methyltransferase (DNMT) or a TET protein.

16. The fusion protein of claim 15, wherein the TET protein is TET1.

17. The fusion protein of claim 8, wherein the heterologous functional domain is an enzyme that modifies a histone subunit.

18. The fusion protein of claim 17, wherein the enzyme that modifies a histone subunit is a histone acetyltransferase (HAT), histone deacetylase (HDAC), histone methyltransferase (HMT), or histone demethylase.

19. The fusion protein of claim 8, wherein the heterologous functional domain is a biological tether.

20. The fusion protein of claim 19, wherein the biological tether is MS2, Csy4 or lambda N protein.

21. The fusion protein of claim 8, wherein the heterologous functional domain is FokI.

22. A method of altering the genome of a cell, the method comprising expressing in the cell, or contacting the cell with, the isolated protein or fusion protein of claim 1, and a guide RNA having a region complementary to a selected portion of the genome of the cell.

23. The method of claim 22, wherein the isolated protein or fusion protein comprises one or more of a nuclear localization sequence, cell penetrating peptide sequence, and/or affinity tag.

24. The method of claim 22, wherein the cell is a stem cell.

25. The method of claim 24, wherein the cell is an embryonic stem cell, mesenchymal stem cell, or induced pluripotent stem cell; is in a living animal; or is in an embryo.

26. A method of altering a double stranded DNA (dsDNA) molecule, the method comprising contacting the dsDNA molecule with the isolated protein of claim 1, and a guide RNA having a region complementary to a selected portion of the dsDNA molecule.

27. The method of claim 26, wherein the dsDNA molecule is in vitro.

28. An isolated nucleic acid encoding an isolated Cpf1 protein, wherein the protein is from LbCpf1, comprising a sequence that is at least 80% identical to the amino acid sequence of amino acids 1-1228 of SEQ ID NO: 10, with mutations at one or more of the following positions: N160, S168, N256, N260, K272, S286, K349, D505, Q513, G741, Q944, K945, and/or S985 of amino acids 1-1228 of SEQ ID NO:10.

29. A vector comprising the isolated nucleic acid of claim 28.

30. An isolated host cell, comprising the isolated nucleic acid of claim 28.

31. The isolated host cell of claim 30, wherein the host cell is a mammalian host cell.

32. The isolated nucleic acid of claim 28, wherein the sequence is at least 95% identical to the amino acid sequence of amino acids 1-1228 of SEQ ID NO: 10.

33. The isolated nucleic acid of claim 28, further comprising mutations at one or more of the following positions: R508, K514, K591, R737, R883, K897, K948, and/or K984.

* * * * *